(12) United States Patent
Hewitt et al.

(10) Patent No.: US 12,318,091 B2
(45) Date of Patent: **\*Jun. 3, 2025**

(54) FILAMENTARY DEVICES FOR TREATMENT OF VASCULAR DEFECTS

(71) Applicant: MICROVENTION, INC., Aliso Viejo, CA (US)

(72) Inventors: Todd J. Hewitt, Laguna Niguel, CA (US); Brian E. Merritt, San Clemente, CA (US); William R. Patterson, Huntington Beach, CA (US)

(73) Assignee: MICROVENTION, INC., Aliso Viejo, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/214,676

(22) Filed: Jun. 27, 2023

(65) Prior Publication Data

US 2023/0338035 A1    Oct. 26, 2023

Related U.S. Application Data

(63) Continuation of application No. 17/028,037, filed on Sep. 22, 2020, now Pat. No. 11,723,667, which is a
(Continued)

(51) Int. Cl.
*A61B 17/12* (2006.01)
*A61B 17/00* (2006.01)
*A61B 90/00* (2016.01)

(52) U.S. Cl.
CPC .. *A61B 17/12113* (2013.01); *A61B 17/12013* (2013.01); *A61B 17/12031* (2013.01);
(Continued)

(58) Field of Classification Search
CPC ........ A61B 17/12113; A61B 17/12172; A61B 2017/1205
See application file for complete search history.

(56) References Cited

U.S. PATENT DOCUMENTS

| 3,874,388 A | 4/1975 | King et al. |
| 4,282,875 A | 8/1981 | Serbinenko |

(Continued)

FOREIGN PATENT DOCUMENTS

| AU | 2009242528 | 3/2016 |
| CA | 2722037 | 10/2009 |

(Continued)

OTHER PUBLICATIONS

A Complete Microcatheter Portfolio; A Broad Selection of Microcatheters. Boston Scientific Brochure 2007.
(Continued)

*Primary Examiner* — Julian W Woo
(74) *Attorney, Agent, or Firm* — ONE LLP

(57) ABSTRACT

Devices and methods for treatment of a patient's vasculature may include a resilient self-expanding permeable implant having a plurality of elongate filaments secured in a hub at a proximal end of the permeable implant. Each of the plurality of elongate filaments may have a diameter between about 0.0005 and about 0.005 inches. The implant includes at least some filaments consisting of nitinol and at least some composite filaments that are drawn filled tube wires comprising an external nitinol tube and a radiopaque material concentrically disposed within the external tube. The implant has at least about 40% composite filaments relative to a total number of filaments, and wherein a total number of filaments is about 10 to about 300.

21 Claims, 31 Drawing Sheets

Related U.S. Application Data continuation of application No. 16/163,287, filed on Oct. 17, 2018, now Pat. No. 10,813,645, which is a continuation of application No. 15/336,634, filed on Oct. 27, 2016, now Pat. No. 10,136,896, which is a continuation of application No. 15/071,632, filed on Mar. 16, 2016, now Pat. No. 9,492,174, which is a continuation of application No. 14/871,352, filed on Sep. 30, 2015, now Pat. No. 9,295,473, which is a continuation of application No. 14/743,627, filed on Jun. 18, 2015, now Pat. No. 9,198,670, which is a continuation of application No. 14/459,638, filed on Aug. 14, 2014, now Pat. No. 9,078,658.

(60) Provisional application No. 61/866,993, filed on Aug. 16, 2013.

(52) U.S. Cl.
CPC .. *A61B 17/12118* (2013.01); *A61B 17/12145* (2013.01); *A61B 17/12172* (2013.01); *A61B 17/12177* (2013.01); *A61B 17/12186* (2013.01); *A61B 2017/00292* (2013.01); *A61B 2017/00526* (2013.01); *A61B 2017/00539* (2013.01); *A61B 2017/00778* (2013.01); *A61B 2017/00862* (2013.01); *A61B 2017/00867* (2013.01); *A61B 2017/1205* (2013.01); *A61B 2017/12068* (2013.01); *A61B 2017/1209* (2013.01); *A61B 2017/12095* (2013.01); *A61B 2090/3966* (2016.02)

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Molgaard-Nielsen et al. |
| 4,675,361 A | 6/1987 | Ward |
| 4,729,278 A | 3/1988 | Graeff |
| 4,998,539 A | 3/1991 | Delsanti |
| 5,061,275 A | 10/1991 | Wallsten et al. |
| 5,071,407 A | 12/1991 | Termin et al. |
| 5,108,407 A | 4/1992 | Geremia et al. |
| 5,122,136 A | 6/1992 | Gluglielmi et al. |
| 5,154,705 A | 10/1992 | Fleischhacker et al. |
| 5,158,545 A | 10/1992 | Trudell et al. |
| 5,165,421 A | 11/1992 | Fleischhacker et al. |
| 5,263,963 A | 11/1993 | Garrison |
| 5,334,210 A | 8/1994 | Gianturco |
| 5,378,239 A | 1/1995 | Termin |
| 5,536,247 A | 7/1996 | Thornton |
| 5,562,725 A | 10/1996 | Schmitt et al. |
| 5,569,245 A | 10/1996 | Gluglielmi et al. |
| 5,578,074 A | 11/1996 | Mirigian |
| 5,591,222 A | 1/1997 | Susawa et al. |
| 5,601,595 A | 2/1997 | Smith |
| 5,630,840 A | 5/1997 | Mayer |
| D380,266 S | 6/1997 | Boatman et al. |
| 5,645,559 A | 7/1997 | Hachtman et al. |
| 5,725,552 A | 3/1998 | Kotula |
| 5,725,570 A | 3/1998 | Heath |
| 5,733,294 A | 3/1998 | Forber |
| 5,749,883 A | 5/1998 | Halpern |
| 5,759,161 A | 6/1998 | Ogawa |
| 5,766,219 A | 6/1998 | Horton |
| 5,846,261 A | 12/1998 | Kotula et al. |
| 5,873,907 A | 2/1999 | Frantzen |
| 5,907,893 A | 6/1999 | Zadno-Azizi |
| 5,916,235 A | 6/1999 | Guglielmi |
| 5,925,060 A | 7/1999 | Forber |
| 5,927,345 A | 7/1999 | Samson |
| 5,928,260 A | 7/1999 | Chin et al. |
| 5,935,148 A | 8/1999 | Villar et al. |
| 5,944,733 A | 8/1999 | Engelson |
| 5,944,738 A | 8/1999 | Amplatz |
| 5,951,599 A | 9/1999 | McCrory |
| 5,964,797 A | 10/1999 | Ho |
| 5,980,554 A | 11/1999 | Lenker et al. |
| 5,984,929 A | 11/1999 | Bashiri et al. |
| 5,989,242 A | 11/1999 | Saadat et al. |
| 6,033,423 A | 3/2000 | Ken et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,123,715 A | 9/2000 | Amplatz |
| 6,139,564 A | 10/2000 | Teoh et al. |
| 6,142,975 A | 11/2000 | Jalisi et al. |
| 6,152,144 A | 11/2000 | Lesh et al. |
| 6,156,061 A | 12/2000 | Wallace et al. |
| 6,159,206 A | 12/2000 | Ogawa |
| 6,168,615 B1 | 1/2001 | Ken et al. |
| 6,168,618 B1 | 1/2001 | Frantzen |
| 6,168,622 B1 | 1/2001 | Mazzocchi |
| 6,190,402 B1 | 2/2001 | Horton et al. |
| 6,193,708 B1 | 2/2001 | Ken et al. |
| 6,203,779 B1 | 3/2001 | Ricci et al. |
| 6,221,086 B1 | 4/2001 | Forber |
| 6,238,403 B1 | 5/2001 | Greene, Jr. et al. |
| 6,277,126 B1 | 8/2001 | Barry et al. |
| 6,290,721 B1 | 9/2001 | Heath |
| 6,315,709 B1 | 11/2001 | Garibaldi et al. |
| 6,325,815 B1 | 12/2001 | Kusleika |
| 6,342,068 B1 | 1/2002 | Thompson |
| 6,344,048 B1 | 2/2002 | Chin et al. |
| 6,346,117 B1 | 2/2002 | Greenhalgh |
| 6,350,270 B1 | 2/2002 | Roue |
| 6,368,338 B1 | 4/2002 | Konya |
| 6,368,339 B1 | 4/2002 | Amplatz |
| 6,375,668 B1 | 4/2002 | Gifford |
| 6,375,670 B1 | 4/2002 | Greenhalgh |
| 6,383,174 B1 | 5/2002 | Eder |
| 6,391,037 B1 | 5/2002 | Greenhalgh |
| 6,425,914 B1 | 7/2002 | Wallace et al. |
| 6,428,558 B1 | 8/2002 | Jones et al. |
| 6,447,531 B1 | 9/2002 | Amplatz |
| 6,454,780 B1 | 9/2002 | Wallace |
| 6,461,370 B1 | 10/2002 | Gray et al. |
| 6,463,317 B1 | 10/2002 | Kucharczyk |
| 6,468,266 B1 | 10/2002 | Bashiri et al. |
| 6,478,773 B1 | 11/2002 | Gandhi et al. |
| 6,500,149 B2 | 12/2002 | Gandhi et al. |
| 6,506,204 B2 | 1/2003 | Mazzocchi |
| 6,511,468 B1 | 1/2003 | Cragg et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,539 B1 | 8/2003 | Hayashi et al. |
| 6,613,074 B1 | 9/2003 | Mitelberg |
| 6,626,939 B1 | 9/2003 | Burnside et al. |
| 6,632,241 B1 | 10/2003 | Hancock |
| 6,635,068 B1 | 10/2003 | Dubrul et al. |
| 6,638,257 B2 | 10/2003 | Amplatz |
| 6,652,556 B1 | 11/2003 | Van Tassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,150 B1 | 2/2004 | Van Tassel |
| 6,689,486 B2 | 2/2004 | Ho et al. |
| 6,719,778 B1 | 4/2004 | Van Tassel et al. |
| 6,730,119 B1 | 5/2004 | Smalling |
| 6,743,236 B2 | 6/2004 | Barry et al. |
| 6,743,251 B1 | 6/2004 | Eder |
| 6,746,468 B1 | 6/2004 | Sepetka et al. |
| 6,746,890 B2 | 6/2004 | Gupta et al. |
| 6,752,826 B2 | 6/2004 | Holloway et al. |
| 6,780,196 B2 | 8/2004 | Chin et al. |

(56) References Cited

U.S. PATENT DOCUMENTS

| | | | |
|---|---|---|---|
| 6,811,560 B2 | 11/2004 | Jones et al. |
| 6,818,006 B2 | 11/2004 | Douk et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,936,055 B1 | 8/2005 | Ken et al. |
| 6,940,209 B2 | 9/2005 | Henderson |
| 6,953,472 B2 | 10/2005 | Palmer et al. |
| 6,953,473 B2 | 10/2005 | Porter |
| 6,966,892 B2 | 11/2005 | Gandhi et al. |
| 6,994,092 B2 | 2/2006 | van der Burg et al. |
| 7,001,409 B2 | 2/2006 | Amplatz |
| 7,004,962 B2 | 2/2006 | Stinson |
| 7,011,671 B2 | 3/2006 | Welch |
| 7,044,958 B2 | 5/2006 | Douk et al. |
| 7,052,513 B2 | 5/2006 | Thompson |
| 7,083,632 B2 | 8/2006 | Avellanet et al. |
| 7,101,390 B2 | 9/2006 | Nelson |
| 7,122,043 B2 | 10/2006 | Greenhalgh et al. |
| 7,128,736 B1 | 10/2006 | Abrams et al. |
| 7,179,276 B2 | 2/2007 | Barry et al. |
| 7,182,774 B2 | 2/2007 | Barry et al. |
| 7,195,636 B2 | 3/2007 | Avellanet et al. |
| 7,198,613 B2 | 4/2007 | Gandhi et al. |
| 7,201,918 B2 | 4/2007 | Cruise |
| 7,229,454 B2 | 6/2007 | Tran |
| 7,229,461 B2 | 7/2007 | Chin et al. |
| 7,275,471 B2 | 10/2007 | Nishri et al. |
| 7,326,225 B2 | 2/2008 | Ferrera et al. |
| 7,329,279 B2 | 2/2008 | Haug et al. |
| 7,331,980 B2 | 2/2008 | Dubrul |
| 7,410,482 B2 | 8/2008 | Murphy |
| 7,419,503 B2 | 9/2008 | Pulnev et al. |
| 7,490,396 B2 | 2/2009 | Bradley |
| 7,524,319 B2 | 4/2009 | Dubrul |
| 7,569,066 B2 | 8/2009 | Gerberding |
| 7,573,382 B2 | 8/2009 | Choubey et al. |
| 7,575,582 B2 | 8/2009 | Gandhi et al. |
| 7,578,826 B2 | 8/2009 | Gandhi et al. |
| 7,597,704 B2 | 10/2009 | Frazier et al. |
| 7,648,532 B2 | 1/2010 | Greenhalgh et al. |
| 7,695,488 B2 | 4/2010 | Berenstein |
| 7,722,637 B2 | 5/2010 | Barry et al. |
| 7,745,732 B2 | 6/2010 | Michael et al. |
| 7,806,919 B2 | 10/2010 | Bloom et al. |
| 7,862,577 B2 | 1/2011 | Gray et al. |
| 7,942,925 B2 | 5/2011 | Yodaf |
| 7,989,703 B2 | 8/2011 | Schaffer |
| 8,043,326 B2 | 10/2011 | Hancock |
| 8,043,329 B2 | 10/2011 | Khairkhahan |
| 8,066,757 B2 | 11/2011 | Ferrera et al. |
| 8,142,456 B2 | 3/2012 | Rosqueta et al. |
| 8,182,506 B2 | 5/2012 | Fitz et al. |
| 8,192,480 B2 | 6/2012 | Tieu et al. |
| 8,261,648 B1 | 9/2012 | Marchand et al. |
| 8,313,505 B2 | 11/2012 | Amplatz et al. |
| 8,398,670 B2 | 3/2013 | Amplatz |
| 8,430,012 B1 | 4/2013 | Marchand |
| 8,506,619 B2 | 8/2013 | Ortiz et al. |
| 8,551,132 B2 | 10/2013 | Eskridge et al. |
| 8,597,320 B2 | 12/2013 | Sepetka |
| 8,597,323 B1 | 12/2013 | Plaza et al. |
| 8,690,907 B1 | 4/2014 | Janardhan et al. |
| 8,715,338 B2 | 5/2014 | Frid |
| 8,728,117 B1 | 5/2014 | Janardhan et al. |
| 8,747,430 B2 | 6/2014 | Porter et al. |
| 8,758,395 B2 | 6/2014 | Kleshinski et al. |
| 8,795,330 B2 | 8/2014 | Janardhan et al. |
| 8,826,791 B2 | 9/2014 | Thompson et al. |
| 8,840,735 B2 | 9/2014 | Schaffer |
| 8,845,679 B1 | 9/2014 | Janardhan et al. |
| 9,078,658 B2 | 7/2015 | Hewitt et al. |
| 9,161,758 B2 | 10/2015 | Figulla et al. |
| 9,198,668 B2 | 12/2015 | Theobald et al. |
| 9,198,670 B2 | 12/2015 | Hewitt et al. |
| 9,259,337 B2 | 2/2016 | Cox et al. |
| 9,272,323 B2 | 3/2016 | Schaffer |
| 9,295,473 B2 | 3/2016 | Hewitt et al. |
| 9,351,715 B2 | 5/2016 | Mach |
| 9,492,174 B2 | 11/2016 | Hewitt et al. |
| 9,504,588 B2 | 11/2016 | Sadisivan et al. |
| 9,585,669 B2 | 3/2017 | Becking et al. |
| 9,597,087 B2 | 3/2017 | Marchand et al. |
| 9,629,635 B2 | 4/2017 | Hewitt et al. |
| 9,687,245 B2 | 6/2017 | Molaei et al. |
| 9,855,047 B2 | 1/2018 | Berez et al. |
| 9,955,976 B2 | 5/2018 | Hewitt et al. |
| 10,123,803 B2 | 11/2018 | Ferrera et al. |
| 10,130,372 B2 | 11/2018 | Griffin |
| 10,136,896 B2 | 11/2018 | Hewitt et al. |
| 10,238,393 B2 | 3/2019 | Marchand et al. |
| 10,260,182 B2 | 4/2019 | Thompson et al. |
| 10,260,183 B2 | 4/2019 | Marchand et al. |
| 10,398,441 B2 | 9/2019 | Warner et al. |
| 10,426,589 B2 | 10/2019 | Van der Burg et al. |
| 10,470,773 B2 | 11/2019 | Maguire et al. |
| 10,617,426 B2 | 4/2020 | Aboytes et al. |
| 10,716,573 B2 | 7/2020 | Connor |
| 10,736,758 B2 | 8/2020 | Ruvalcaba et al. |
| 10,813,645 B2 | 10/2020 | Hewitt et al. |
| 10,856,880 B1 | 12/2020 | Badruddin et al. |
| 10,939,914 B2 | 3/2021 | Hewitt et al. |
| 10,952,739 B2 | 3/2021 | Plaza et al. |
| 11,033,277 B2 | 6/2021 | Wolfe et al. |
| 11,058,431 B2 | 7/2021 | Pereira et al. |
| 11,185,335 B2 | 11/2021 | Badruddin et al. |
| 11,202,636 B2 | 12/2021 | Zaidat et al. |
| 11,284,901 B2 | 3/2022 | Griffin |
| 11,317,921 B2 | 5/2022 | Hewitt et al. |
| 11,389,174 B2 | 7/2022 | Griffin |
| 11,464,518 B2 | 10/2022 | Connor |
| 11,559,309 B2 | 1/2023 | Rangwala et al. |
| 11,723,667 B2 * | 8/2023 | Hewitt ............. A61B 17/12113 606/200 |
| 11,786,253 B2 | 10/2023 | Divino et al. |
| 2001/0031981 A1 | 10/2001 | Evans et al. |
| 2002/0065552 A1 | 5/2002 | Jayaraman et al. |
| 2002/0103542 A1 | 8/2002 | Bilbo |
| 2002/0111647 A1 | 8/2002 | Khairkhahan et al. |
| 2002/0143349 A1 | 10/2002 | Gifford, III et al. |
| 2002/0143361 A1 | 10/2002 | Douk et al. |
| 2002/0156499 A1 | 10/2002 | Konya et al. |
| 2002/0169473 A1 | 11/2002 | Sepetka et al. |
| 2002/0183787 A1 | 12/2002 | Wahr et al. |
| 2002/0187288 A1 | 12/2002 | Lim et al. |
| 2003/0012816 A1 | 1/2003 | West et al. |
| 2003/0028209 A1 | 2/2003 | Teoh et al. |
| 2003/0040771 A1 | 2/2003 | Hyodoh et al. |
| 2003/0167068 A1 | 9/2003 | Amplatz |
| 2003/0171739 A1 | 9/2003 | Murphy et al. |
| 2003/0171774 A1 | 9/2003 | Freudenthal et al. |
| 2003/0181942 A1 | 9/2003 | Sutton et al. |
| 2003/0187473 A1 | 10/2003 | Berenstein et al. |
| 2003/0199913 A1 | 10/2003 | Dubrul et al. |
| 2004/0059370 A1 | 3/2004 | Green, Jr. et al. |
| 2004/0098027 A1 | 5/2004 | Tech et al. |
| 2004/0111147 A1 | 6/2004 | Rabkin et al. |
| 2004/0122367 A1 | 6/2004 | Sculati et al. |
| 2004/0143239 A1 | 7/2004 | Zhou et al. |
| 2004/0158311 A1 | 8/2004 | Berhow |
| 2004/0172053 A1 | 9/2004 | Barry et al. |
| 2004/0186562 A1 | 9/2004 | Cox |
| 2004/0193206 A1 | 9/2004 | Gerberding et al. |
| 2004/0193208 A1 | 9/2004 | Talpade et al. |
| 2004/0220563 A1 | 11/2004 | Eder |
| 2004/0260333 A1 | 12/2004 | Dubrul et al. |
| 2005/0021075 A1 | 1/2005 | Bonnette et al. |
| 2005/0033408 A1 | 2/2005 | Jones et al. |
| 2005/0053782 A1 | 3/2005 | Sen et al. |
| 2005/0096728 A1 | 5/2005 | Ramer |
| 2005/0112349 A1 | 5/2005 | Laurencin et al. |
| 2005/0113861 A1 | 5/2005 | Corcoran et al. |
| 2005/0113868 A1 | 5/2005 | Devellian et al. |
| 2005/0119684 A1 | 6/2005 | Gutterman et al. |

(56) References Cited

U.S. PATENT DOCUMENTS

| | | |
|---|---|---|
| 2005/0133046 A1 | 6/2005 | Becker et al. |
| 2005/0137623 A1 | 6/2005 | Jones et al. |
| 2005/0149173 A1 | 7/2005 | Hunter et al. |
| 2005/0216052 A1 | 9/2005 | Mazzocchi et al. |
| 2005/0222489 A1 | 10/2005 | Rahdert et al. |
| 2005/0228422 A1 | 10/2005 | Machold et al. |
| 2005/0228434 A1 | 10/2005 | Amplatz et al. |
| 2005/0267516 A1 | 12/2005 | Soleimani et al. |
| 2005/0277978 A1 | 12/2005 | Greenhalgh |
| 2006/0009798 A1 | 1/2006 | Callister et al. |
| 2006/0009799 A1 | 1/2006 | Kleshinski et al. |
| 2006/0009800 A1 | 1/2006 | Christianson et al. |
| 2006/0052815 A1 | 3/2006 | Fitz et al. |
| 2006/0052816 A1 | 3/2006 | Bates et al. |
| 2006/0064151 A1 | 3/2006 | Guterman et al. |
| 2006/0083721 A1 | 4/2006 | Cohen et al. |
| 2006/0106421 A1 | 5/2006 | Teoh |
| 2006/0116708 A1 | 6/2006 | Ogawa et al. |
| 2006/0135947 A1 | 6/2006 | Soltesz et al. |
| 2006/0155323 A1 | 7/2006 | Porter et al. |
| 2006/0178694 A1 | 8/2006 | Greenhalgh et al. |
| 2006/0200192 A1 | 9/2006 | Fitz et al. |
| 2006/0200234 A1 | 9/2006 | Hines |
| 2006/0212055 A1 | 9/2006 | Karabey et al. |
| 2006/0217799 A1 | 9/2006 | Mailander et al. |
| 2006/0235464 A1 | 10/2006 | Avellanet et al. |
| 2006/0247680 A1 | 11/2006 | Amplatz et al. |
| 2006/0252984 A1 | 11/2006 | Rahdert et al. |
| 2006/0253149 A1 | 11/2006 | Gandhi et al. |
| 2006/0271086 A1 | 11/2006 | Ramzipoor et al. |
| 2007/0021816 A1 | 1/2007 | Rudin |
| 2007/0031584 A1 | 2/2007 | Roth |
| 2007/0061006 A1 | 3/2007 | Desatnik et al. |
| 2007/0088387 A1 | 4/2007 | Eskridge et al. |
| 2007/0100419 A1 | 5/2007 | Licata et al. |
| 2007/0106311 A1 | 5/2007 | Wallace et al. |
| 2007/0106323 A1 | 5/2007 | Barry et al. |
| 2007/0112380 A1 | 5/2007 | Figulla et al. |
| 2007/0142906 A1 | 6/2007 | Figulla et al. |
| 2007/0144124 A1 | 6/2007 | Schewe et al. |
| 2007/0167911 A1 | 7/2007 | Gandhi et al. |
| 2007/0167980 A1 | 7/2007 | Figulla et al. |
| 2007/0173928 A1 | 7/2007 | Morsi |
| 2007/0203062 A1 | 8/2007 | Ellis-Behnke et al. |
| 2007/0208373 A1 | 9/2007 | Zaver et al. |
| 2007/0208376 A1 | 9/2007 | Meng |
| 2007/0225760 A1 | 9/2007 | Moszner et al. |
| 2007/0233186 A1 | 10/2007 | Meng |
| 2007/0255388 A1 | 11/2007 | Rudakov et al. |
| 2007/0265656 A1 | 11/2007 | Amplatz et al. |
| 2007/0288083 A1 | 12/2007 | Hines |
| 2007/0299464 A1 | 12/2007 | Cruise et al. |
| 2008/0033341 A1 | 2/2008 | Grad |
| 2008/0033366 A1 | 2/2008 | Matson |
| 2008/0033475 A1 | 2/2008 | Meng |
| 2008/0033478 A1 | 2/2008 | Meng |
| 2008/0097495 A1 | 4/2008 | Feller, III et al. |
| 2008/0119886 A1 | 5/2008 | Greenhalgh et al. |
| 2008/0161936 A1 | 7/2008 | Feller et al. |
| 2008/0188923 A1 | 8/2008 | Chu |
| 2008/0195139 A1 | 8/2008 | Donald et al. |
| 2008/0200945 A1 | 8/2008 | Amplatz et al. |
| 2008/0221600 A1 | 9/2008 | Dieck et al. |
| 2008/0228215 A1 | 9/2008 | Strauss et al. |
| 2008/0281350 A1 | 11/2008 | Sepetka et al. |
| 2009/0025820 A1 | 1/2009 | Adams |
| 2009/0062812 A1 | 3/2009 | Fitz et al. |
| 2009/0062834 A1 | 3/2009 | Moftakhar |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112305 A1 | 4/2009 | Goldmann et al. |
| 2009/0132024 A1 | 5/2009 | Berkhoff |
| 2009/0163780 A1 | 6/2009 | Tieu |
| 2009/0227976 A1 | 9/2009 | Calabria |
| 2009/0275974 A1 | 11/2009 | Marchand |
| 2009/0287291 A1 | 11/2009 | Becking et al. |
| 2009/0287294 A1 | 11/2009 | Rosqueta et al. |
| 2009/0318948 A1 | 12/2009 | Linder et al. |
| 2010/0004679 A1 | 1/2010 | Osypka |
| 2010/0023048 A1 | 1/2010 | Mach |
| 2010/0023105 A1 | 1/2010 | Levy et al. |
| 2010/0069948 A1 | 3/2010 | Veznedaroglu et al. |
| 2010/0094409 A1 | 4/2010 | Barker et al. |
| 2010/0106235 A1 | 4/2010 | Kariniemi et al. |
| 2010/0262182 A1 | 10/2010 | Moszner et al. |
| 2011/0022149 A1 | 1/2011 | Cox |
| 2011/0029008 A1 | 2/2011 | Gesswein |
| 2011/0046658 A1 | 2/2011 | Connor et al. |
| 2011/0046719 A1 | 2/2011 | Frid |
| 2011/0054515 A1 | 3/2011 | Bridgeman |
| 2011/0082493 A1 | 4/2011 | Samson et al. |
| 2011/0144669 A1 | 6/2011 | Becking et al. |
| 2011/0152823 A1 | 6/2011 | Mohiuddin et al. |
| 2011/0152993 A1 | 6/2011 | Marchand et al. |
| 2011/0202085 A1 | 8/2011 | Loganathan et al. |
| 2011/0208227 A1 | 8/2011 | Becking |
| 2011/0208233 A1 | 8/2011 | McGuckin |
| 2011/0224776 A1 | 9/2011 | Sepekta et al. |
| 2011/0295298 A1 | 12/2011 | Moszner |
| 2011/0319926 A1 | 12/2011 | Becking |
| 2012/0065667 A1 | 3/2012 | Javois et al. |
| 2012/0143237 A1 | 6/2012 | Cam |
| 2012/0165919 A1 | 6/2012 | Cox et al. |
| 2012/0197283 A1 | 8/2012 | Marchand et al. |
| 2012/0271337 A1 | 10/2012 | Figulla et al. |
| 2012/0283768 A1 | 11/2012 | Cox et al. |
| 2012/0330341 A1 | 12/2012 | Becking et al. |
| 2013/0066357 A1 | 3/2013 | Aboytes et al. |
| 2013/0092012 A1 | 4/2013 | Marchand et al. |
| 2013/0116722 A1 | 5/2013 | Aboytes et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0296912 A1 | 11/2013 | Ottma |
| 2013/0325051 A1 | 12/2013 | Martin et al. |
| 2014/0005713 A1 | 1/2014 | Bowman et al. |
| 2014/0005714 A1 | 1/2014 | Quick et al. |
| 2014/0018841 A1 | 1/2014 | Peiffer et al. |
| 2014/0052233 A1 | 2/2014 | Cox et al. |
| 2014/0058436 A1 | 2/2014 | Rosenbluth et al. |
| 2014/0074151 A1 | 3/2014 | Tischler et al. |
| 2014/0135734 A1 | 5/2014 | Dakin et al. |
| 2014/0135817 A1 | 5/2014 | Tischler et al. |
| 2014/0135827 A1 | 5/2014 | Amplatz et al. |
| 2014/0142611 A1 | 5/2014 | Plaza et al. |
| 2014/0172001 A1 | 6/2014 | Becking et al. |
| 2014/0200607 A1 | 7/2014 | Sepetka et al. |
| 2014/0257360 A1 | 9/2014 | Keillor |
| 2014/0257361 A1 | 9/2014 | Prom |
| 2014/0318354 A1 | 10/2014 | Thompson et al. |
| 2014/0318355 A1 | 10/2014 | Marchand et al. |
| 2014/0330299 A1 | 11/2014 | Rosenbluth et al. |
| 2014/0358178 A1 | 12/2014 | Hewitt et al. |
| 2015/0012033 A1 | 1/2015 | Plaza et al. |
| 2015/0133989 A1 | 5/2015 | Lubock et al. |
| 2015/0182674 A1 | 7/2015 | Schaffer |
| 2015/0272589 A1 | 10/2015 | Lorenzo |
| 2015/0283363 A1 | 10/2015 | Hewitt et al. |
| 2015/0313605 A1 | 11/2015 | Griffin |
| 2015/0374483 A1 | 12/2015 | Janardhan et al. |
| 2016/0015396 A1 | 1/2016 | Cox et al. |
| 2016/0015398 A1 | 1/2016 | Hewitt et al. |
| 2016/0030052 A1 | 2/2016 | Cragg et al. |
| 2016/0045201 A1 | 2/2016 | Rosenbluth et al. |
| 2016/0100842 A1 | 4/2016 | Plaza et al. |
| 2016/0192941 A1 | 7/2016 | Hewitt et al. |

(56) References Cited

U.S. PATENT DOCUMENTS

| | | |
|---|---|---|
| 2016/0249934 A1 | 9/2016 | Hewitt et al. |
| 2016/0249935 A1 | 9/2016 | Hewitt et al. |
| 2016/0249937 A1 | 9/2016 | Marchand et al. |
| 2016/0262769 A1 | 9/2016 | Cragg et al. |
| 2016/0324528 A1 | 11/2016 | Hebert et al. |
| 2016/0324668 A1 | 11/2016 | Wallace et al. |
| 2016/0335757 A1 | 11/2016 | Florent et al. |
| 2016/0367260 A9 | 12/2016 | Hewitt et al. |
| 2017/0035437 A1 | 2/2017 | Sarge et al. |
| 2017/0079662 A1 | 3/2017 | Rhee et al. |
| 2017/0095254 A1 | 4/2017 | Hewitt et al. |
| 2017/0128077 A1 | 5/2017 | Hewitt et al. |
| 2017/0224350 A1 | 8/2017 | Shimizu et al. |
| 2017/0245862 A1 | 8/2017 | Cox et al. |
| 2017/0258473 A1 | 9/2017 | Plaza et al. |
| 2018/0000489 A1 | 1/2018 | Marchand et al. |
| 2018/0070955 A1 | 3/2018 | Greene, Jr. et al. |
| 2018/0140305 A1 | 5/2018 | Connor |
| 2018/0153554 A1 | 6/2018 | Walzman |
| 2018/0185130 A1 | 7/2018 | Janardhan et al. |
| 2018/0206849 A1 | 7/2018 | Hewitt et al. |
| 2018/0206851 A1 | 7/2018 | Walzman |
| 2018/0271540 A1 | 9/2018 | Merritt et al. |
| 2018/0303486 A1 | 10/2018 | Rosenbluth et al. |
| 2018/0338767 A1 | 11/2018 | Dasnurkar et al. |
| 2019/0046209 A1 | 2/2019 | Plaza et al. |
| 2019/0059909 A1 | 2/2019 | Griffin |
| 2019/0192166 A1 | 6/2019 | Hewitt et al. |
| 2019/0192167 A1 | 6/2019 | Lorenzo |
| 2019/0209180 A1 | 7/2019 | Kealey et al. |
| 2019/0218696 A1 | 7/2019 | Thompson et al. |
| 2019/0223876 A1 | 7/2019 | Badruddin et al. |
| 2019/0223878 A1 | 7/2019 | Lorenzo et al. |
| 2019/0223881 A1 | 7/2019 | Hewitt et al. |
| 2019/0269414 A1 | 9/2019 | Griffin |
| 2019/0290286 A1 | 9/2019 | Divino et al. |
| 2019/0298364 A1 | 10/2019 | Walsh et al. |
| 2019/0343533 A1 | 11/2019 | Costalat |
| 2019/0365385 A1 | 12/2019 | Gorochow et al. |
| 2020/0038035 A1 | 2/2020 | Griffin |
| 2020/0113576 A1 | 4/2020 | Gorochow et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2020/0367894 A1 | 11/2020 | Pereira et al. |
| 2020/0367898 A1 | 11/2020 | Gorochow et al. |
| 2021/0007754 A1 | 1/2021 | Milhous et al. |
| 2021/0128165 A1 | 5/2021 | Pulugurtha et al. |
| 2021/0153871 A1 | 5/2021 | Griffin |
| 2021/0275184 A1 | 9/2021 | Hewitt et al. |
| 2022/0192678 A1 | 6/2022 | Hewitt et al. |
| 2022/0257260 A1 | 8/2022 | Hewitt et al. |
| 2022/0323084 A1 | 10/2022 | Griffin |

FOREIGN PATENT DOCUMENTS

| | | |
|---|---|---|
| CN | 106974691 | 7/2017 |
| EP | 0706876 | 7/2000 |
| EP | 0808138 | 5/2005 |
| EP | 1576929 | 9/2005 |
| EP | 1844717 | 10/2007 |
| EP | 1923019 | 5/2008 |
| EP | 2055263 | 6/2009 |
| EP | 2258275 | 12/2011 |
| EP | 2596754 A1 | 5/2013 |
| EP | 2157937 | 3/2017 |
| FR | 2333169 | 6/1997 |
| JP | 52141092 | 11/1977 |
| JP | H4-47415 | 4/1992 |
| WO | WO 95/30384 | 11/1995 |
| WO | WO 96/01591 | 1/1996 |
| WO | WO 97/26939 | 7/1997 |
| WO | WO 99/03404 | 1/1999 |
| WO | WO 99/05977 | 2/1999 |
| WO | WO 99/62432 | 12/1999 |
| WO | WO 01/45571 | 6/2001 |
| WO | WO 01/93782 | 12/2001 |
| WO | WO 02/00139 | 1/2002 |
| WO | WO 03/011151 | 2/2003 |
| WO | WO 03/032818 | 4/2003 |
| WO | WO 03/063732 | 8/2003 |
| WO | WO 2004/047649 | 6/2004 |
| WO | WO 2004/093742 | 11/2004 |
| WO | WO 2005/117718 | 12/2005 |
| WO | WO 2006/026744 | 3/2006 |
| WO | WO 2006/055683 | 5/2006 |
| WO | WO 2007/006139 | 1/2007 |
| WO | WO 2007/096183 | 8/2007 |
| WO | WO 2008/151204 | 12/2008 |
| WO | WO 2009/036219 | 3/2009 |
| WO | WO 2009/048700 A1 | 4/2009 |
| WO | WO 2009/121006 | 10/2009 |
| WO | WO 2009/126747 | 10/2009 |
| WO | WO 2009/132045 | 10/2009 |
| WO | WO 2009/134337 | 11/2009 |
| WO | WO 2009/135166 | 11/2009 |
| WO | WO 2010/134914 | 11/2010 |
| WO | WO 2011/057002 | 5/2011 |
| WO | WO 2013/102848 | 7/2013 |
| WO | WO 2013/119332 A2 | 8/2013 |
| WO | WO 2014/087245 | 6/2014 |
| WO | WO 2014/169261 | 10/2014 |
| WO | WO 2015/160721 | 10/2015 |
| WO | WO 2015/171268 | 11/2015 |
| WO | WO 2015/192019 | 12/2015 |
| WO | WO 2017/153603 | 9/2017 |
| WO | WO 2018/051187 | 3/2018 |
| WO | WO 2018/058033 A1 | 3/2018 |
| WO | WO 2019/040494 | 2/2019 |

OTHER PUBLICATIONS

Allen et al., "Micromachine Wedge Stepping Motor," pp. 1-6, Nov. 12-20, 1998 ASME International Mechanical Engineering Congress, Anaheim, CA.

Altes et al., "Creation of Saccular Aneurysms in the Rabbit: A model Suitable for Testing Endovascular Devices," American Roentgen Ray Society, Feb. 2000.

Ansari et al., "Thrombosis of a Fusiform Intracranial Aneurysm Induced by Overlapping Neuroform Stents: Case Report," *Neurosurgery*, E950-E951 vol. 60, No. 5, May 2007.

Atritech Press Release, Minneapolis, Jun. 18, 2007 "Atritech Announces Intellectual Property Acquisition, Transaction Establishes Company as leader in Left Atrial Appendage Market."

Caroff, J. et al., "Woven Endobridge (WEB) Device for endovascular treatment of ruptured intracranial wide-neck aneurysms: a single-center experience," *Neuroradiology*, 56(9):755-761 (Sep. 2014).

Caroff, J. et al., "Role of C-Arm VasoCT in the Use of Endovascular WEB Flow Disruption in Intracranial Aneurysm Treatment," *AJNR Am. J. Neuroradiol.* 35(7):1353-1357 (Jul. 2014).

Colla, R. et al., "Treatment of Wide-Neck Basilar Tip Aneurysms Using the Web II Device," *The Neuroradiology Journal* 26(6):669-677 (Dec. 2013).

De Backer, O. et al., "Percutaneous left atrial appendage occlusion for stroke prevention in atrial fibrillation: an update," *Open Heart*, 4:1-14 (2013).

Ding, Y.H. et al., "The Woven EndoBridge: A New Aneurysm Occlusion Device," *AJNR Am. J. Neruradiol.* 32:607-611 (Mar. 2011).

Duerig, T.W., "The Use of Superelasticity in Modern Medicine," MRS Bulletin, pp. 101-104 (Feb. 2002).

Fiorella, D. et al., "Interobserver variability in the assessment of aneurysm occlusion with the WEB aneurysm embolization system," *J. NeuroIntervent. Surg.* Jul. 1, 2014, pii: neurintsurg-2014-011251. doi: 10.1136/neurintsurg-2014-011251 [Epub ahead of print].

Fort Wayne Metals HHS Tube brochure, p. 28-29 (2009), Fort Wayne, Indiana, www.oldsite.fwmetals.com.

Grabenwoger et al., "Endothelialization of Biosynthetic vascular Prosthesis After Laser Perforation," *Ann Thorac Surg*, 66:S110-S114 (1998).

(56) References Cited

OTHER PUBLICATIONS

Guider Softip XF Guide Catheters Brochure, Boston Scientific Corporation 2004.
Gupta et al., "Nitinol Thin Film Three Dimensional Devices—Fabrication and Applications," From: SMST—2003: Proceedings of the International Conference on Shape Memory and Superelastic Technologies Published: 2004.
Hill et al., "Initial Results of the Amplatzer® Vascular Plug in the treatment of Congenital Heart Disease," Technology and Services, *Business Briefing: US Cardiology*, pp. 1-3 (2004).
Jeffree et al., "The Porus, Guidewire-Directed, Detachable Aneurysm Liner: A New Concept in the Endovascular Treatment of Intracranial Aneurysms," *AJNR Am J Neuradiol* 20:774-779 (May 1999).
Kallmes et al., "A New Endoluminal, Flow-Disrupting Device for Treatment of Saccular Eneurysms," *Stroke*, Journal of the American Heart Association 38:1-7 (2007).
Klisch, J. et al., "The Woven EndoBridge Cerebral Aneurysm Embolization Device (WEB II): initial clinical experience," *Neuroradiology* 53:599-607 (2011).
Kónya, A. et al., "Preliminary Results with a New Vascular Basket Occluder in Swine," JVIR, 10(8):1043-1049 (1999).
Kwon et al., "Preliminary Results of the Luna Aneurysm Embolization System in a Rabbit Model: A New Intrasaccular Aneurysm Occlusion Device," *AJNR Am J Neuroradiol*, 32:602-606 (Mar. 2011).
Lendlein, A. et al., "Shape-Memory Polymers," *Angew. Chem. Int. Ed.*, 41:2034-2057 (2002).
Lendlein, A. et al., "Biodegradable, Elastic Shape-Memory Polymers for Potential Biomedical Applications," *Science* 296:1673-1676 (May 31, 2002).
Lieber, B.B. et al., "The Role of Blood Impulse in Cerebral Aneurysm Coil Compaction: Effect of Aneurysm Neck Size," IMECE2003-43099, Proceedings of IMECE '03, 2003 ASME International Mechanical Engineering Congress, Washington, D.C. (Nov. 15-21, 2003).
Liu, C. et al., "Review of progress in shape-memory polymers," *J. Mater. Chem.* 17:1543-1558 (2007).
Lubicz, B. et al., "WEB Device for Endovascular Treatment of Wide-Neck Bifurcation Aneurysms," *AJNR Am. J. Neuroradiol.* 34(6):1209-1214 (Jun.-Jul. 2013).
Lubicz, B. et al., "WEB-DL Endovascular Treatment of Wide-Neck Bifurcation Aneurysms: Short- and Midterm Results in a European Study," *AJNR Am. J. Neuroradiol.* 35(3):432-438 (Mar. 2014). doi: 10.3174/ajnr.A3869. Epub Jan. 23, 2014.
Major, S. et al., "Life of Nitinol Drawn Filed Wires with Ag or Au Core for Medical Application," *International Journal of Mechanics* 2(7):73-80 (2013).
Matinlinna et al., "An Introduction to Silanes and Their Clinical Applications in Dentistry," *The International Journal of Prosthodontics*, 17(2):155-164 (2004).
Mine et al., "Intrasaccular flow-diversion for treatment of intracranial aneurysms: the Woven EndoBridge," *Expert Rev. Med. Devices* 11(3): 315-325 (May 2014). doi: 10.1586/17434440.2014.907741. Epub Apr. 2, 2014.
Nakayama et al., "Development of Microporous Covered Stents: Geometrical Design of the Luminal Surface," *The International Journal of Artificial Organs*, 28(6):600-608 (2005).
Nemat-Nasser, S. et al., "Superelastic and cyclic response of NiTi SMA at various strain rates and temperatures," *Mechanics of Materials* 38:463-474 (2006).
Nishi et al., "Embolization of experimental aneurysms using a heparin-loaded stent graft with micropores," *Cardiovascular Radiation Medicine* 4:29-33 (2003).
Nishi et al., "Occlusion of Experimental Aneurysms with Heparin-Loaded, Microporous Stent Grafts," *Neurosurgery* 53(6):1397-1405 (Dec. 2003).
Papagiannaki, C. et al., "WEB Intrasaccular Flow Disruptor—Prospective, Multicenter Experience in 83 Patients with 85 Aneurysms," *AJNR Am. J. Neuroradiol.* 35(11):2106-2111 (Nov.-Dec. 2014). 35(11):2106-11. doi: 10.3174/ajnr.A4028. Epub Jul. 3, 2014.
Park, J. et al., "Percutaneous Left Atrial Appendage Transcatheter Occlusion (PLAATO) for Stroke Prevention in Atrial Fibrillation: 2-Year Outcome," *J Invasive. Cardiol.*, 21(9):446-450 (2009).
Pelton, A.R. et al., "Optimisation of processing and properties of medical grade Nitinol wire," *Min. Invas. Ther. & Allied Technol.* 9(1):107-118 (2000).
Pham, Q. et al., "Electrospinning of Polymeric Nanofibers for Tissue Engineering Applications: A Review," *Tissue Engr* 12(5):1197-1211 (1996).
Pierot, L. et al., "Intrasaccular Flow-Disruption Treatment of Intracranial Aneurysms: Preliminary Results of a Multicenter Clinical Study," *AJNR Am J Neuroradiol.* 33(7):1232-1238 (Aug. 2012). doi: 10.3174/ajnr.A3191. Epub Jun. 7, 2012.
Pierot, L. et al., "Endovascular WEB Flow Disruption in Middle Cerebral Artery Aneurysms: Preliminary Feasibility, Clinical, and Anatomical Results in a Multicenter Study," *Neurosurgery* 73(1):27-35 (Jul. 2013).
Pierot, L. et al., "Role, safety, and efficacy of WEB flow disruption: a review," *EJMINT* Invited Review, 2014: 1419000139 (May 8, 2014).
Peirot, L. et al., "WEB Treatment of Intracranial Aneurysms: Feasiblity, Complications, and 1-Month Safety Results with the WEB DL and WEB SL/SLS in the French Observatory," *AJNR Am J Neuroradiol.* Feb. 5, 2015 [Epub ehead ofprint].
Romero, J. et al., "Left Atrial Appendage Closure Devices," Clinical Medicine Insights: Cardiology, 8:45-52 (2014).
Rottiers, W. et al., "Shape Memory Materials and their applications," in Korolev's readings: conference proceedings, pp. 250-250 (2011).
Salamat et al., "Experimental Evaluation of a New Transcatheter Vascular Embolization Device in the Swine Model," *J Vasc Interv Radiol*, 12:301-311 (2002).
Schaffer, J.E. et al., "Engineering Characteristics of Drawn Filled Nitinol Tube," SMST—2003: Proceedings of the International Conference on Shape Memory and Superelastic Technologies (ASM International), pp. 109-118 (2004).
Schmitz-Rode, T. et al., "Self-expandable spindle for transcatheter vascular occlusion: in vivo experiments. Work in progress." *Radiology* 188:95-100 (Jul. 1993).
Simgen, A. et al., "Evaluation of a newly designed flow diverter for the treatment of intracranial aneurysms in an elastase-induced aneurysm model, in New Zealand white rabbits," *Neuroradiology* 56:129-137 (2014).
Spelle, L. et al., "Letter to the Editor," *Neuroradiol J.* Jun. 2014; 27(3):369. doi: 10.15274/NRJ-2014-10048. Epub Jun. 17, 2014.
Spelle, L. et al., "CLinical Assessment of WEB device in Ruptured aneurYSms (CLARYS): 12-month angiographic results of a multicenter study", J NeuroIntervent Surg, 2022, 0:1-6.
Stoeckel, D. et al., "Self-expanding nitinol stents: material and design considerations," *Eur. Radiol.* 14:292-301 (2004).
Turk, A. et al., "Evaluation of the TriSpan Neck Bridge Device for the Treatment of Wide-Necked Aneurysms: An Experimental Study in Canines, Editorial Comment: An Experimental Study in Canines," *Stroke* 32:492-497 (Feb. 2001).
Wallner, A.K. et al., "Coiling after Treatment with the Woven EndoBridge Cerebral Aneurysm Embolization Device," *Interventional Neuroradiology* 18:208-212 (2012).
Yeow, W.L. et al., Device- and LAA-Specific Characteristics for Successful LAA Closures: Tips and Tricks, *Intervent. Cardiol. Clin.*, 3:239-254 (2014).
Zimmermann et al., "Patent Foramen Oval Closure With the SeptRx Device, Initial Experience with the First "In-Tunnel" Device," *JACC Cardiovascular Interventions* vol. 3, No. 9., 2010.
International Search Report and Written Opinion mailed Oct. 31, 2008 for International Application No. PCT/US2008/065694.
International Search Report and Written Opinion mailed Nov. 26, 2009 for International Application No. PCT/US2009/042592.
International Search Report and Written Opinion mailed Jul. 28, 2011 for International Application No. PCT/US2010/055494.
International Search Report and Written Opinion mailed Jul. 21, 2015 for International Application No. PCT/US2015/025609.

(56) References Cited

OTHER PUBLICATIONS

International Search Report and Written Opinion mailed Jan. 11, 2016 for International Application No. PCT/US2015/025613.
International Search Report and Written Opinion mailed Jun. 10, 2020 for International Application No. PCT/US2020/022275.
International Search Report and Written Opinion mailed Jun. 11, 2020 for International Application No. PCT/US2020/022364.
International Search Report and Written Opinion mailed Jun. 15, 2020 for International Application No. PCT/US2020/022319.
International Search Report and Written Opinion mailed Jul. 24, 2020 for International Application No. PCT/US2020/022096.
Extended European Search Report dated Apr. 25, 2014, in EP Appl No. EP 08770070.4 filed Jun. 3, 2008.
Extended European Search Report dated Jul. 30, 2014, in EP Appl No. EP 10829110 filed Nov. 4, 2010.
Extended European Search Report dated Dec. 13, 2017, in EP Appl No. EP 15789225.8 filed Jun. 5, 2015.
Official Action dated Mar. 8, 2019, in JP Appl. No. 2016-562549 filed Jun. 5, 2015.
JP, 2022-169903 Final Office Action, Mar. 12, 2024.
WO, PCT/US2022/048938 ISR and Written Opinion, Feb. 28, 2023.

\* cited by examiner

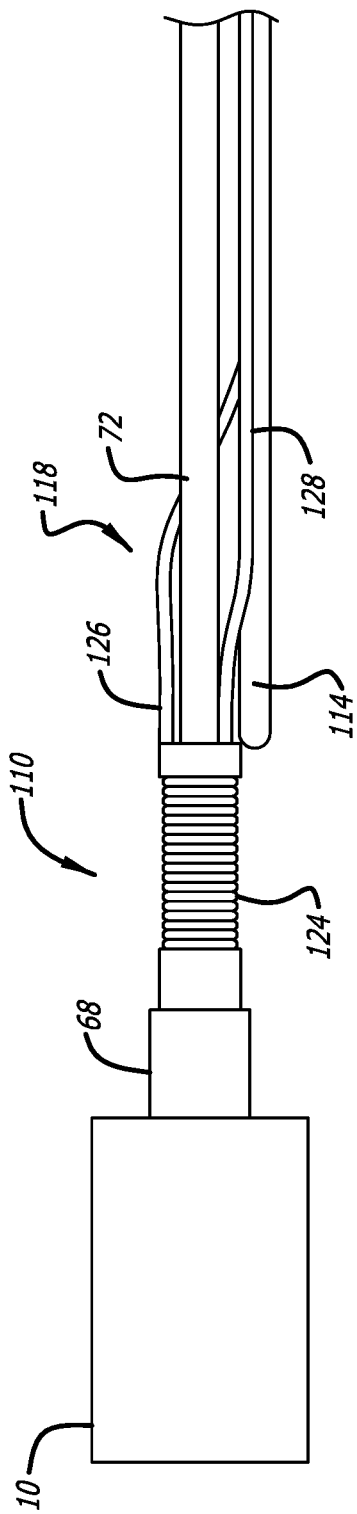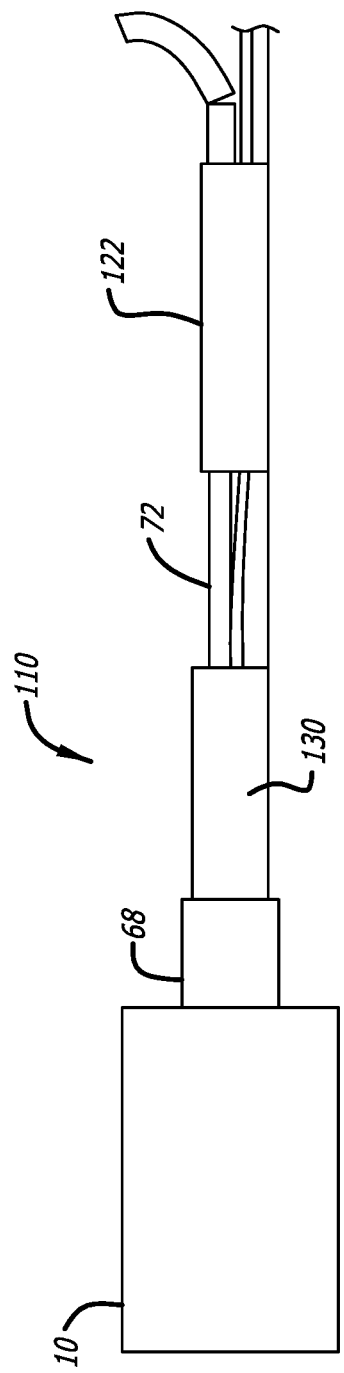

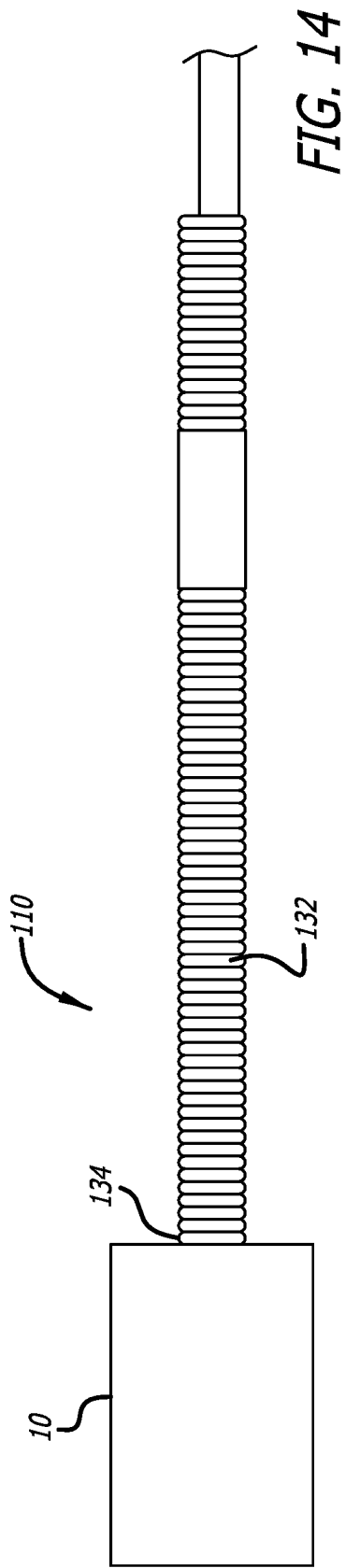
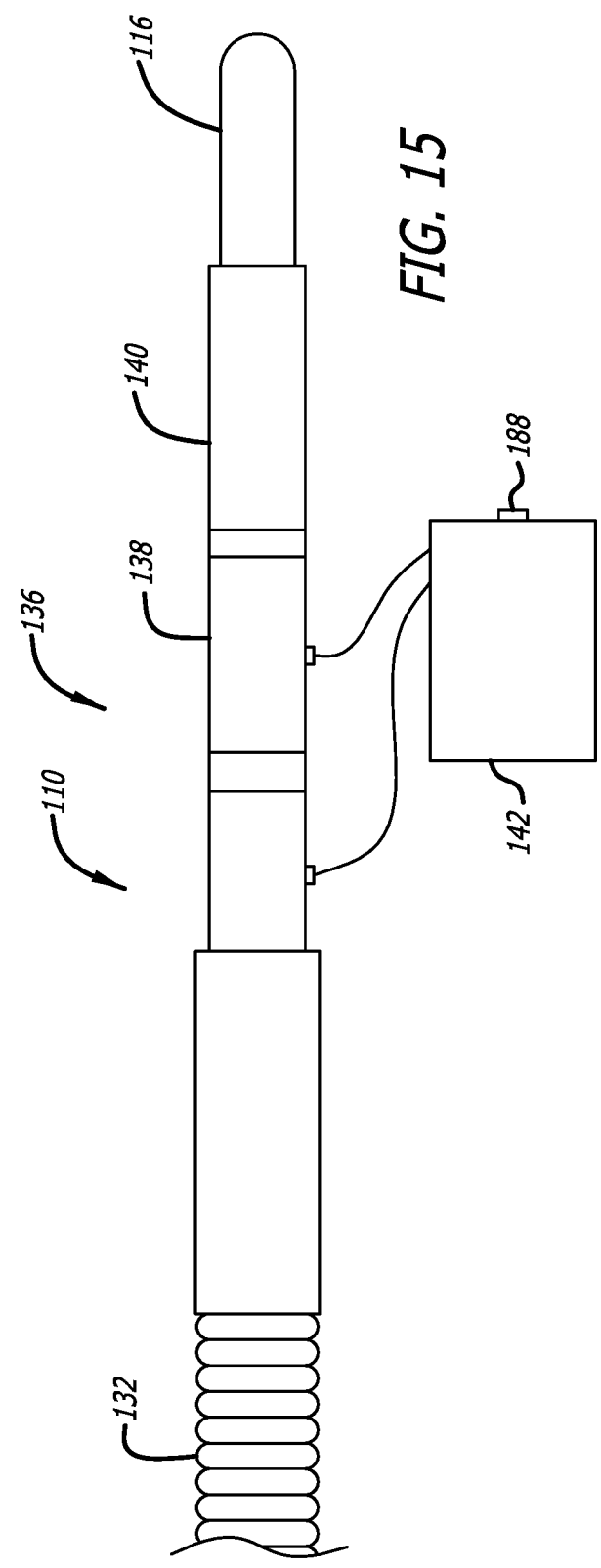

FIG. 46
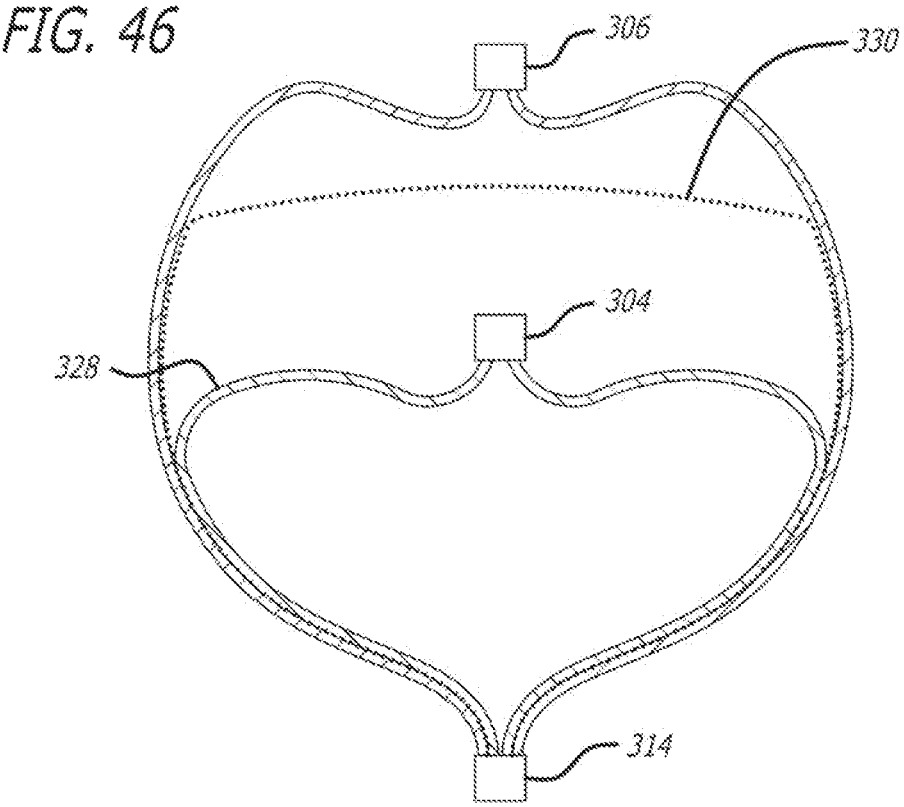
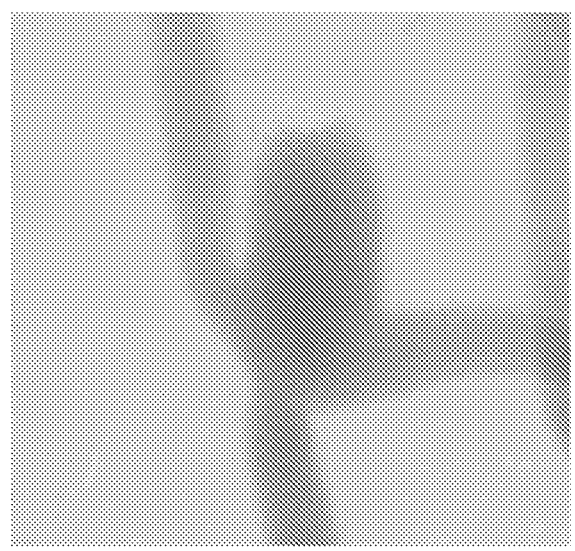
Pre-treatment Angiogram
FIG. 47
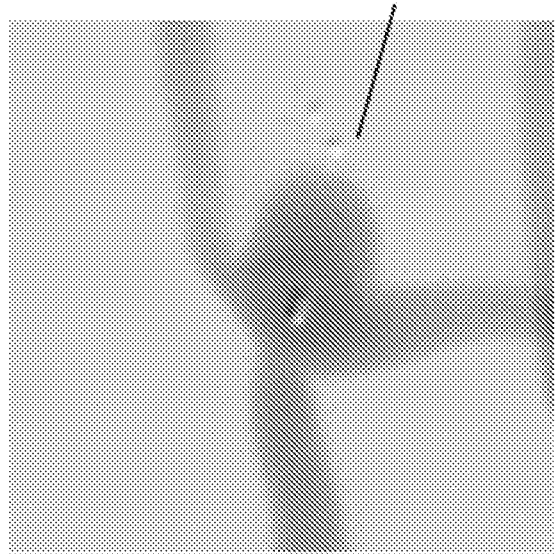
10 minutes Post treatment
FIG. 48

FILAMENTARY DEVICES FOR TREATMENT OF VASCULAR DEFECTS

RELATED PATENT APPLICATIONS

This is a continuation of U.S. application Ser. No. 17/028,037, filed Sep. 22, 2020, now U.S. Pat. No. 11,723,667, which is a continuation of U.S. application Ser. No. 16/163,287, filed Oct. 17, 2018, now U.S. Pat. No. 10,813,645, which is a continuation of U.S. application Ser. No. 15/336,634, filed Oct. 27, 2016, now U.S. Pat. No. 10,136,896, which is a continuation of U.S. application Ser. No. 15/071,632, filed Mar. 16, 2016, now U.S. Pat. No. 9,492,174, which is a continuation of U.S. application Ser. No. 14/871,352, filed on Sep. 30, 2015, now U.S. Pat. No. 9,295,473, which is a continuation of U.S. application Ser. No. 14/743,627, filed on Jun. 18, 2015, now U.S. Pat. No. 9,198,670, which is a continuation of U.S. application Ser. No. 14/459,638, filed on Aug. 14, 2014, now U.S. Pat. No. 9,078,658, which claims priority under 35 U.S.C. section 119 (e) from U.S. Provisional Application No. 61/866,993, filed Aug. 16, 2013, naming Todd J. Hewitt, Brian E. Merritt and Tan Q. Dinh as inventors, entitled FILAMENTARY DEVICES FOR TREATMENT OF VASCULAR DEFECTS, all of which are hereby incorporated by reference in their entireties for all purposes.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels which transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures which often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. Some such procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms and complexity and difficulty in the deployment thereof as most aneurysm treatments with this approach require the deployment of multiple coils.

Another approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

A number of aneurysm neck bridging devices with defect spanning portions or regions have been attempted, however, none of these devices have had a significant measure of clinical success or usage. A major limitation in their adoption and clinical usefulness is the inability to position the defect spanning portion to assure coverage of the neck. Existing stent delivery systems that are neurovascular compatible (i.e., deliverable through a microcatheter and highly flexible) do not have the necessary rotational positioning capability. Another limitation of many aneurysm bridging devices described in the prior art is the poor flexibility. Cerebral blood vessels are tortuous and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm, with a decreased risk of inadvertent aneurysm rupture or blood vessel wall damage. In addition, what have been needed are devices that are easily visible with current imaging technology such as x-ray, fluoroscopy, magnetic resonance imaging and the like.

SUMMARY

One embodiment of a device for treatment of a patient's vasculature includes a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, which define a cavity of the permeable shell and which include at least about 40% composite filaments relative to a total number of filaments, the composite filaments including a high strength material and a highly radiopaque material.

One embodiment of a device for treatment of a patient's vasculature includes a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, the plurality of filaments having a total cross sectional area and further defining a cavity of the permeable shell and which include at least some composite filaments, the composite filaments including a high strength material and a highly radiopaque material, and wherein the total cross sectional area of the highly radiopaque material is between about 11% and about 30% of the total cross sectional area of the plurality of elongate filaments.

BRIEF DESCRIPTION OF THE DRAWINGS

FIG. 12 is an elevation view of a distal portion of a delivery device or actuator showing some internal structure of the device.

FIG. 13 is an elevation view of the delivery device of FIG. 12 with the addition of some tubular elements over the internal structures.

FIG. 14 is an elevation view of the distal portion of the delivery device of FIG. 13 with an outer coil and marker in place.

FIG. 15 is an elevation view of a proximal portion of the delivery device.

FIG. 46 is an elevation view in partial section of an embodiment of a device for treatment of a patient's vasculature.

FIG. 47 represents the image of an angiogram depicting an aneurysm prior to treatment.

FIG. 48 depicts the aneurysm of FIG. 47 ten (10) minutes post-treatment.

DETAILED DESCRIPTION

Figure 1:
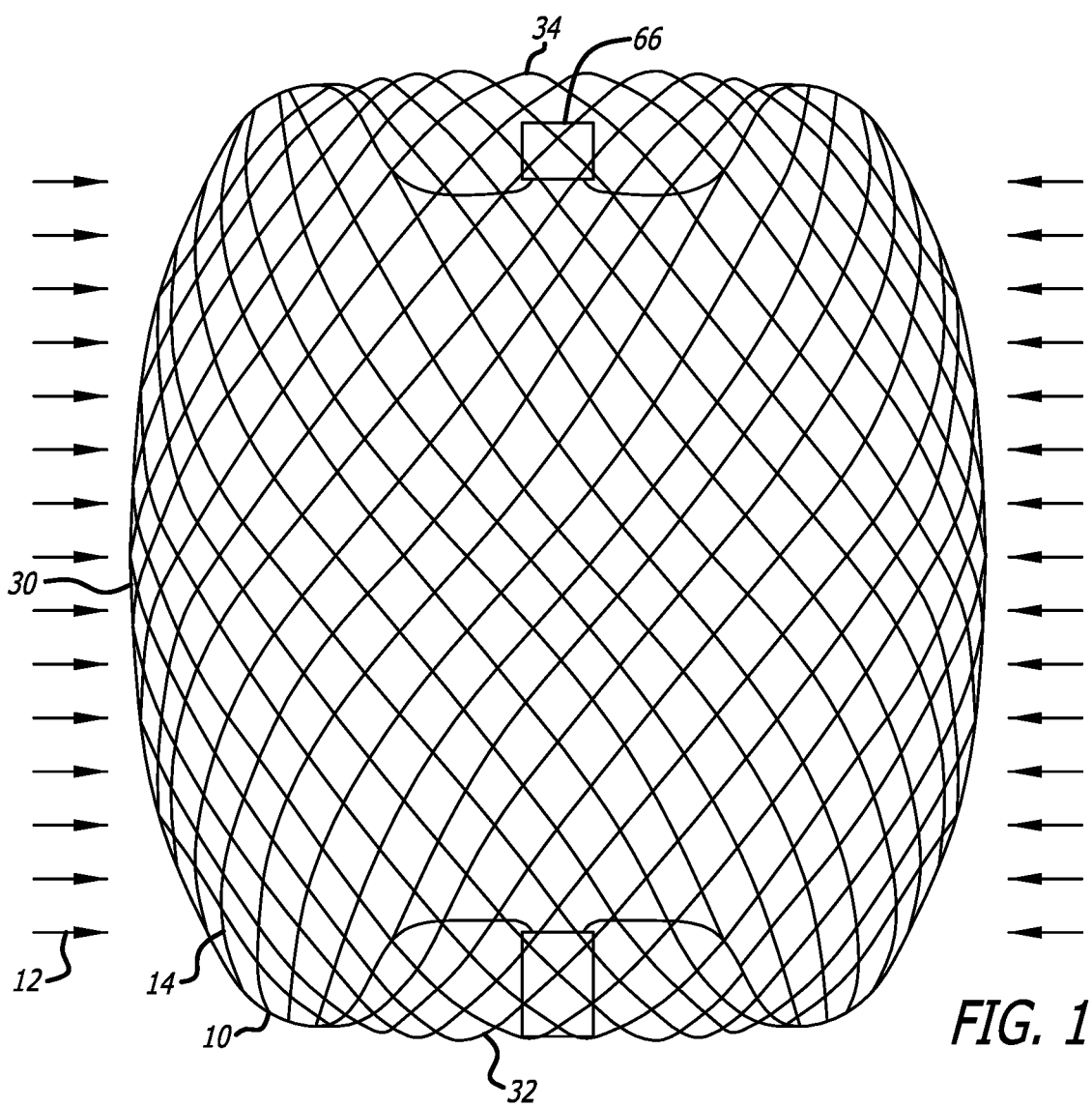
FIG. 1 is an elevation view of an embodiment of a device for treatment of a patient's vasculature and a plurality of arrows indicating inward radial force.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. It may also be desirable for some device embodiments to acutely occlude a vascular defect of a patient during the course of a procedure in order to provide more immediate feedback regarding success of the treatment to a treating physician.

It should be appreciated by those skilled in the art that unless otherwise stated, one or more of the features of the various embodiments may be used in other embodiments.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, a permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell may be configured to allow some initial perfusion of blood through the permeable shell. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane the dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

For some embodiments, three factors may be critical for a woven or braided wire occlusion device for treatment of a patient's vasculature that can achieve a desired clinical outcome in the endovascular treatment of cerebral aneurysms. We have found that for effective use in some applications, it may be desirable for the implant device to have sufficient radial stiffness for stability, limited pore size for near-complete acute (intra-procedural) occlusion and a collapsed profile which is small enough to allow insertion through an inner lumen of a microcatheter. A device with a radial stiffness below a certain threshold may be unstable and may be at higher risk of embolization in some cases. Larger pores between filament intersections in a braided or woven structure may not generate thrombus and occlude a vascular defect in an acute setting and thus may not give a treating physician or health professional such clinical feedback that the flow disruption will lead to a complete and lasting occlusion of the vascular defect being treated. Delivery of a device for treatment of a patient's vasculature through a standard microcatheter may be highly desirable to allow access through the tortuous cerebral vasculature in the manner that a treating physician is accustomed.

For some embodiments, it may be desirable to use filaments having two or more different diameters or transverse dimensions to form a permeable shell in order to produce a desired configuration as discussed in more detail below. The radial stiffness of a two-filament (two different diameters) woven device may be expressed as a function of the number of filaments and their diameters, as follows:

$$S_{radial} = (1.2 \times 10^6 \text{ lbf}/D^4)(N_l d_l^4 + N_s d_s^4)$$

where $S_{radial}$ is the radial stiffness in pounds force (lbf),
D is the Device diameter (transverse dimension),
$N_l$ is the number of large filaments,
$N_s$ is the number of small filaments,
$d_l$ is the diameter of the large filaments in inches, and
$d_s$ is the diameter of the small filaments in inches.

Using this expression, the radial stiffness, $S_{radial}$ may be between about 0.014 and 0.284 lbf force for some embodiments of particular clinical value.

The maximum pore size in a portion of a device that spans a neck or opening of a vascular defect desirable for some useful embodiments of a woven wire device for treatment of a patient's vasculature may be expressed as a function of the total number of all filaments, filament diameter and the device diameter. The difference between filament sizes where two or more filament diameters or transverse dimensions are used, may be ignored in some cases for devices where the filament size(s) are very small compared to the device dimensions. For a two-filament device, the smallest filament diameter may be used for the calculation. Thus, the maximum pore size for such embodiments may be expressed as follows:

$$p_{max} = (1.7/N_T)(\pi D - (N_T d_w/2))$$

where $P_{max}$ is the average pore size,
D is the Device diameter (transverse dimension),
$N_T$ is the total number of all filaments, and
$d_w$ is the diameter of the filaments (smallest) in inches.

Using this expression, the maximum pore size, Pmax, of a portion of a device that spans an opening of a vascular defect or neck, or any other suitable portion of a device, may be less than about 0.016 inches or about 400 microns for some embodiments. In some embodiments the maximum pore size for a defect spanning portion or any other suitable portion of a device may be less than about 0.012 inches or about 300 microns.

The collapsed profile of a two-filament (profile having two different filament diameters) woven filament device may be expressed as the function:

$$P_c = 1.48((N_l d_l^2 + N_s d_s^2))^{1/2}$$

where $P_c$ is the collapsed profile of the device,
$N_l$ is the number of large filaments,
$N_s$ is the number of small filaments,
$d_l$ is the diameter of the large filaments in inches, and
$d_s$ is the diameter of the small filaments in inches.

Using this expression, the collapsed profile Pc may be less than about 1.0 mm for some embodiments of particular clinical value.

In some embodiments of particular clinical value, the device may be constructed so as to have all three factors (Sradial, Pmax and Pc) above within the ranges discussed above; Sradial between about 0.014 lbf and 0.284 lbf, Pmax less than about 300 microns and Pc less than about 1.0 mm, simultaneously. In some such embodiments, the device may be made to include about 70 filaments to about 300 filaments. In some cases, the filaments may have an outer transverse dimension or diameter of about 0.0004 inches to about 0.002 inches.

As has been discussed, some embodiments of devices for treatment of a patient's vasculature call for sizing the device which approximates (or with some over-sizing) the vascular site dimensions to fill the vascular site. One might assume that scaling of a device to larger dimensions and using larger filaments would suffice for such larger embodiments of a device. However, for the treatment of brain aneurysms, the diameter or profile of the radially collapsed device is limited by the catheter sizes that can be effectively navigated within the small, tortuous vessels of the brain. Further, as a device is made larger with a given or fixed number of resilient filaments having a given size or thickness, the pores or openings between junctions of the filaments are correspondingly larger. In addition, for a given filament size the flexural modulus or stiffness of the filaments and thus the structure decreases with increasing device dimension. Flexural modulus may be defined as the ratio of stress to strain. Thus, a device may be considered to have a high flexural modulus or be stiff if the strain (deflection) is low under a given force. A stiff device may also be said to have low compliance.

Figure 2:
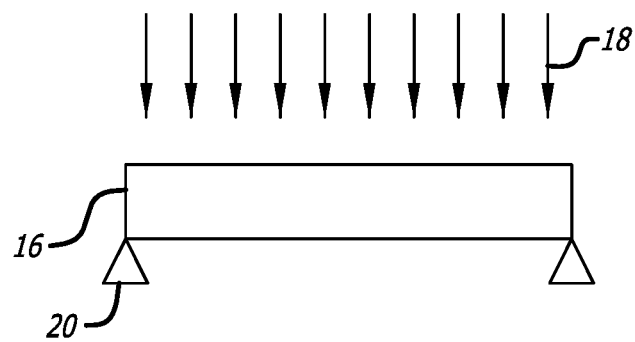
FIG. 2 is an elevation view of a beam supported by two simple supports and a plurality of arrows indicating force against the beam.
Figure 3:
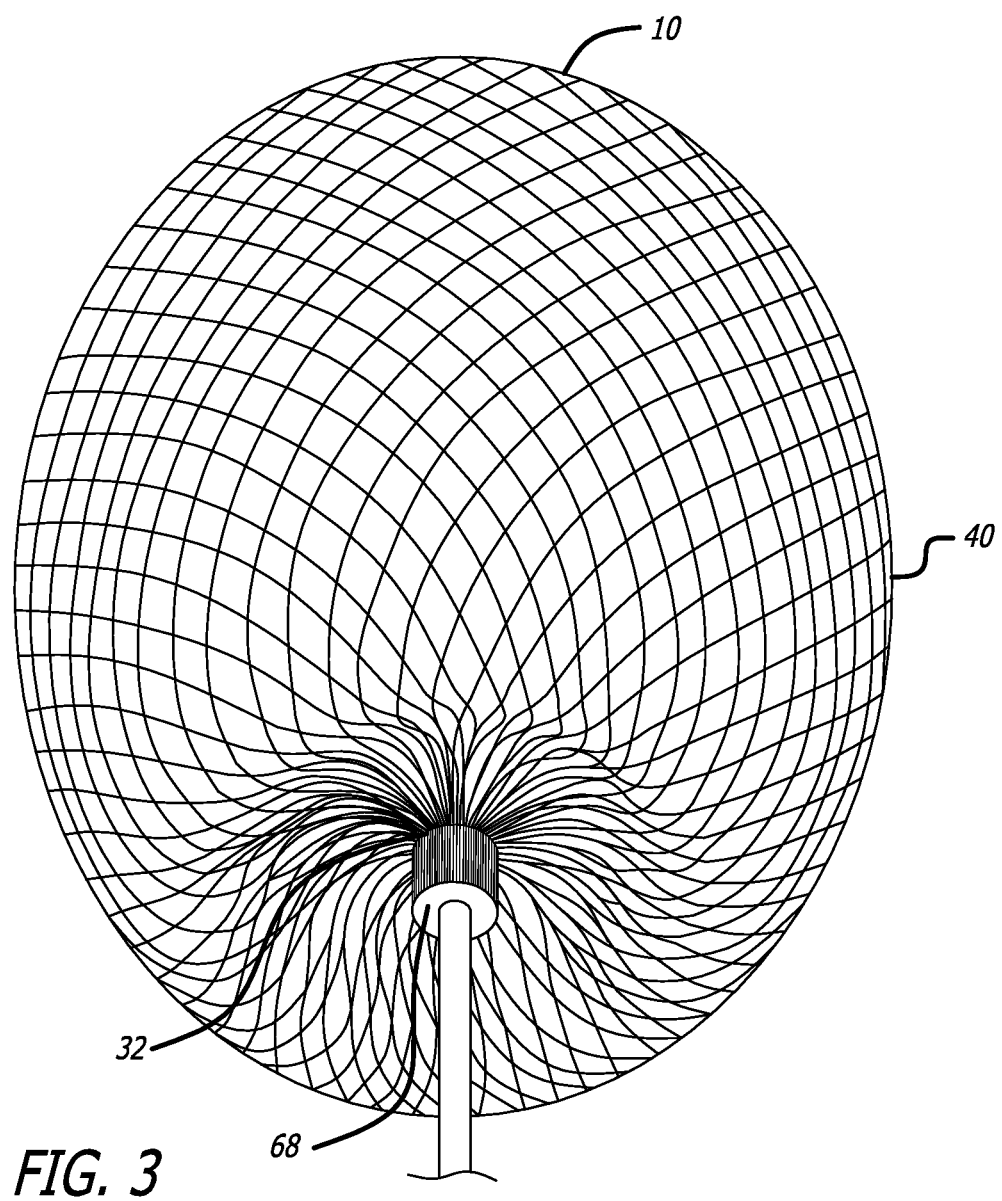
FIG. 3 is a bottom perspective view of an embodiment of a device for treatment of a patient's vasculature.

To properly configure larger size devices for treatment of a patient's vasculature, it may be useful to model the force on a device when the device is deployed into a vascular site or defect, such as a blood vessel or aneurysm, that has a diameter or transverse dimension that is smaller than a nominal diameter or transverse dimension of the device in a relaxed unconstrained state. As discussed, it may be advisable to "over-size" the device in some cases so that there is a residual force between an outside surface of the device and an inside surface of the vascular wall. The inward radial force on a device 10 that results from over-sizing is illustrated schematically in FIG. 1 with the arrows 12 in the figure representing the inward radial force. As shown in FIG. 2, these compressive forces on the filaments 14 of the device in FIG. 1 can be modeled as a simply supported beam 16 with a distributed load or force as shown by the arrows 18 in the figure. It can be seen from the equation below for the deflection of a beam with two simple supports 20 and a distributed load that the deflection is a function of the length, L to the 4th power:

Deflection of Beam=$5FL^4/384\ EI$ where F=force,
L=length of beam,
E=Young's Modulus, and
I=moment of inertia.

Thus, as the size of the device increases and L increases, the compliance increases substantially. Accordingly, an outward radial force exerted by an outside surface of the filaments 14 of the device 10 against a constraining force when inserted into a vascular site such as blood vessel or aneurysm is lower for a given amount of device compression or over-sizing. This force may be important in some applications to assure device stability and to reduce the risk of migration of the device and potential distal embolization.

In some embodiments, a combination of small and large filament sizes may be utilized to make a device with a desired radial compliance and yet have a collapsed profile which is configured to fit through an inner lumen of commonly used microcatheters. A device fabricated with even a small number of relatively large filaments 14 can provide reduced radial compliance (or increased stiffness) compared to a device made with all small filaments. Even a relatively small number of larger filaments may provide a substantial increase in bending stiffness due to change in the moment of Inertia that results from an increase in diameter without increasing the total cross sectional area of the filaments. The moment of inertia (I) of a round wire or filament may be defined by the equation:

$$I=\pi d^4/64$$

where d is the diameter of the wire or filament.

Since the moment of inertia is a function of filament diameter to the fourth power, a small change in the diameter greatly increases the moment of inertia. Thus, a small change in filament size can have substantial impact on the deflection at a given load and thus the compliance of the device.

Thus, the stiffness can be increased by a significant amount without a large increase in the cross sectional area of a collapsed profile of the device 10. This may be particularly important as device embodiments are made larger to treat large aneurysms. While large cerebral aneurysms may be relatively rare, they present an important therapeutic challenge as some embolic devices currently available to physicians have relatively poor results compared to smaller aneurysms.

As such, some embodiments of devices for treatment of a patient's vasculature may be formed using a combination of filaments 14 with a number of different diameters such as 2, 3, 4, 5 or more different diameters or transverse dimensions. In device embodiments where filaments with two different diameters are used, some larger filament embodiments may have a transverse dimension of about 0.001 inches to about 0.004 inches and some small filament embodiments may have a transverse dimension or diameter of about 0.0004 inches and about 0.0015 inches, more specifically, about 0.0004 inches to about 0.001 inches. The ratio of the number of large filaments to the number of small filaments may be between about 2 and 12 and may also be between about 4 and 8. In some embodiments, the difference in diameter or transverse dimension between the larger and smaller filaments may be less than about 0.004 inches, more specifically, less than about 0.0035 inches, and even more specifically, less than about 0.002 inches.

As discussed above, device embodiments 10 for treatment of a patient's vasculature may include a plurality of wires, fibers, threads, tubes or other filamentary elements that form a structure that serves as a permeable shell. For some embodiments, a globular shape may be formed from such filaments by connecting or securing the ends of a tubular braided structure. For such embodiments, the density of a braided or woven structure may inherently increase at or near the ends where the wires or filaments 14 are brought together and decrease at or near a middle portion 30 disposed between a proximal end 32 and distal end 34 of the permeable shell 40. For some embodiments, an end or any other suitable portion of a permeable shell 40 may be positioned in an opening or neck of a vascular defect such as an aneurysm for treatment. As such, a braided or woven filamentary device with a permeable shell may not require the addition of a separate defect spanning structure having properties different from that of a nominal portion of the permeable shell to achieve hemostasis and occlusion of the vascular defect. Such a filamentary device may be fabricated by braiding, weaving or other suitable filament fabrication techniques. Such device embodiments may be shape set into a variety of three dimensional shapes such as discussed herein. For example, any suitable braiding mechanism embodiment or braiding method embodiment such as those discussed in commonly owned U.S. Patent Publication No. 2013/0092013, published Apr. 18, 2013, titled "Braiding Mechanism and Methods of Use," which is incorporated by reference herein in its entirety, may be used to construct device embodiments disclosed herein.

Referring to FIGS. 3-10, an embodiment of a device for treatment of a patient's vasculature 10 is shown. The device 10 includes a self-expanding resilient permeable shell 40 having a proximal end 32, a distal end 34, a longitudinal axis 46 and further comprising a plurality of elongate resilient filaments 14 including large filaments 48 and small filaments 50 of at least two different transverse dimensions as shown in more detail in FIGS. 5, 7 and 18. The filaments 14 have a woven structure and are secured relative to each other at proximal ends 60 and distal ends 62 thereof. The permeable shell 40 of the device has a radially constrained elongated state configured for delivery within a microcatheter 61, as shown in FIG. 11, with the thin woven filaments 14 extending longitudinally from the proximal end 42 to the distal end 44 radially adjacent each other along a length of the filaments.

As shown in FIGS. 3-6, the permeable shell 40 also has an expanded relaxed state with a globular and longitudinally shortened configuration relative to the radially constrained state. In the expanded state, the woven filaments 14 form the self-expanding resilient permeable shell 40 in a smooth path radially expanded from a longitudinal axis 46 of the device between the proximal end 32 and distal end 34. The woven structure of the filaments 14 includes a plurality of openings 64 in the permeable shell 40 formed between the woven filaments. For some embodiments, the largest of said openings 64 may be configured to allow blood flow through the openings only at a velocity below a thrombotic threshold velocity. Thrombotic threshold velocity has been defined, at least by some, as the time-average velocity at which more than 50% of a vascular graft surface is covered by thrombus when deployed within a patient's vasculature. In the context of aneurysm occlusion, a slightly different threshold may be appropriate. Accordingly, the thrombotic threshold velocity as used herein shall include the velocity at which clotting occurs within or on a device, such as device 10, deployed within a patient's vasculature such that blood flow into a vascular defect treated by the device is substantially blocked in less than about 1 hour or otherwise during the treatment procedure. The blockage of blood flow into the vascular defect may be indicated in some cases by minimal contrast agent entering the vascular defect after a sufficient amount of contrast agent has been injected into the patient's vasculature upstream of the implant site and visualized as it dissipates from that site. Such sustained blockage of flow within less than about 1 hour or during the duration of the implantation procedure may also be referred to as acute occlusion of the vascular defect.

As such, once the device 10 is deployed, any blood flowing through the permeable shell may be slowed to a velocity below the thrombotic threshold velocity and thrombus will begin to form on and around the openings in the permeable shell 40. Ultimately, this process may be configured to produce acute occlusion of the vascular defect within which the device 10 is deployed. For some embodiments, at least the distal end of the permeable shell 40 may have a reverse bend in an everted configuration such that the secured distal ends 62 of the filaments 14 are withdrawn axially within the nominal permeable shell structure or contour in the expanded state. For some embodiments, the proximal end of the permeable shell further includes a reverse bend in an everted configuration such that the secured proximal ends 60 of the filaments 14 are withdrawn axially within the nominal permeable shell structure 40 in the expanded state. As used herein, the term everted may include a structure that is everted, partially everted and/or recessed with a reverse bend as shown in the device embodiment of FIGS. 3-6. For such embodiments, the ends 60 and 62 of the filaments 14 of the permeable shell or hub structure disposed around the ends may be withdrawn within or below the globular shaped periphery of the permeable shell of the device.

The elongate resilient filaments 14 of the permeable shell 40 may be secured relative to each other at proximal ends 60 and distal ends 62 thereof by one or more methods including welding, soldering, adhesive bonding, epoxy bonding or the like. In addition to the ends of the filaments being secured together, a distal hub 66 may also be secured to the distal ends 62 of the thin filaments 14 of the permeable shell 40 and a proximal hub 68 secured to the proximal ends 60 of the thin filaments 14 of the permeable shell 40. The proximal hub 68 may include a cylindrical member that extends proximally beyond the proximal ends 60 of the thin filaments so as to form a cavity 70 within a proximal portion of the proximal hub 68. The proximal cavity 70 may be used for holding adhesives such as epoxy, solder or any other suitable bonding agent for securing an elongate detachment tether 72 that may in turn be detachably secured to a delivery apparatus such as is shown in FIGS. 11-15.

For some embodiments, the elongate resilient filaments 14 of the permeable shell 40 may have a transverse cross section that is substantially round in shape and be made from a superelastic material that may also be a shape memory metal. The shape memory metal of the filaments of the permeable shell 40 may be heat set in the globular configuration of the relaxed expanded state as shown in FIGS. 3-6. Suitable superelastic shape memory metals may include alloys such as NiTi alloy and the like. The superelastic properties of such alloys may be useful in providing the resilient properties to the elongate filaments 14 so that they can be heat set in the globular form shown, fully constrained for delivery within an inner lumen of a microcatheter and then released to self expand back to substantially the original heat set shape of the globular configuration upon deployment within a patient's body.

The device 10 may have an everted filamentary structure with a permeable shell 40 having a proximal end 32 and a distal end 34 in an expanded relaxed state. The permeable shell 40 has a substantially enclosed configuration for the embodiments shown. Some or all of the permeable shell 40 of the device 10 may be configured to substantially block or impede fluid flow or pressure into a vascular defect or otherwise isolate the vascular defect over some period of time after the device is deployed in an expanded state. The permeable shell 40 and device 10 generally also has a low profile, radially constrained state, as shown in FIG. 11, with an elongated tubular or cylindrical configuration that includes the proximal end 32, the distal end 34 and a longitudinal axis 46. While in the radially constrained state, the elongate flexible filaments 14 of the permeable shell 40 may be disposed substantially parallel and in close lateral proximity to each other between the proximal end and distal end forming a substantially tubular or compressed cylindrical configuration.

Figure 4:
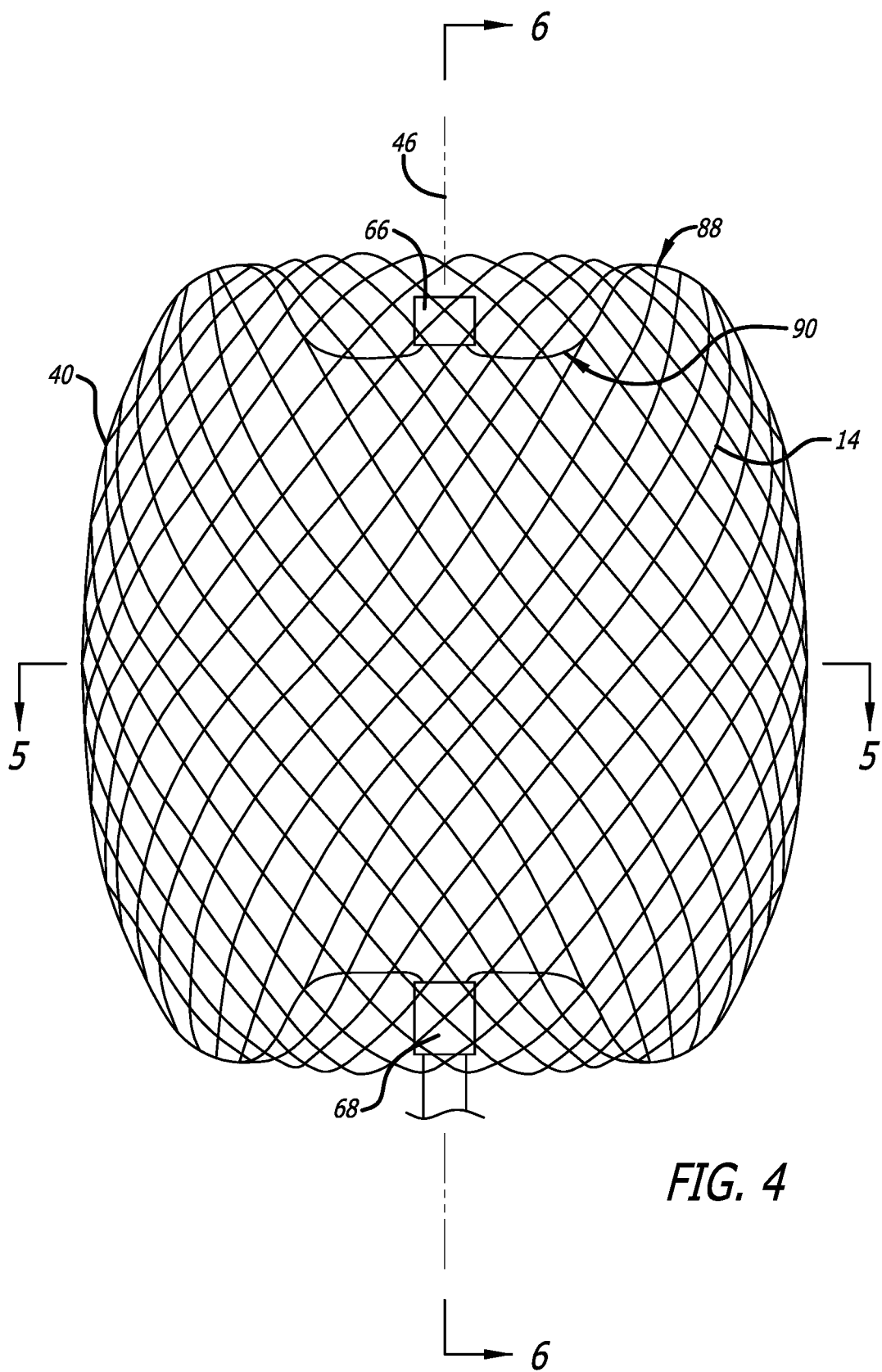
FIG. 4 is an elevation view of the device for treatment of a patient's vasculature of FIG. 3.
Figure 5:
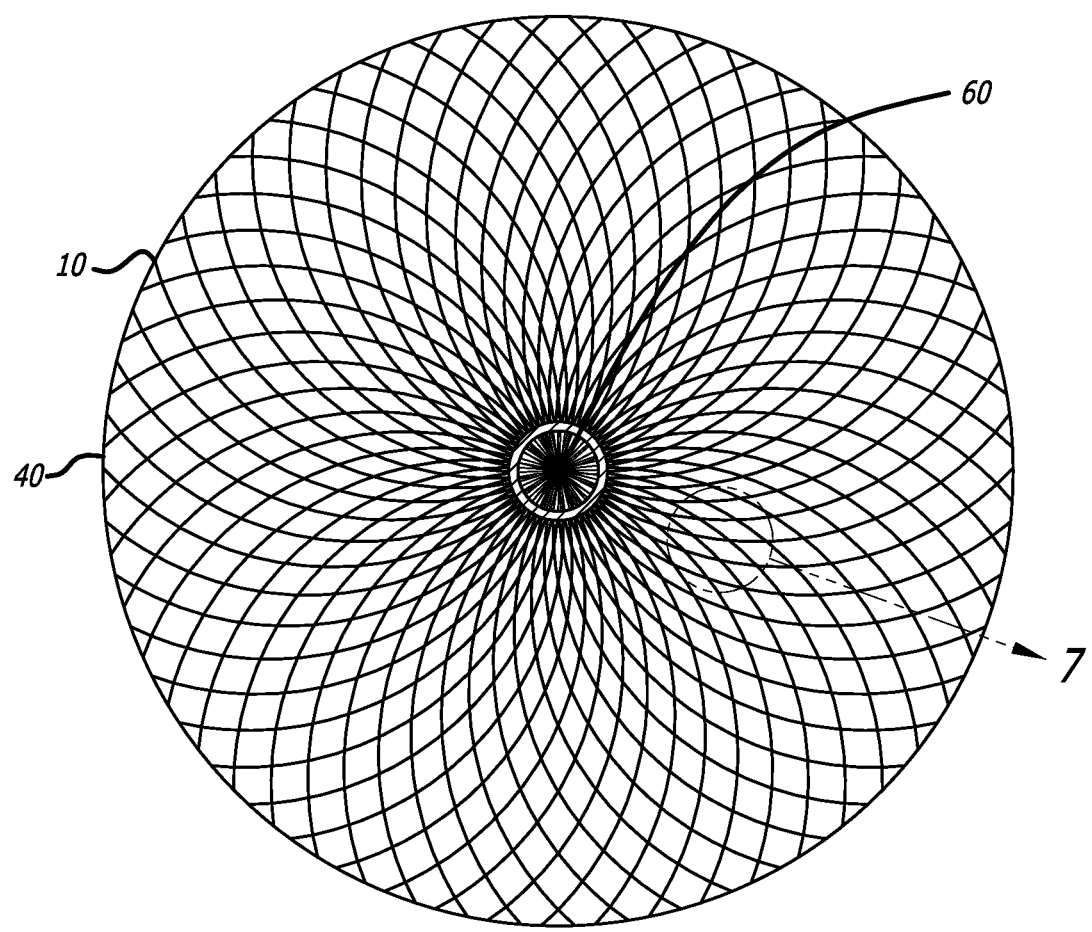
FIG. 5 is a transverse cross sectional view of the device of FIG. 4 taken along lines 5-5 in FIG. 4.

Proximal ends 60 of at least some of the filaments 14 of the permeable shell 40 may be secured to the proximal hub 68 and distal ends 62 of at least some of the filaments 14 of the permeable shell 40 are secured to the distal hub 66, with the proximal hub 68 and distal hub 66 being disposed substantially concentric to the longitudinal axis 46 as shown in FIG. 4. The ends of the filaments 14 may be secured to the respective hubs 66 and 68 by any of the methods discussed above with respect to securement of the filament ends to each other, including the use of adhesives, solder, welding and the like. In some cases, hubs may be made from a highly radiopaque material such as platinum, platinum alloy (e.g., 90% platinum/10% iridium), or gold. A middle portion 30 of the permeable shell 40 may have a first transverse dimension with a low profile suitable for delivery from a microcatheter as shown in FIG. 11. Radial constraint on the device 10 may be applied by an inside surface of the inner lumen of a microcatheter, such as the distal end portion of the microcatheter 61 shown, or it may be applied by any other suitable mechanism that may be released in a controllable manner upon ejection of the device 10 from the distal end of the catheter. In FIG. 11 a proximal end or hub 68 of the device 10 is secured to a distal end of an elongate delivery apparatus 110 of a delivery system 112 disposed at the proximal hub 68 of the device 10.

Some device embodiments 10 having a braided or woven filamentary structure may be formed using about 10 filaments to about 300 filaments 14, more specifically, about 10 filaments to about 100 filaments 14, and even more specifically, about 60 filaments to about 80 filaments 14. Some embodiments of a permeable shell 40 may include about 70 filaments to about 300 filaments extending from the proximal end 32 to the distal end 34, more specifically, about 100 filaments to about 200 filaments extending from the proximal end 32 to the distal end 34. For some embodiments, the filaments 14 may have a transverse dimension or diameter of about 0.0008 inches to about 0.004 inches. The elongate resilient filaments 14 in some cases may have an outer transverse dimension or diameter of about 0.0005 inch to about 0.005 inch, more specifically, about 0.001 inch to about 0.003 inch, and in some cases about 0.0004 inches to about 0.002 inches. For some device embodiments 10 that include filaments 14 of different sizes, the large filaments 48 of the permeable shell 40 may have a transverse dimension or diameter that is about 0.001 inches to about 0.004 inches and the small filaments 50 may have a transverse dimension or diameter of about 0.0004 inches to about 0.0015 inches, more specifically, about 0.0004 inches to about 0.001 inches. In addition, a difference in transverse dimension or diameter between the small filaments 50 and the large filaments 48 may be less than about 0.004 inches, more specifically, less than about 0.0035 inches, and even more specifically, less than about 0.002 inches. For embodiments of permeable shells 40 that include filaments 14 of different sizes, the number of small filaments 50 of the permeable shell 40 relative to the number of large filaments 48 of the permeable shell 40 may be about 2 to 1 to about 15 to 1, more specifically, about 2 to 1 to about 12 to 1, and even more specifically, about 4 to 1 to about 8 to 1.

The expanded relaxed state of the permeable shell 40, as shown in FIG. 4, has an axially shortened configuration relative to the constrained state such that the proximal hub 68 is disposed closer to the distal hub 66 than in the constrained state. Both hubs 66 and 68 are disposed substantially concentric to the longitudinal axis 46 of the device and each filamentary element 14 forms a smooth arc between the proximal and distal hubs 66 and 68 with a reverse bend at each end. A longitudinal spacing between the proximal and distal hubs 66 and 68 of the permeable shell 40 in a deployed relaxed state may be about 25 percent to about 75 percent of the longitudinal spacing between the proximal and distal hubs 66 and 68 in the constrained cylindrical state, for some embodiments. The arc of the filaments 14 between the proximal and distal ends 32 and 34 may be configured such that a middle portion of each filament 14 has a second transverse dimension substantially greater than the first transverse dimension.

For some embodiments, the permeable shell 40 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the permeable shell 40 in an expanded state may be about 2 times to about 150 times the first transverse dimension, more specifically, about 10 times to about 25 times the first or constrained transverse dimension. A longitudinal spacing between the proximal end 32 and distal end 34 of the permeable shell 40 in the relaxed expanded state may be about 25% percent to about 75% percent of the spacing between the proximal end 32 and distal end 34 in the constrained cylindrical state. For some embodiments, a major transverse dimension of the permeable shell 40 in a relaxed expanded state may be about 4 mm to about 30 mm, more specifically, about 9 mm to about 15 mm, and even more specifically, about 4 mm to about 8 mm.

Figure 6:
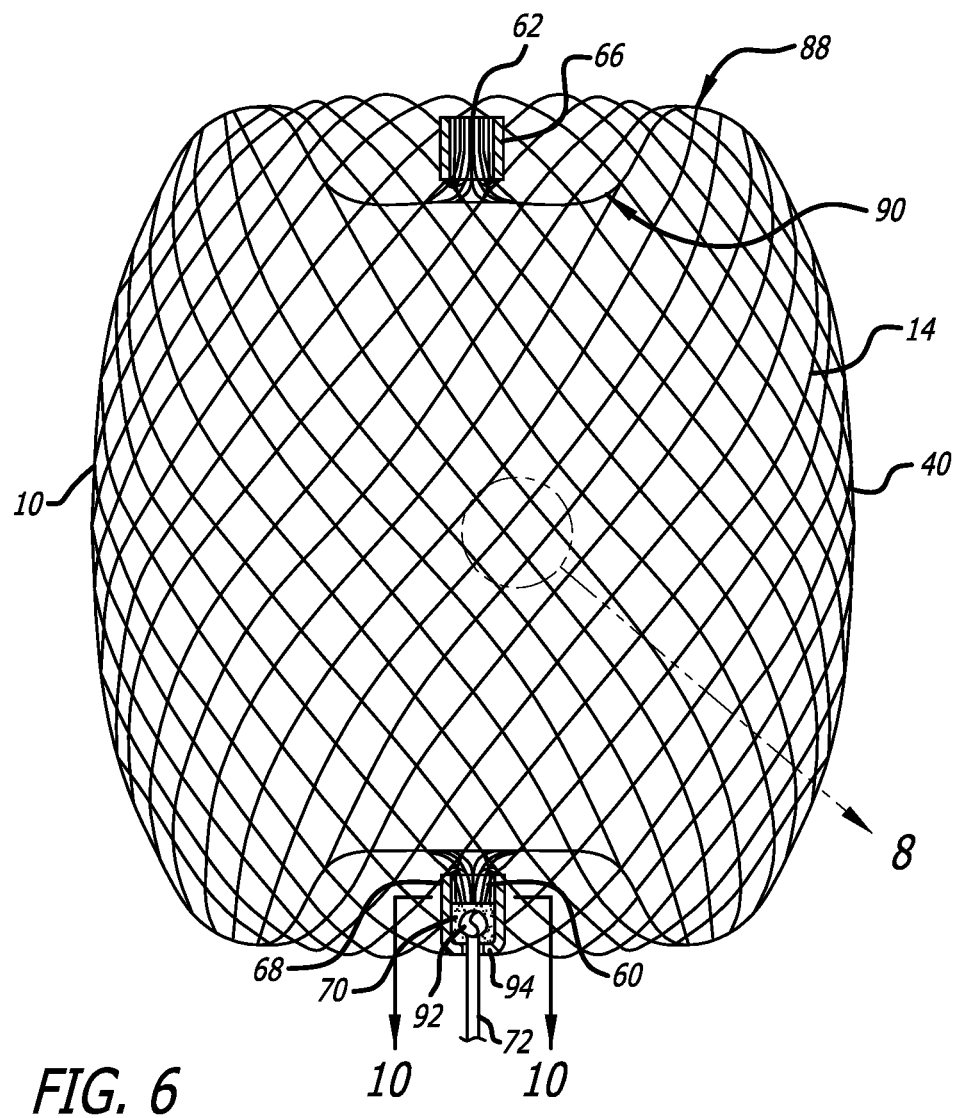
FIG. 6 shows the device of FIG. 4 in longitudinal section taken along lines 6-6 in FIG. 4.

An arced portion of the filaments 14 of the permeable shell 40 may have a sinusoidal-like shape with a first or outer radius 88 and a second or inner radius 90 near the ends of the permeable shell 40 as shown in FIG. 6. This sinusoid-like or multiple curve shape may provide a concavity in the proximal end 32 that may reduce an obstruction of flow in a parent vessel adjacent a vascular defect. For some embodiments, the first radius 88 and second radius 90 of the permeable shell 40 may be between about 0.12 mm to about 3 mm. For some embodiments, the distance between the proximal end 32 and distal end 34 may be less than about 60% of the overall length of the permeable shell 40 for some embodiments. Such a configuration may allow for the distal end 34 to flex downward toward the proximal end 32 when the device 10 meets resistance at the distal end 34 and thus may provide longitudinal conformance. The filaments 14 may be shaped in some embodiments such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. For some embodiments, one of the ends 32 or 34 may be retracted or everted to a greater extent than the other so as to be more longitudinally or axially conformal than the other end.

The first radius 88 and second radius 90 of the permeable shell 40 may be between about 0.12 mm to about 3 mm for some embodiments. For some embodiments, the distance between the proximal end 32 and distal end 34 may be more than about 60% of the overall length of the expanded permeable shell 40. Thus, the largest longitudinal distance between the inner surfaces may be about 60% to about 90% of the longitudinal length of the outer surfaces or the overall length of device 10. A gap between the hubs 66 and 68 at the proximal end 32 and distal end 34 may allow for the distal hub 66 to flex downward toward the proximal hub 68 when the device 10 meets resistance at the distal end and thus provides longitudinal conformance. The filaments 14 may be shaped such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. The distal end 34 may be retracted or everted to a greater extent than the proximal end 32 such that the distal end portion of the permeable shell 40 may be more radially conformal than the proximal end portion. Conformability of a distal end portion may provide better device conformance to irregular shaped aneurysms or other vascular defects. A convex surface of the device may flex inward forming a concave surface to conform to curvature of a vascular site.

Figure 10:
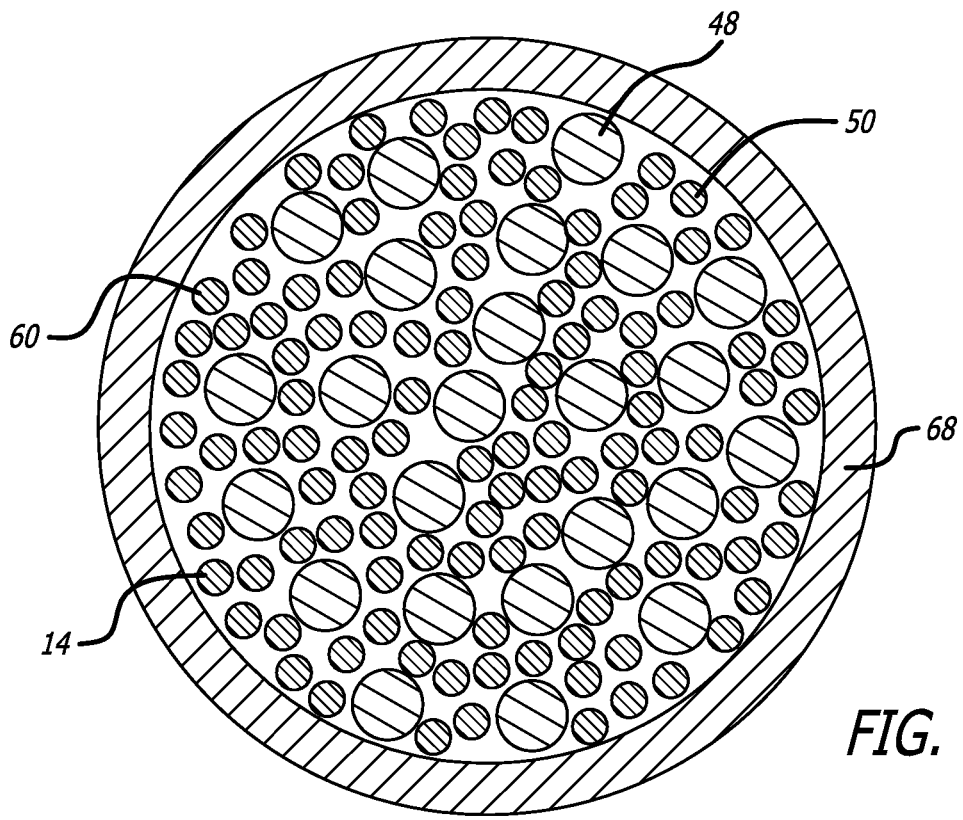
FIG. 10 is a transverse sectional view of a proximal hub portion of the device in FIG. 6 indicated by lines 10-10 in FIG. 6.
Figure 11:
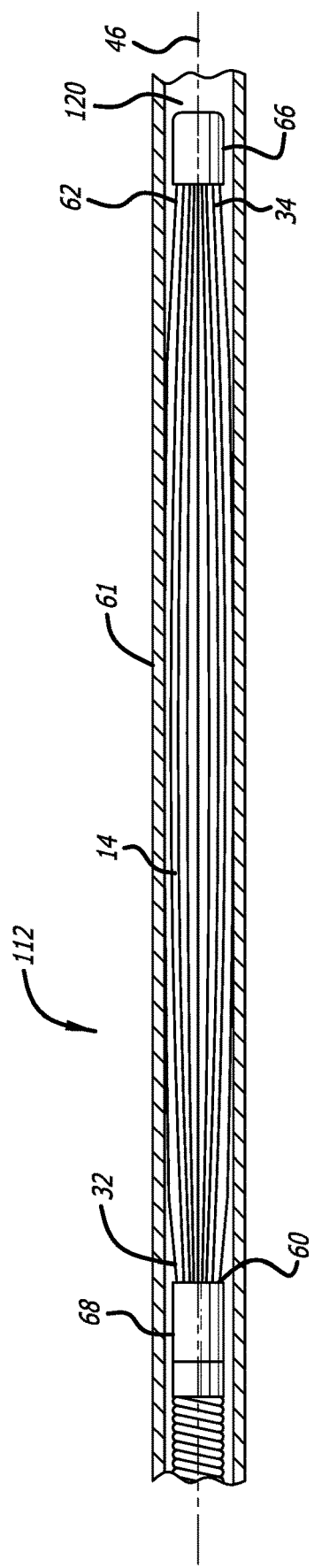
FIG. 11 is an elevation view in partial section of a distal end of a delivery catheter with the device for treatment of a patient's vasculature of FIG. 3 disposed therein in a collapsed constrained state.

FIG. 10 shows an enlarged view of the filaments 14 disposed within a proximal hub 68 of the device 10 with the filaments 14 of two different sizes constrained and tightly packed by an outer ring of the proximal hub 68. The tether member 72 may optionally be disposed within a middle portion of the filaments 14 or within the cavity 70 of the proximal hub 68 proximal of the proximal ends 60 of the filaments 14 as shown in FIG. 6. The distal end of the tether 72 may be secured with a knot 92 formed in the distal end thereof which is mechanically captured in the cavity 70 of the proximal hub 68 formed by a proximal shoulder portion 94 of the proximal hub 68. The knotted distal end 92 of the tether 72 may also be secured by bonding or potting of the distal end of the tether 72 within the cavity 70 and optionally amongst the proximal ends 60 of the filaments 14 with mechanical compression, adhesive bonding, welding, soldering, brazing or the like. The tether embodiment 72 shown in FIG. 6 has a knotted distal end 92 potted in the cavity of the proximal hub 68 with an adhesive. Such a tether 72 may be a dissolvable, severable or releasable tether that may be part of a delivery apparatus 110 used to deploy the device 10 as shown in FIG. 11 and FIGS. 23-26. FIG. 10 also shows the large filaments 48 and small filaments 50 disposed within and constrained by the proximal hub 68 which may be configured to secure the large and small filaments 48 and 50 in place relative to each other within the outer ring of the proximal hub 68.

Figure 7:
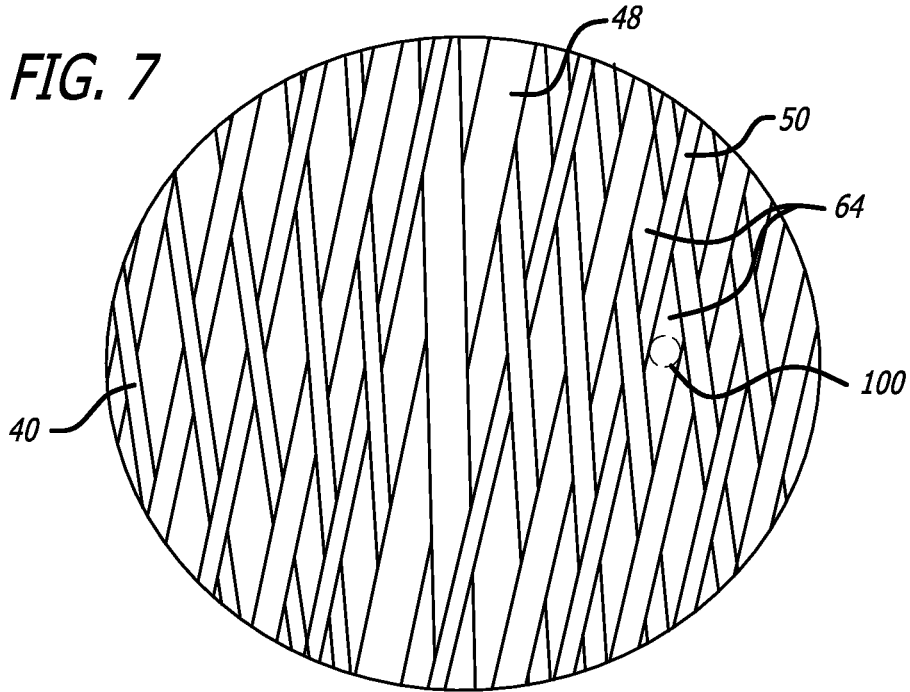
FIG. 7 is an enlarged view of the woven filament structure taken from the encircled portion 7 shown in FIG. 5.
Figure 8:
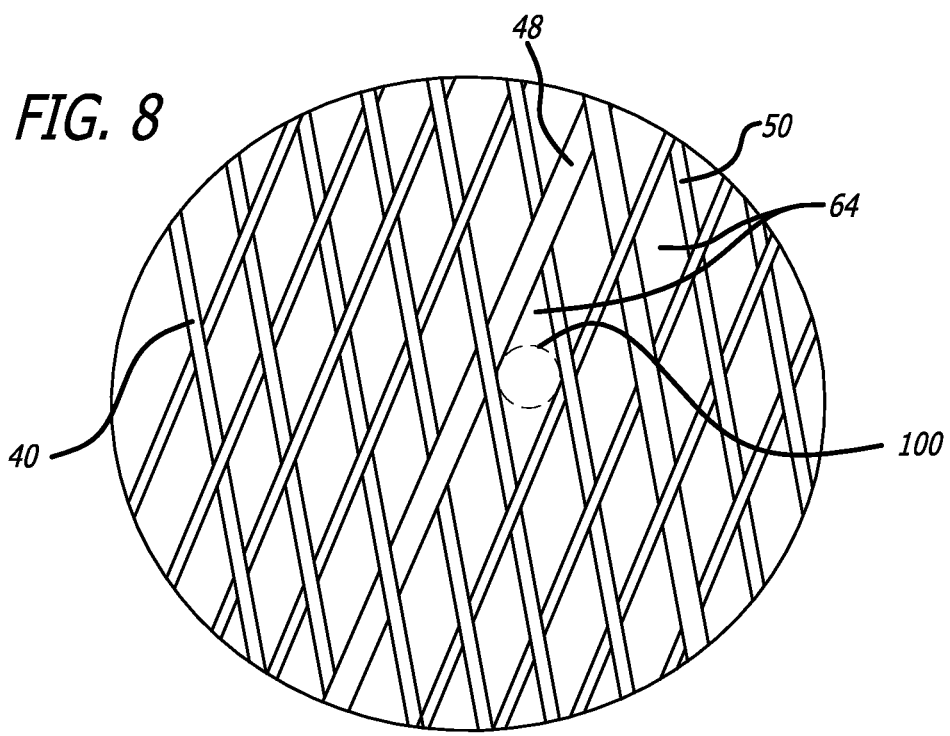
FIG. 8 is an enlarged view of the woven filament structure taken from the encircled portion 8 shown in FIG. 6.
Figure 9:
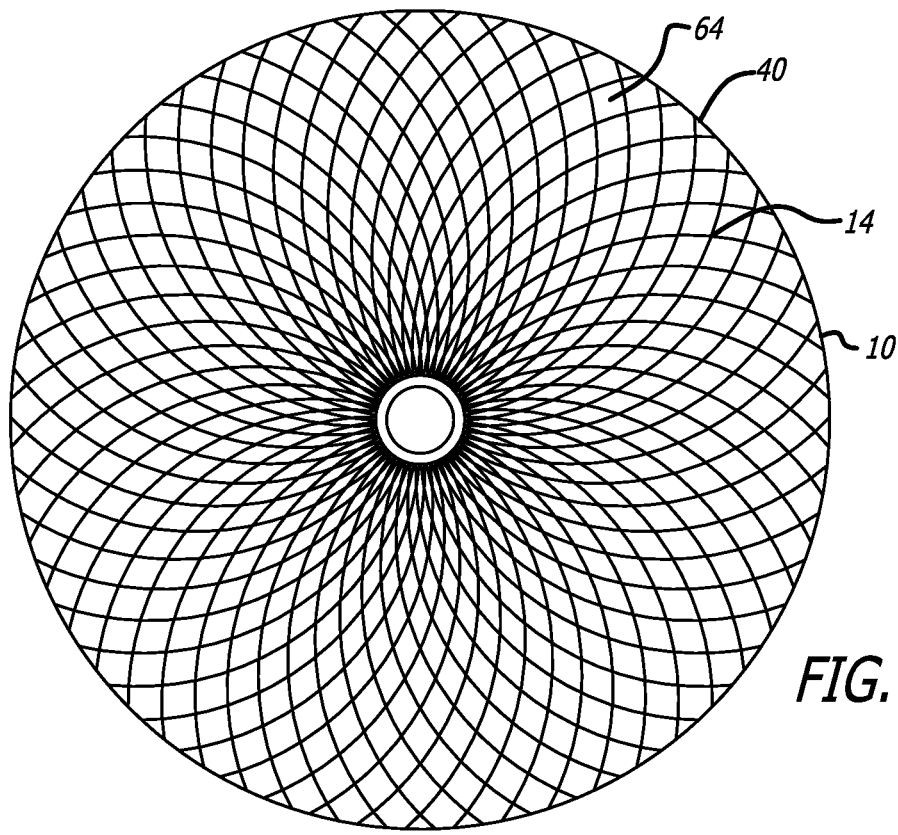
FIG. 9 is a proximal end view of the device of FIG. 3.

FIGS. 7 and 8 illustrate some configuration embodiments of braided filaments 14 of a permeable shell 40 of the device 10 for treatment of a patient's vasculature. The braid structure in each embodiment is shown with a circular shape 100 disposed within a pore 64 of a woven or braided structure with the circular shape 100 making contact with each adjacent filament segment. The pore opening size may be determined at least in part by the size of the filament elements 14 of the braid, the angle overlapping filaments make relative to each other and the picks per inch of the braid structure. For some embodiments, the cells or openings 64 may have an elongated substantially diamond shape as shown in FIG. 7, and the pores or openings 64 of the permeable shell 40 may have a substantially more square shape toward a middle portion 30 of the device 10, as shown in FIG. 8. The diamond shaped pores or openings 64 may have a length substantially greater than the width particularly near the hubs 66 and 68. In some embodiments, the ratio of diamond shaped pore or opening length to width may exceed a ratio of 3 to 1 for some cells. The diamond-shaped openings 64 may have lengths greater than the width thus having an aspect ratio, defined as Length/Width of greater than 1. The openings 64 near the hubs 66 and 68 may have substantially larger aspect ratios than those farther from the hubs as shown in FIG. 7. The aspect ratio of openings 64 adjacent the hubs may be greater than about 4 to 1. The aspect ratio of openings 64 near the largest diameter may be between about 0.75 to 1 and about 2 to 1 for some embodiments. For some embodiments, the aspect ratio of the openings 64 in the permeable shell 40 may be about 0.5 to 1 to about 2 to 1.

The pore size defined by the largest circular shapes 100 that may be disposed within openings 64 of the braided structure of the permeable shell 40 without displacing or distorting the filaments 14 surrounding the opening 64 may range in size from about 0.005 inches to about 0.01 inches, more specifically, about 0.006 inches to about 0.009 inches, even more specifically, about 0.007 inches to about 0.008 inches for some embodiments. In addition, at least some of the openings 64 formed between adjacent filaments 14 of the permeable shell 40 of the device 10 may be configured to allow blood flow through the openings 64 only at a velocity below a thrombotic threshold velocity. For some embodiments, the largest openings 64 in the permeable shell structure 40 may be configured to allow blood flow through the openings 64 only at a velocity below a thrombotic threshold velocity. As discussed above, the pore size may be less than about 0.016 inches, more specifically, less than about 0.012 inches for some embodiments. For some embodiments, the openings 64 formed between adjacent filaments 14 may be about 0.005 inches to about 0.04 inches.

Referring to FIGS. 12-15, a delivery apparatus embodiment 110 of the delivery system 112 of FIG. 11 is shown in more detail. The apparatus 110 includes an elongate core wire 114 that extends from a proximal end 116 of the apparatus 110 to a distal section 118 of the apparatus 110 as shown in FIG. 12. The core wire 114 is configured to provide sufficient column strength to push a constrained device 10 for treatment of a patient's vasculature through an inner lumen 120 of the microcatheter 61 of the delivery system 112 as shown in FIG. 11. The core wire 114 also has sufficient tensile strength to withdraw or proximally retract the device 10 from a position outside the microcatheter 61 and axially within the inner lumen 120 of the microcatheter 61. The tether 72 that extends proximally from the proximal hub 68 is secured to the distal end of the core wire 114 with a length of shrinkable tubing 122 that is disposed over a portion of the tether 72 and a distal section of the core wire 114 and shrunk over both as shown in FIG. 13, although any other suitable means of securement may be used.

A heater coil 124 electrically coupled to a first conductor 126 and a second conductor 128 is disposed over a distal most portion of the tether 72. The heater coil 124 may also be covered with a length of polymer tubing 130 disposed over the heater coil 124 distal of the heat shrink tubing 122 that serves to act as a heat shield and minimizes the leakage of heat from the heater coil 124 into the environment, such as the patient's blood stream, around the delivery apparatus 110. Once the heat shrink tubing 122 and insulating polymer tubing 130 have been secured to the distal section 118 of the apparatus 110, the proximal portion of the tether 72 disposed proximal of the heat shrink tubing 122 may be trimmed as shown in FIG. 13. An over coil 132 that extends from a distal end 134 of the delivery apparatus 110 to a proximal section 136 of the apparatus 110 may then be disposed over the heater coil 124, core wire 114, tether 72, first conductor 126 and second conductor 128 to hold these elements together, produce a low friction outer surface and maintain a desired flexibility of the delivery apparatus 110. The proximal section 136 of the apparatus 110 includes the proximal terminus of the over coil 132 which is disposed distal of a first contact 138 and second contact 140 which are circumferentially disposed about the proximal section 136 of the core wire 114, insulated therefrom, and electrically coupled to the first conductor 126 and second conductor 128, respectively as shown in FIG. 15.

The heater coil 124 may be configured to receive electric current supplied through the first conductor 126 and second conductor 128 from an electrical energy source 142 coupled to the first contact 138 and second contact 140 at the proximal section 136 of the apparatus 110. The electrical current passed through the heater coil 124 heats the heater coil to a temperature above the melting point of the tether material 72 so as to melt the tether 72 and sever it upon deployment of the device 10.

Embodiments of the delivery apparatus 110 may generally have a length greater than the overall length of a microcatheter 61 to be used for the delivery system 112. This relationship allows the delivery apparatus 110 to extend, along with the device 10 secured to the distal end thereof, from the distal port of the inner lumen 120 of the microcatheter 61 while having sufficient length extending from a proximal end 150 of the microcatheter 61, shown in FIG. 17 discussed below, to enable manipulation thereof by a physician. For some embodiments, the length of the delivery apparatus 110 may be about 170 cm to about 200 cm. The core wire 114 may be made from any suitable high strength material such as stainless steel, NiTi alloy, or the like. Embodiments of the core wire 114 may have an outer diameter or transverse dimension of about 0.010 inch to about 0.015 inch. The over coil 132 may have an outer diameter or transverse dimension of about 0.018 inch to about 0.03 inch. Although the apparatus embodiment 110 shown in FIGS. 12-15 is activated by electrical energy passed through a conductor pair, a similar configuration that utilizes light energy passed through a fiber optic or any other suitable arrangement could be used to remotely heat a distal heating member or element such as the heater coil 124 to sever the distal portion of the tether 72. In addition, other delivery apparatus embodiments are discussed and incorporated herein that may also be used for any of the device embodiments 10 for treatment of a patient's vasculature discussed herein.

Other delivery and positioning system embodiments may provide for the ability to rotate a device for treatment of a patient's vasculature in-vivo without translating torque along the entire length of the delivery apparatus. Some embodiments for delivery and positioning of devices 10 are described in co-owned International PCT Patent Application No. PCT/US2008/065694 which is incorporated by reference herein in its entirety. The delivery and positioning apparatus may include a distal rotating member that allows rotational positioning of the device. The delivery and positioning apparatus may include a distal rotating member which rotates an implant in-vivo without the transmission of torque along the entire length of the apparatus. Optionally, delivery system may also rotate the implant without the transmission of torque in the intermediate portion between the proximal end and the distal rotatable end. The delivery and positioning apparatus may be releasably secured to any suitable portion of the device for treatment of a patient's vasculature.

Device embodiments discussed herein may be releasable from any suitable flexible, elongate delivery apparatus or actuator such as a guidewire or guidewire-like structure. The release of device embodiments from such a delivery apparatus may be activated by a thermal mechanism, as discussed above, electrolytic mechanism, hydraulic mechanism, shape memory material mechanism, or any other mechanism known in the art of endovascular implant deployment.

Embodiments for deployment and release of therapeutic devices, such as deployment of embolic devices or stents within the vasculature of a patient, may include connecting such a device via a releasable connection to a distal portion of a pusher or other delivery apparatus member. The therapeutic device 10 may be detachably mounted to the distal portion of the apparatus by a filamentary tether 72, string, thread, wire, suture, fiber, or the like, which may be referred to above as the tether. The tether 72 may be in the form of a monofilament, rod, ribbon, hollow tube, or the like. Some embodiments of the tether may have a diameter or maximum thickness of between about 0.05 mm and 0.2 mm. The tether 72 may be configured to be able to withstand a maximum tensile load of between about 0.5 kg and 5 kg. For some embodiments, due to the mass of the device 10 being deployed which may be substantially greater than some embolic devices, some known detachment devices may lack sufficient tensile strength to be used for some embodiments discussed herein. As such, it may be desirable to use small very high strength fibers for some tether embodiments having a "load at break" greater than about 15 Newtons. For some embodiments, a tether made from a material known as Dyneema Purity available from Royal DSM, Heerlen, Netherlands may be used.

The tether 72 may be severed by the input of energy such as electric current to a heating element causing release of the therapeutic device. For some embodiments, the heating element may be a coil of wire with high electrical resistivity such as a platinum-tungsten alloy. The tether member may pass through or be positioned adjacent the heater element. The heater may be contained substantially within the distal portion of the delivery apparatus to provide thermal insulation to reduce the potential for thermal damage to the surrounding tissues during detachment. In another embodiment, current may pass through the tether which also acts as a heating element.

Many materials may be used to make tether embodiments 72 including polymers, metals and composites thereof. One class of materials that may be useful for tethers includes polymers such as polyolefin, polyolefin elastomer such as polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials that may be used for tether embodiment may include metals such as nickel titanium alloy (Nitinol), gold, platinum, tantalum and steel. Other materials that may be useful for tether construction includes wholly aromatic polyester polymers which are liquid crystal polymers (LCP) that may provide high performance properties and are highly inert. A commercially available LCP polymer is Vectran, which is produced by Kuraray Co. (Tokyo, Japan). The selection of the material may depend on the melting or softening temperature, the power used for detachment, and the body treatment site. The tether may be joined to the implant and/or the pusher by crimping, welding, knot tying, soldering, adhesive bonding, or other means known in the art.

Figure 16:
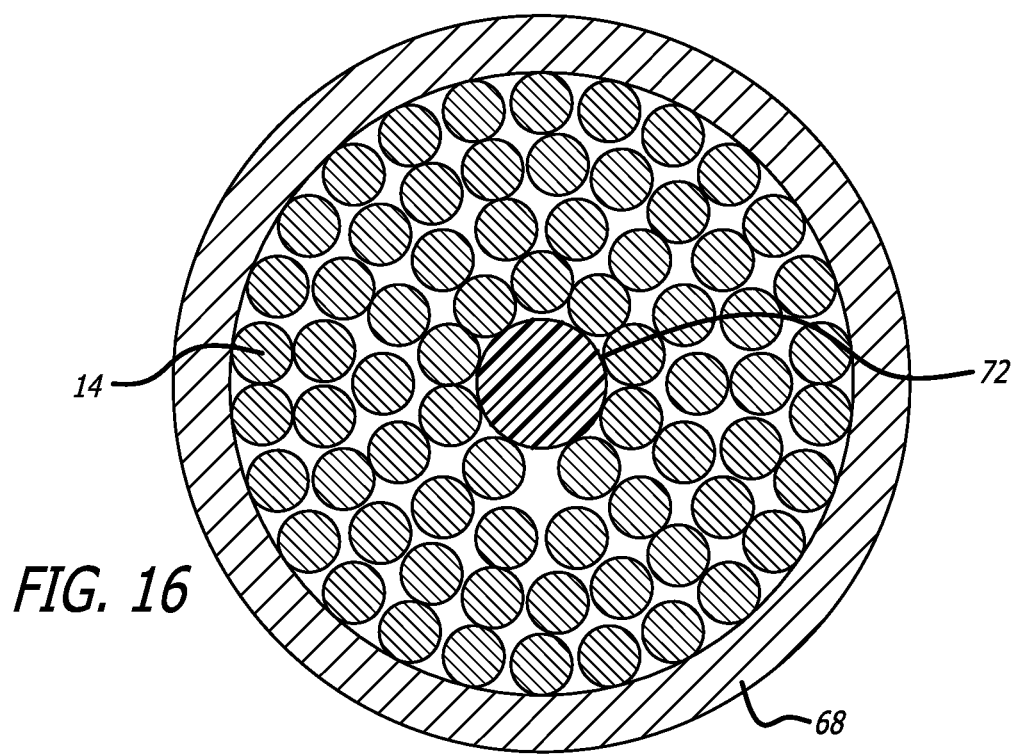
FIG. 16 illustrates an embodiment of a filament configuration for a device for treatment of a patient's vasculature.

It should be noted also that many variations of filament and proximal hub construction such as is detailed above with regard to FIG. 10 may be used for useful embodiments of a device for treatment of a patient's vasculature 10. FIG. 16 shows an enlarged view in transverse cross section of a proximal hub configuration. For the embodiment shown, the filaments 14 are disposed within a proximal hub 68 or end portion of the device 10 with the filaments 14 constrained and tightly packed by an outer ring of the proximal hub 68. A tether member 72 may be disposed within a middle portion of the filaments 14 or within a cavity of the proximal hub 68 proximal of the proximal ends 60 of the filaments 14. Such a tether 72 may be a dissolvable, severable or releasable tether that may be part of a release apparatus as discussed above used to deploy the device.

FIG. 16 illustrates in transverse cross section an embodiment of a proximal hub 68 showing the configuration of filaments which may be tightly packed and radially constrained by an inside surface of the proximal hub 68. In some embodiments, the braided or woven structure of the permeable shell 40 formed from such filaments 14 may be constructed using a large number of small filaments. The number of filaments 14 may be greater than 125 and may also be between about 80 filaments and about 180 filaments. As discussed above, the total number of filaments 14 for some embodiments may be about 70 filaments to about 300 filaments, more specifically, about 100 filaments to about 200 filaments. In some embodiments, the braided structure of the permeable shell 40 may be constructed with two or more sizes of filaments 14. For example, the structure may have several larger filaments that provide structural support and several smaller filaments that provide the desired pore size and density and thus flow resistance to achieve a thrombotic threshold velocity in some cases. For some embodiments, small filaments 50 of the permeable shell 40 may have a transverse dimension or diameter of about 0.0006 inches to about 0.002 inches for some embodiments and about 0.0004 inches to about 0.001 inches in other embodiments. The large filaments 48 may have a transverse dimension or diameter of about 0.0015 inches to about 0.004 inches in some embodiments and about 0.001 inches to about 0.004 inches in other embodiments. The filaments 14 may be braided in a plain weave that is one under, one over structure (shown in FIGS. 7 and 8) or a supplementary weave; more than one warp interlace with one or more than one weft. The pick count may be varied between about 25 and 200 picks per inch (PPI).

For some embodiments, the permeable shell 40 or portions thereof may be porous and may be highly permeable to liquids. In contrast to most vascular prosthesis fabrics or grafts which typically have a water permeability below 2,000 ml/min/cm2 when measured at a pressure of 120 mmHg, the permeable shell 40 of some embodiments discussed herein may have a water permeability greater than about 2,000 ml/min/cm2, in some cases greater than about 2,500 ml/min/cm2. For some embodiments, water permeability of the permeable shell 40 or portions thereof may be between about 2,000 and 10,000 ml/min/cm2, more specifically, about 2,000 ml/min/cm2 to about 15,000 ml/min/cm2, when measured at a pressure of 120 mmHg.

Device embodiments and components thereof may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g., polyethylene terephthalate or PET), PolyEtherEther Ketone (PEEK), polytetrafluoroethylene (PTFE), polycarbonate urethane (PCU) and polyurethane (PU). Device embodiments may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable (e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable. bioabsorbable polymer. Potentially suitable bioabsorbable materials include polylactic acid (PLA), poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials. An absorbable composite fiber may be made by combining a reinforcement fiber made from a copolymer of about 18% glycolic acid and about 82% lactic acid with a matrix material consisting of a blend of the above copolymer with about 20% polycaprolactone (PCL).

In any of the suitable device embodiments 10 discussed herein, the permeable shell structure 40 may include one or more fixation elements or surfaces to facilitate fixation of the device within a blood vessel or other vascular site. The fixation elements may comprise hooks, barbs, protrusions, pores, microfeatures, texturing, bioadhesives or combinations thereof. Embodiments of the support structure may be fabricated from a tube of metal where portions are removed. The removal of material may be done by laser, electrical discharge machining (EDM), photochemical etching and traditional machining techniques. In any of the described embodiments, the support structure may be constructed with a plurality of wires, cut or etched from a sheet of a material, cut or etched from a tube or a combination thereof as in the art of vascular stent fabrication.

Permeable shell embodiments 40 may be formed at least in part of wire, ribbon, or other filamentary elements 14. These filamentary elements 14 may have circular, elliptical, ovoid, square, rectangular, or triangular cross-sections. Permeable shell embodiments 40 may also be formed using conventional machining, laser cutting, electrical discharge machining (EDM) or photochemical machining (PCM). If made of a metal, it may be formed from either metallic tubes or sheet material.

Figure 17:
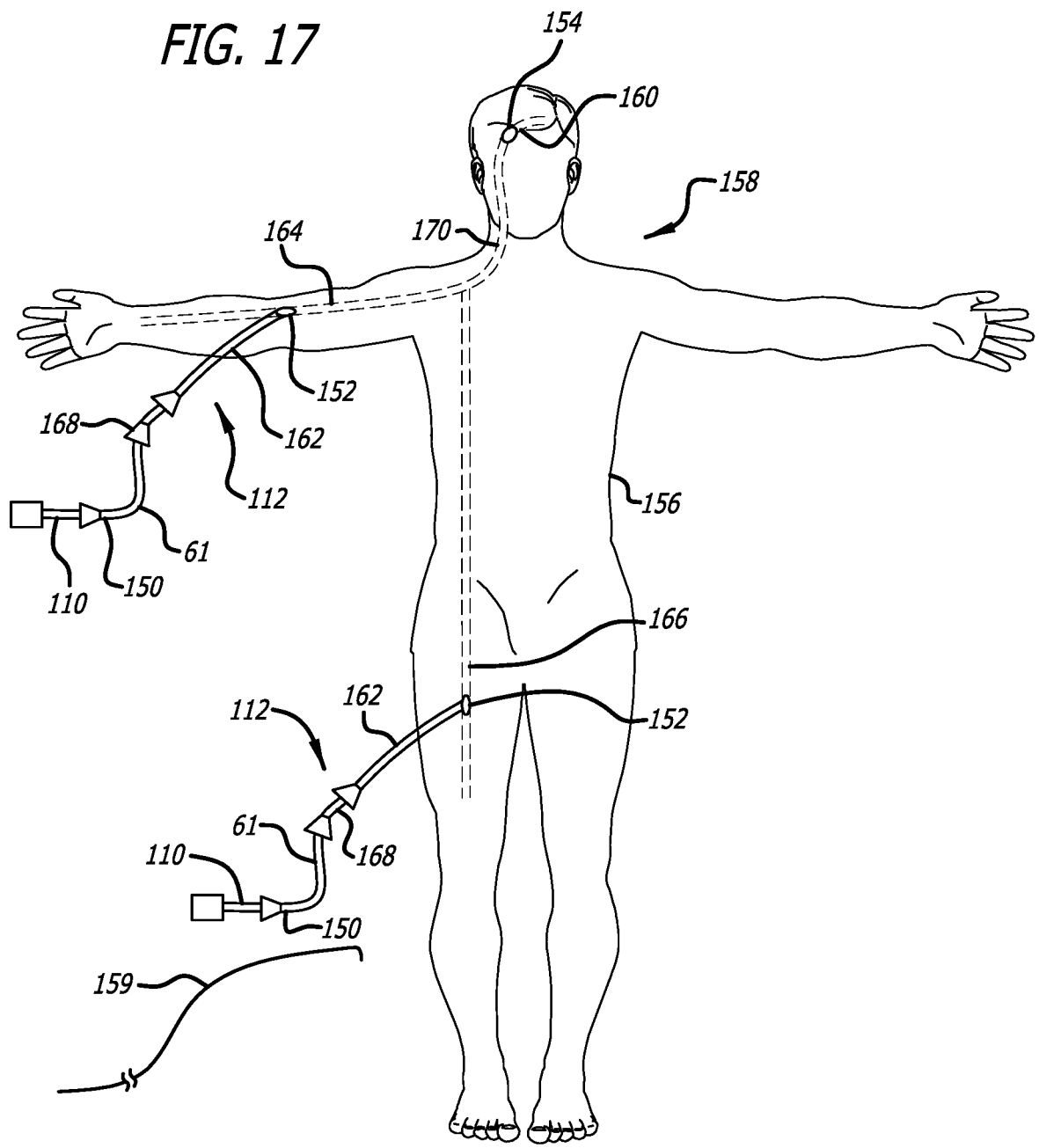
FIG. 17 is a schematic view of a patient being accessed by an introducer sheath, a microcatheter and a device for treatment of a patient's vasculature releasably secured to a distal end of a delivery device or actuator.
Figure 18:
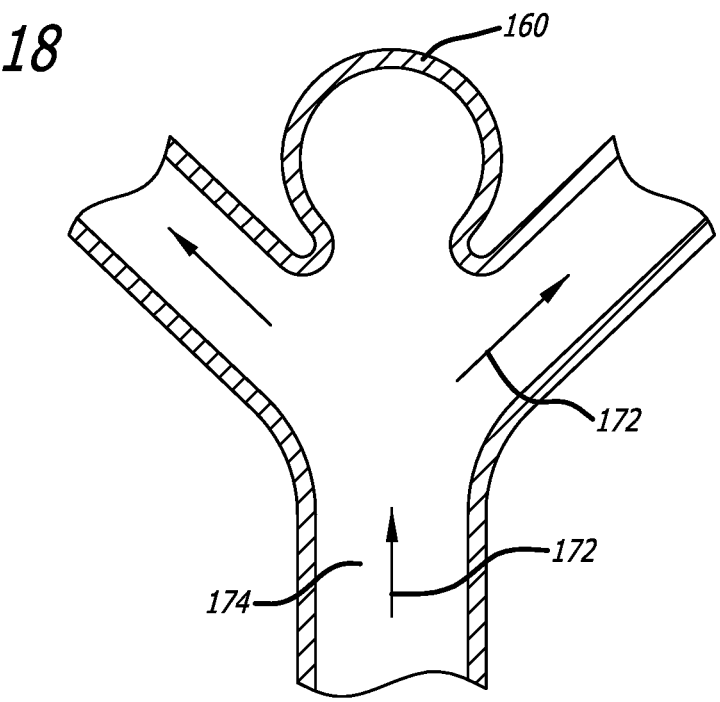
FIG. 18 is a sectional view of a terminal aneurysm.

Device embodiments 10 discussed herein may be delivered and deployed from a delivery and positioning system 112 that includes a microcatheter 61, such as the type of microcatheter 61 that is known in the art of neurovascular navigation and therapy. Device embodiments for treatment of a patient's vasculature 10 may be elastically collapsed and restrained by a tube or other radial restraint, such as an inner lumen 120 of a microcatheter 61, for delivery and deployment. The microcatheter 61 may generally be inserted through a small incision 152 accessing a peripheral blood vessel such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the device 10 secured to a delivery apparatus 110 of the delivery system 112 through the inner lumen 120 of a microcatheter 61 in some cases. FIG. 17 illustrates a schematic view of a patient 158 undergoing treatment of a vascular defect 160 as shown in FIG. 18. An access sheath 162 is shown disposed within either a radial artery 164 or femoral artery 166 of the patient 158 with a delivery system 112 that includes a microcatheter 61 and delivery apparatus 110 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, and the like in order to achieve percutaneous access to a vascular defect 160. In general, the patient 158 may be prepared for surgery and the access artery is exposed via a small surgical incision 152 and access to the lumen is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use include the Synchro2® made by Boston Scientific and the Glidewire Gold Neuro® made by MicroVention Terumo. Typical guidewire sizes may include 0.014 inches and 0.018 inches. Once the distal end 151 of the catheter 61 is positioned at the site, often by locating its distal end through the use of radiopaque marker material and fluoroscopy, the catheter is cleared. For example, if a guidewire 159 has been used to position the microcatheter 61, it is withdrawn from the catheter 61 and then the implant delivery apparatus 110 is advanced through the microcatheter 61.

Delivery and deployment of device embodiments 10 discussed herein may be carried out by first compressing the device 10 to a radially constrained and longitudinally flexible state as shown in FIG. 11. The device 10 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The device 10 secured to a suitable delivery apparatus 110 may then be radially constrained, inserted into a proximal portion of the inner lumen 120 of the microcatheter 61 and distally advanced to the vascular defect 160 through the inner lumen 120.

Once disposed within the vascular defect 160, the device 10 may then allowed to assume an expanded relaxed or partially relaxed state with the permeable shell 40 of the device spanning or partially spanning a portion of the vascular defect 160 or the entire vascular defect 160. The device 10 may also be activated by the application of an energy source to assume an expanded deployed configuration once ejected from the distal section of the microcatheter 61 for some embodiments. Once the device 10 is deployed at a desired treatment site 154, the microcatheter 61 may then be withdrawn.

Figure 19:
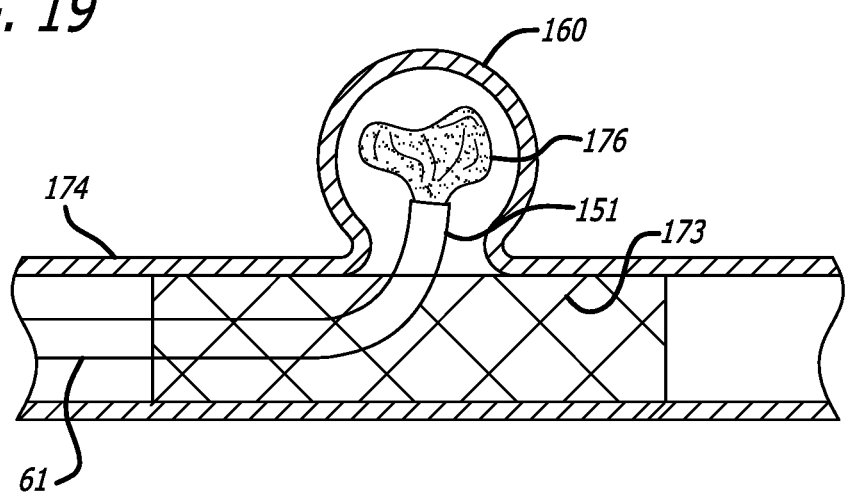
FIG. 19 is a sectional view of an aneurysm.

Some embodiments of devices for the treatment of a patient's vasculature 10 discussed herein may be directed to the treatment of specific types of defects of a patient's vasculature. For example, referring to FIG. 18, an aneurysm 160 commonly referred to as a terminal aneurysm is shown in section. Terminal aneurysms occur typically at bifurcations in a patient's vasculature where blood flow, indicated by the arrows 172, from a supply vessel splits into two or more branch vessels directed away from each other. The main flow of blood from the supply vessel 174, such as a basilar artery, sometimes impinges on the vessel where the vessel diverges and where the aneurysm sack forms. Terminal aneurysms may have a well defined neck structure where the profile of the aneurysm 160 narrows adjacent the nominal vessel profile, but other terminal aneurysm embodiments may have a less defined neck structure or no neck structure. FIG. 19 illustrates a typical berry type aneurysm 160 in section where a portion of a wall of a nominal vessel section weakens and expands into a sack like structure ballooning away from the nominal vessel surface and profile. Some berry type aneurysms may have a well defined neck structure as shown in FIG. 19, but others may have a less defined neck structure or none at all. FIG. 19 also shows some optional procedures wherein a stent 173 or other type of support has been deployed in the parent vessel 174 adjacent the aneurysm. Also, shown is embolic material 176 being deposited into the aneurysm 160 through a microcatheter 61. Either or both of the stent 173 and embolic material 176 may be so deployed either before or after the deployment of a device for treatment of a patient's vasculature 10.

Figure 28:
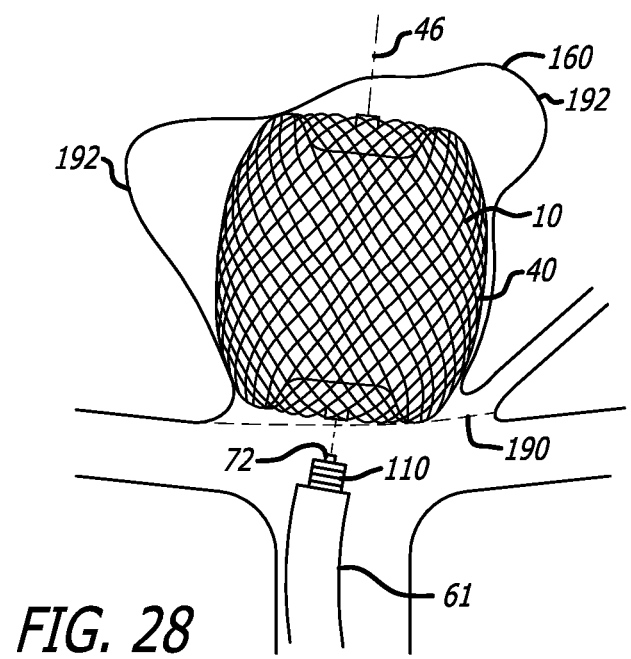
FIG. 28 is an elevation view in partial section of an embodiment of a device for treatment of a patient's vasculature deployed within an irregularly shaped aneurysm.

Prior to delivery and deployment of a device for treatment of a patient's vasculature 10, it may be desirable for the treating physician to choose an appropriately sized device 10 to optimize the treatment results. Some embodiments of treatment may include estimating a volume of a vascular site or defect 160 to be treated and selecting a device 10 with a volume that is substantially the same volume or slightly over-sized relative to the volume of the vascular site or defect 160. The volume of the vascular defect 160 to be occluded may be determined using three-dimensional angiography or other similar imaging techniques along with software which calculates the volume of a selected region. The amount of over-sizing may be between about 2% and 15% of the measured volume. In some embodiments, such as a very irregular shaped aneurysm, it may be desirable to under-size the volume of the device 10. Small lobes or "daughter aneurysms" may be excluded from the volume, defining a truncated volume which may be only partially filled by the device without affecting the outcome. A device 10 deployed within such an irregularly shaped aneurysm 160 is shown in FIG. 28 discussed below. Such a method embodiment may also include implanting or deploying the device 10 so that the vascular defect 160 is substantially filled volumetrically by a combination of device and blood contained therein. The device 10 may be configured to be sufficiently conformal to adapt to irregular shaped vascular defects 160 so that at least about 75%, in some cases about 80%, of the vascular defect volume is occluded by a combination of device 10 and blood contained therein.

Figure 20:
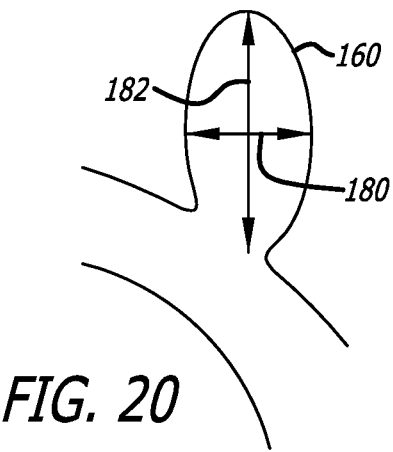
FIG. 20 is a schematic view in section of an aneurysm showing perpendicular arrows that indicate interior nominal longitudinal and transverse dimensions of the aneurysm.
Figure 21:
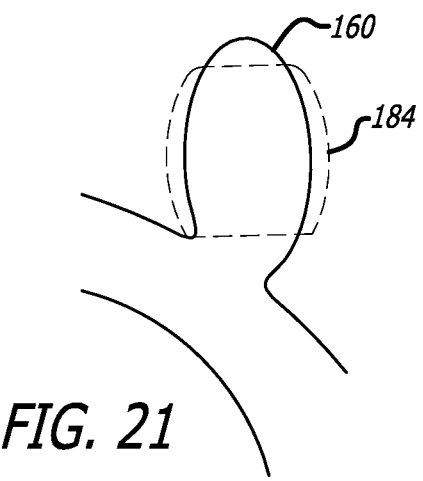
FIG. 21 is a schematic view in section of the aneurysm of FIG. 20 with a dashed outline of a device for treatment of a patient's vasculature in a relaxed unconstrained state that extends transversely outside of the walls of the aneurysm.
Figure 22:
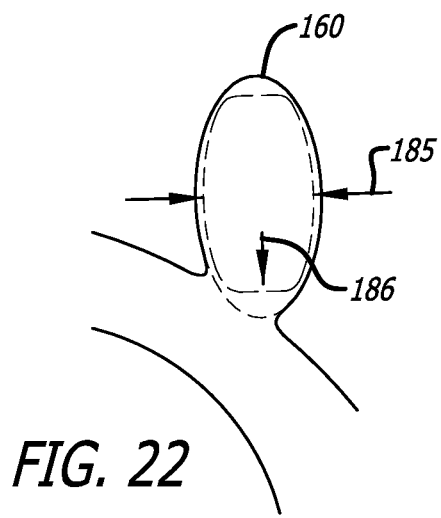
FIG. 22 is a schematic view in section of an outline of a device represented by the dashed line in FIG. 21 in a deployed and partially constrained state within the aneurysm.

In particular, for some treatment embodiments, it may be desirable to choose a device 10 that is properly oversized in a transverse dimension so as to achieve a desired conformance, radial force and fit after deployment of the device 10. FIGS. 20-22 illustrate a schematic representation of how a device 10 may be chosen for a proper fit after deployment that is initially oversized in a transverse dimension by at least about 10% of the largest transverse dimension of the vascular defect 160 and sometimes up to about 100% of the largest transverse dimension. For some embodiments, the device 10 may be oversized a small amount (e.g., less than about 1.5 mm) in relation to measured dimensions for the width, height or neck diameter of the vascular defect 160.

In FIG. 20, a vascular defect 160 in the form of a cerebral aneurysm is shown with horizontal arrows 180 and vertical arrows 182 indicating the approximate largest interior dimensions of the defect 160. Arrow 180 extending horizontally indicates the largest transverse dimension of the defect 160. In FIG. 21, a dashed outline 184 of a device for treatment of the vascular defect 10 is shown superimposed over the vascular defect 160 of FIG. 20 illustrating how a device 10 that has been chosen to be approximately 20% oversized in a transverse dimension would look in its unconstrained, relaxed state. FIG. 22 illustrates how the device 10 which is indicated by the dashed line 184 of FIG. 21 might conform to the interior surface of the vascular defect 160 after deployment whereby the nominal transverse dimension of the device 10 in a relaxed unconstrained state has now been slightly constrained by the inward radial force 185 exerted by the vascular defect 160 on the device 10. In response, as the filaments 14 of the device 10 and thus the permeable shell 40 made therefrom have a constant length, the device 10 has assumed a slightly elongated shape in the axial or longitudinal axis of the device 10 so as to elongate and better fill the interior volume of the defect 160 as indicated by the downward arrow 186 in FIG. 22.

Figure 23:
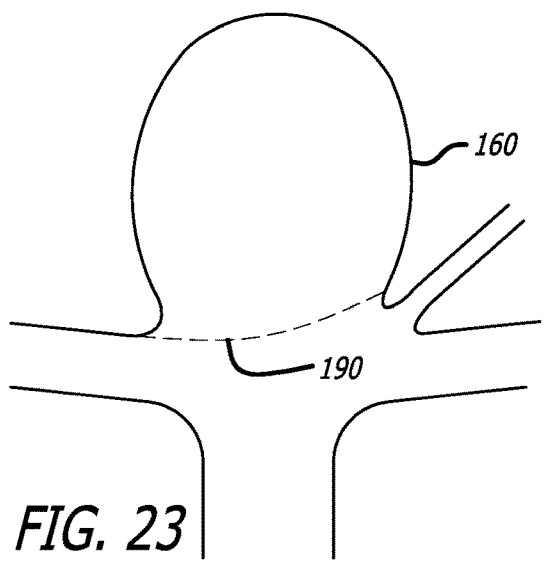
FIGS. 23-26 show a deployment sequence of a device for treatment of a patient's vasculature.
Figure 24:
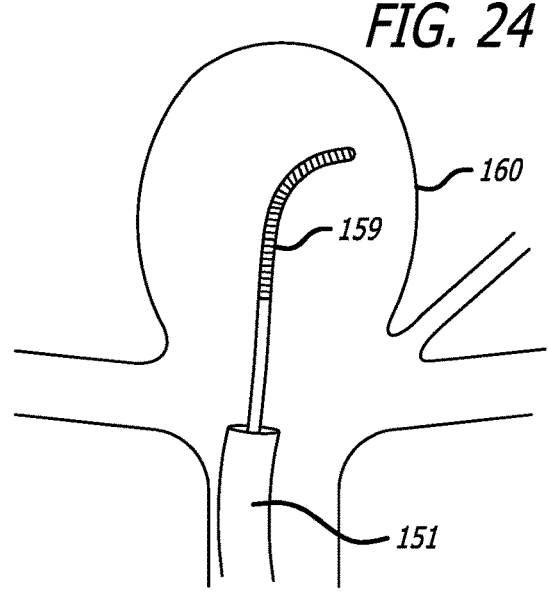

Once a properly sized device 10 has been selected, the delivery and deployment process may then proceed. It should also be noted also that the properties of the device embodiments 10 and delivery system embodiments 112 discussed herein generally allow for retraction of a device 10 after initial deployment into a defect 160, but before detachment of the device 10. Therefore, it may also be possible and desirable to withdraw or retrieve an initially deployed device 10 after the fit within the defect 160 has been evaluated in favor of a differently sized device 10. An example of a terminal aneurysm 160 is shown in FIG. 23 in section. The tip 151 of a catheter, such as a microcatheter 61 may be advanced into or adjacent the vascular site or defect 160 (e.g., aneurysm) as shown in FIG. 24. For some embodiments, an embolic coil or other vaso-occlusive device or material 176 (as shown for example in FIG. 19) may optionally be placed within the aneurysm 160 to provide a framework for receiving the device 10. In addition, a stent 173 may be placed within a parent vessel 174 of some aneurysms substantially crossing the aneurysm neck prior to or during delivery of devices for treatment of a patient's vasculature discussed herein (also as shown for example in FIG. 19). An example of a suitable microcatheter 61 having an inner lumen diameter of about 0.020 inches to about 0.022 inches is the Rapid Transit® manufactured by Cordis Corporation. Examples of some suitable microcatheters 61 may include microcatheters having an inner lumen diameter of about 0.026 inch to about 0.028 inch, such as the Rebar® by Ev3 Company, the Renegade Hi-Flow® by Boston Scientific Corporation, and the Mass Transit® by Cordis Corporation. Suitable microcatheters having an inner lumen diameter of about 0.031 inch to about 0.033 inch may include the Marksmen® by Chestnut Medical Technologies, Inc. and the Vasco 28® by Balt Extrusion. A suitable microcatheter 61 having an inner lumen diameter of about 0.039 inch to about 0.041 inch includes the Vasco 35 by Balt Extrusion. These microcatheters 61 are listed as exemplary embodiments only, other suitable microcatheters may also be used with any of the embodiments discussed herein.

Figure 25:
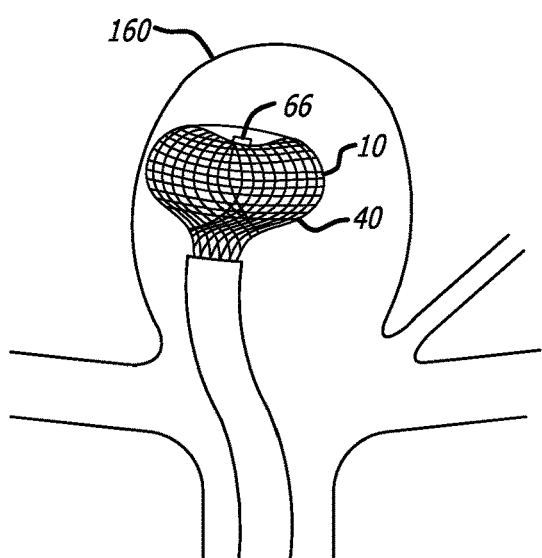

Detachment of the device 10 from the delivery apparatus 110 may be controlled by a control switch 188 disposed at a proximal end of the delivery system 112, which may also be coupled to an energy source 142, which severs the tether 72 that secures the proximal hub 68 of the device 10 to the delivery apparatus 110. While disposed within the microcatheter 61 or other suitable delivery system 112, as shown in FIG. 11, the filaments 14 of the permeable shell 40 may take on an elongated, non-everted configuration substantially parallel to each other and a longitudinal axis of the catheter 61. Once the device 10 is pushed out of the distal port of the microcatheter 61, or the radial constraint is otherwise removed, the distal ends 62 of the filaments 14 may then axially contract towards each other so as to assume the globular everted configuration within the vascular defect 160 as shown in FIG. 25.

The device 10 may be inserted through the microcatheter 61 such that the catheter lumen 120 restrains radial expansion of the device 10 during delivery. Once the distal tip or deployment port of the delivery system 112 is positioned in a desirable location adjacent or within a vascular defect 160, the device 10 may be deployed out the distal end of the catheter 61 thus allowing the device to begin to radially expand as shown in FIG. 25. As the device 10 emerges from the distal end of the delivery system 112, the device 10 expands to an expanded state within the vascular defect 160, but may be at least partially constrained by an interior surface of the vascular defect 160.

Figure 26:
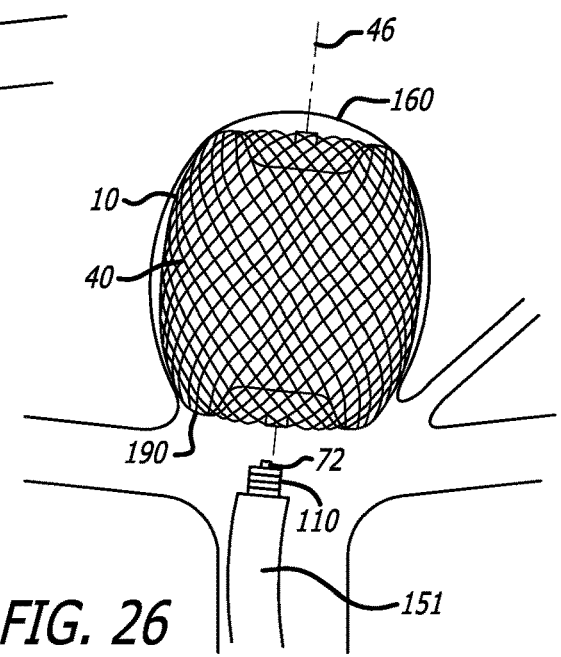

Upon full deployment, radial expansion of the device 10 may serve to secure the device 10 within the vascular defect 160 and also deploy the permeable shell 40 across at least a portion of an opening 190 (e.g., aneurysm neck) so as to at least partially isolate the vascular defect 160 from flow, pressure or both of the patient's vasculature adjacent the vascular defect 160 as shown in FIG. 26. The conformability of the device 10, particularly in the neck region 190 may provide for improved sealing. For some embodiments, once deployed, the permeable shell 40 may substantially slow flow of fluids and impede flow into the vascular site and thus reduce pressure within the vascular defect 160. For some embodiments, the device 10 may be implanted substantially within the vascular defect 160, however, in some embodiments, a portion of the device 10 may extend into the defect opening or neck 190 or into branch vessels.

One exemplary case study that has been conducted includes a procedure performed on a female canine where an aneurysm was surgically created in the subject canine. The target aneurysm prior to treatment had a maximum transverse dimension of about 8 mm, a length of about 10 mm and a neck measurement of about 5.6 mm. The device 10 deployed included a permeable shell 40 formed of 144 resilient filaments having a transverse diameter of about 0.0015 inches braided into a globular structure having a transverse dimension of about 10 mm and a longitudinal length of about 7 mm in a relaxed expanded state. The maximum size 100 of the pores 64 of the expanded deployed permeable shell 40 was about 0.013 inches. The device was delivered to the target aneurysm using a 5 Fr. Guider Softip XF guide catheter made by Boston Scientific. The maximum size 100 of the pores 64 of the portion of the expanded deployed permeable shell 40 that spanned the neck of the aneurysm again was about 0.013 inches. Five minutes after detachment from the delivery system, the device 10 had produced acute occlusion of the aneurysm.

Another exemplary case study conducted involved treatment of a surgically created aneurysm in a New Zealand White Rabbit. The target aneurysm prior to treatment had a maximum transverse dimension of about 3.6 mm, length of about 5.8 mm and a neck measurement of about 3.4 mm. The device 10 deployed included a permeable shell formed of 144 resilient filaments having a transverse diameter of about 0.001 inches braided into a globular structure having a transverse dimension of about 4 mm and a length of about 5 mm in a relaxed expanded state. The pore size 100 of the portion of the braided mesh of the expanded deployed permeable shell 40 that was configured to span the neck of the vascular defect was about 0.005 inches. The device was delivered to the surgically created aneurysm with a 5 Fr. Envoy STR guide catheter manufactured by Cordis Neurovascular. A Renegade Hi-Flo microcatheter manufactured by Boston Scientific having an inner lumen diameter of about 0.027 inches was then inserted through the guide catheter and served as a conduit for delivery of the device 10 secured to a distal end of a delivery apparatus. Once the device 10 was deployed within the vascular defect 160, the vascular defect 160 achieved at least partial occlusion at 5 minutes from implantation. However, due to the sensitivity of the subject animal to angiographic injection and measurement, no further data was taken during the procedure. Complete occlusion was observed for the device when examined at 3 weeks from the procedure.

For some embodiments, as discussed above, the device 10 may be manipulated by the user to position the device 10 within the vascular site or defect 160 during or after deployment but prior to detachment. For some embodiments, the device 10 may be rotated in order to achieve a desired position of the device 10 and, more specifically, a desired position of the permeable shell 40, prior to or during deployment of the device 10. For some embodiments, the device 10 may be rotated about a longitudinal axis of the delivery system 112 with or without the transmission or manifestation of torque being exhibited along a middle portion of a delivery catheter being used for the delivery. It may be desirable in some circumstances to determine whether acute occlusion of the vascular defect 160 has occurred prior to detachment of the device 10 from the delivery apparatus 110 of the delivery system 112. These delivery and deployment methods may be used for deployment within berry aneurysms, terminal aneurysms, or any other suitable vascular defect embodiments 160. Some method embodiments include deploying the device 10 at a confluence of three vessels of the patient's vasculature that form a bifurcation such that the permeable shell 40 of the device 10 substantially covers the neck of a terminal aneurysm. Once the physician is satisfied with the deployment, size and position of the device 10, the device 10 may then be detached by actuation of the control switch 188 by the methods described above and shown in FIG. 26. Thereafter, the device 10 is in an implanted state within the vascular defect 160 to effect treatment thereof.

Figure 27:
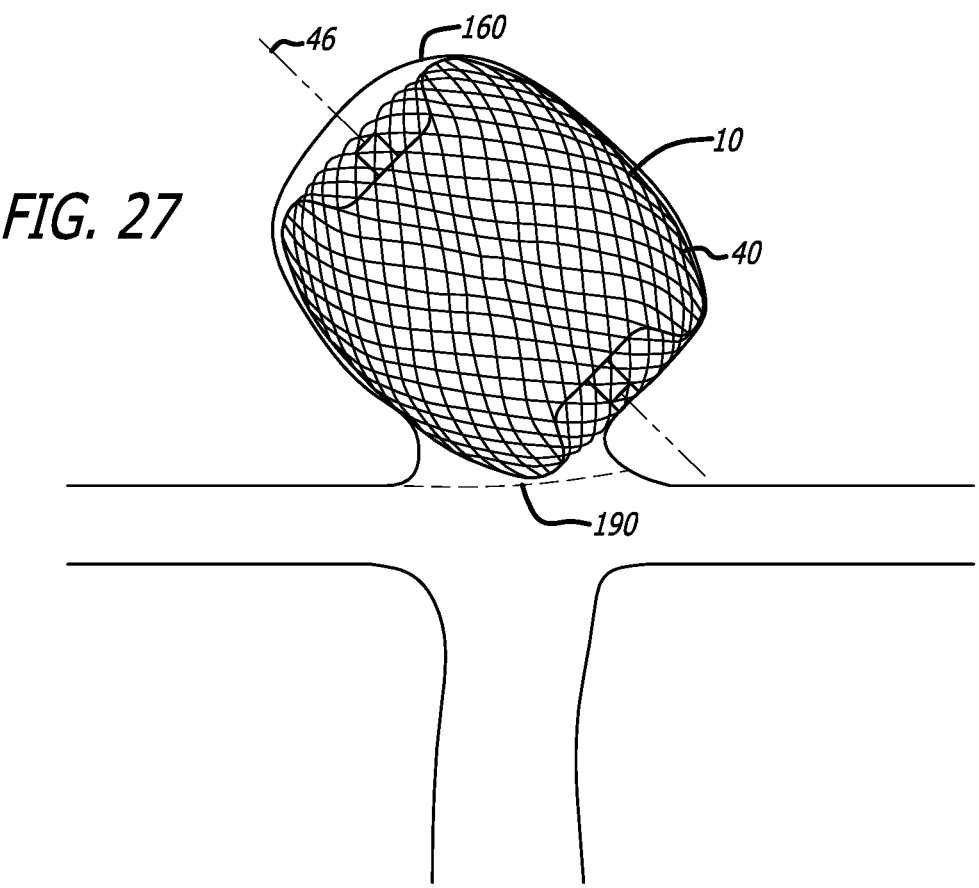
FIG. 27 is an elevation view in partial section of an embodiment of a device for treatment of a patient's vasculature deployed within an aneurysm at a tilted angle.

FIG. 27 illustrates another configuration of a deployed and implanted device in a patient's vascular defect 160. While the implantation configuration shown in FIG. 26 indicates a configuration whereby the longitudinal axis 46 of the device 10 is substantially aligned with a longitudinal axis of the defect 160, other suitable and clinically effective implantation embodiments may be used. For example, FIG. 27 shows an implantation embodiment whereby the longitudinal axis 46 of the implanted device 10 is canted at an angle of about 10 degrees to about 90 degrees relative to a longitudinal axis of the target vascular defect 160. Such an alternative implantation configuration may also be useful in achieving a desired clinical outcome with acute occlusion of the vascular defect 160 in some cases and restoration of normal blood flow adjacent the treated vascular defect. FIG. 28 illustrates a device 10 implanted in an irregularly shaped vascular defect 160. The aneurysm 160 shown has at least two distinct lobes 192 extending from the main aneurysm cavity. The two lobes 192 shown are unfilled by the deployed vascular device 10, yet the lobes 192 are still isolated from the parent vessel of the patient's body due to the occlusion of the aneurysm neck portion 190. Markers, such as radiopaque markers, on the device 10 or delivery system 112 may be used in conjunction with external imaging equipment (e.g., x-ray) to facilitate positioning of the device or delivery system during deployment. Once the device is properly positioned, the device 10 may be detached by the user. For some embodiments, the detachment of the device 10 from the delivery apparatus 110 of the delivery system 112 may be affected by the delivery of energy (e.g., heat, radiofrequency, ultrasound, vibrational, or laser) to a junction or release mechanism between the device 10 and the delivery apparatus 110. Once the device 10 has been detached, the delivery system 112 may be withdrawn from the patient's vasculature or patient's body 158. For some embodiments, a stent 173 may be placed within the parent vessel substantially crossing the aneurysm neck 190 after delivery of the device 10 as shown in FIG. 19 for illustration.

For some embodiments, a biologically active agent or a passive therapeutic agent may be released from a responsive material component of the device 10. The agent release may be affected by one or more of the body's environmental parameters or energy may be delivered (from an internal or external source) to the device 10. Hemostasis may occur within the vascular defect 160 as a result of the isolation of the vascular defect 160, ultimately leading to clotting and substantial occlusion of the vascular defect 160 by a combination of thrombotic material and the device 10. For some embodiments, thrombosis within the vascular defect 160 may be facilitated by agents released from the device 10 and/or drugs or other therapeutic agents delivered to the patient.

For some embodiments, once the device 10 has been deployed, the attachment of platelets to the permeable shell 40 may be inhibited and the formation of clot within an interior space of the vascular defect 160, device, or both promoted or otherwise facilitated with a suitable choice of thrombogenic coatings, anti-thrombogenic coatings or any other suitable coatings (not shown) which may be disposed on any portion of the device 10 for some embodiments, including an outer surface of the filaments 14 or the hubs 66 and 68. Such a coating or coatings may be applied to any suitable portion of the permeable shell 40. Energy forms may also be applied through the delivery apparatus 110 and/or a separate catheter to facilitate fixation and/or healing of the device 10 adjacent the vascular defect 160 for some embodiments. One or more embolic devices or embolic material 176 may also optionally be delivered into the vascular defect 160 adjacent permeable shell portion that spans the neck or opening 190 of the vascular defect 160 after the device 10 has been deployed. For some embodiments, a stent or stent-like support device 173 may be implanted or deployed in a parent vessel adjacent the defect 160 such that it spans across the vascular defect 160 prior to or after deployment of the vascular defect treatment device 10.

In any of the above embodiments, the device 10 may have sufficient radial compliance so as to be readily retrievable or retractable into a typical microcatheter 61. The proximal portion of the device 10, or the device as a whole for some embodiments, may be engineered or modified by the use of reduced diameter filaments, tapered filaments, or filaments oriented for radial flexure so that the device 10 is retractable into a tube that has an internal diameter that is less than about 0.7 mm, using a retraction force less than about 2.7 Newtons (0.6 lbf) force. The force for retrieving the device 10 into a microcatheter 61 may be between about 0.8 Newtons (0.18 lbf) and about 2.25 Newtons (0.5 lbf).

Figure 29:
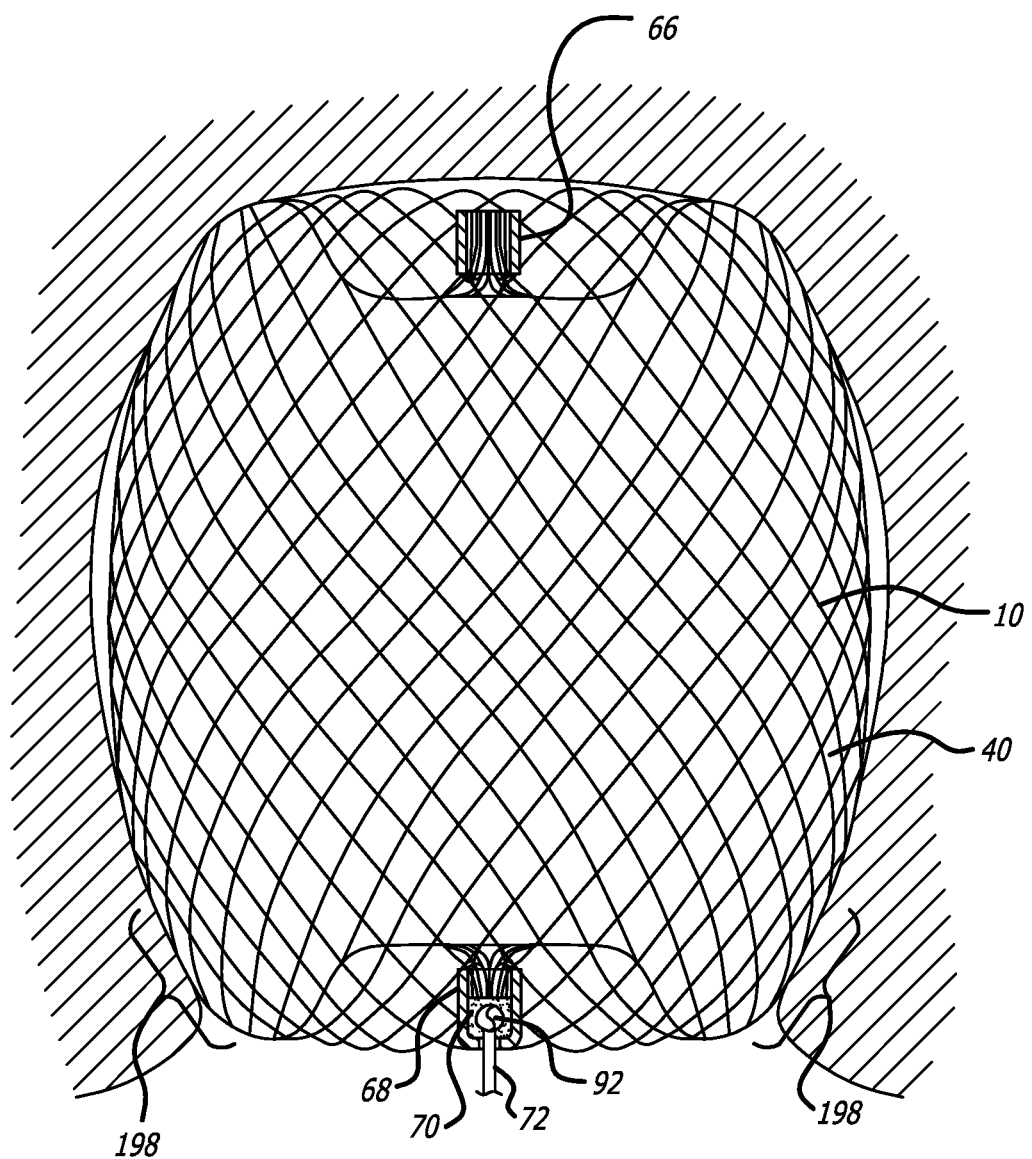
FIG. 29 shows an elevation view in section of a device for treatment of a patient's vasculature deployed within a vascular defect aneurysm.

Engagement of the permeable shell 40 with tissue of an inner surface of a vascular defect 160, when in an expanded relaxed state, may be achieved by the exertion of an outward radial force against tissue of the inside surface of the cavity of the patient's vascular defect 160 as shown in FIG. 29. A similar outward radial force may also be applied by a proximal end portion and permeable shell 40 of the device 10 so as to engage the permeable shell 40 with an inside surface or adjacent tissue of the vascular defect 160. Such forces may be exerted in some embodiments wherein the nominal outer transverse dimension or diameter of the permeable shell 40 in the relaxed unconstrained state is larger than the nominal inner transverse dimension of the vascular defect 160 within which the device 10 is being deployed, i.e., oversizing as discussed above. The elastic resiliency of the permeable shell 40 and filaments 14 thereof may be achieved by an appropriate selection of materials, such as superelastic alloys, including nickel titanium alloys, or any other suitable material for some embodiments. The conformability of a proximal portion of the permeable shell 40 of the device 10 may be such that it will readily ovalize to adapt to the shape and size of an aneurysm neck 190, as shown in FIGS. 20-22, thus providing a good seal and barrier to flow around the device. Thus the device 10 may achieve a good seal, substantially preventing flow around the device without the need for fixation members that protrude into the parent vessel.

Figure 30:
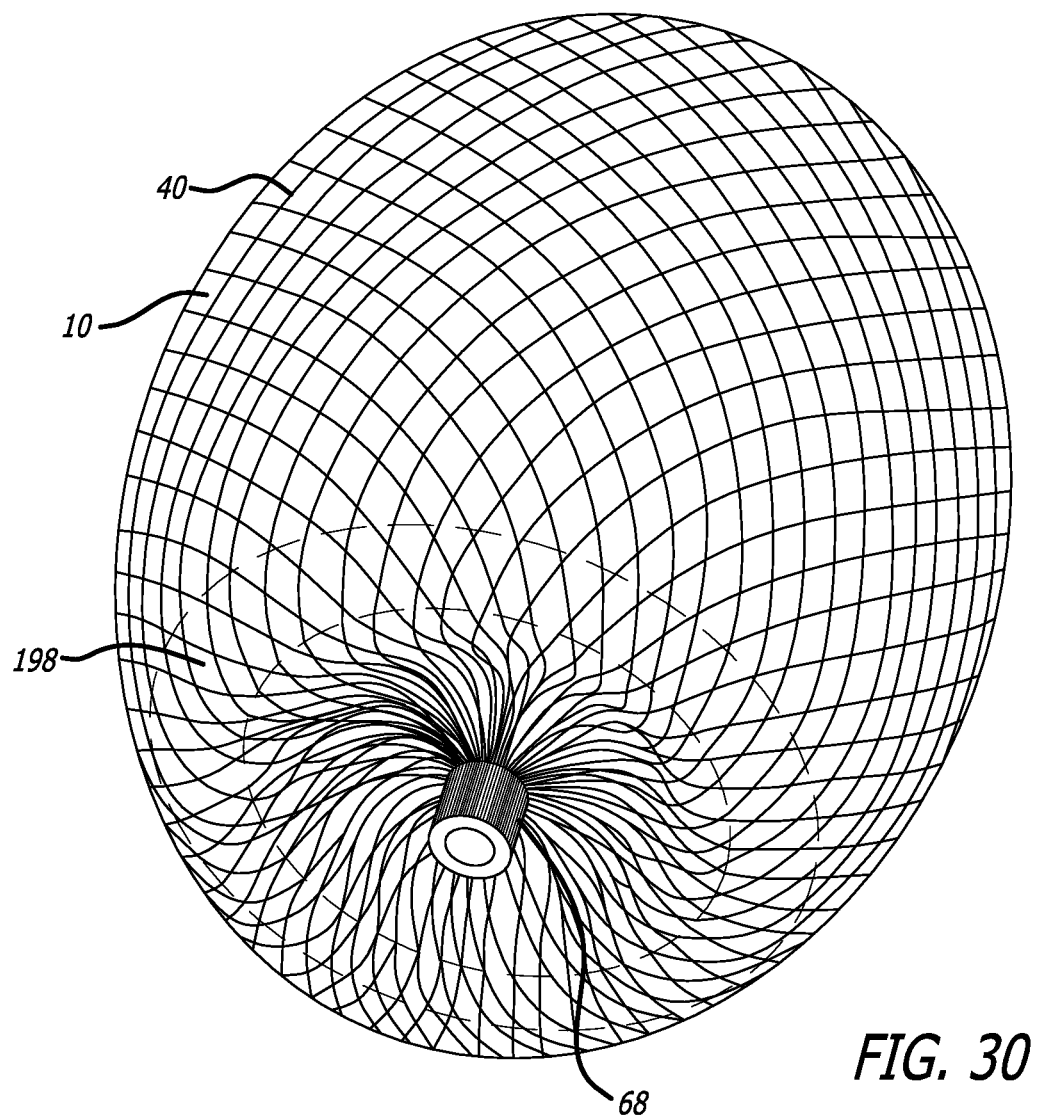
FIG. 30 shows a proximal perspective view of an embodiment of a device for treatment of a patient's vasculature with a sealing zone embodiment indicated by a set of dashed lines.

Some implanted device embodiments 10 have the ends of the filaments 14 of the permeable shell 40 disposed even with or just within a plane formed by the apices of the filaments disposed adjacent to the ends. Some embodiments of the device 10 may also include a sealing member disposed within or about a perimeter zone 198 or other suitable portion of the permeable shell 40 and be configured to facilitate the disruption of flow, a fibrotic tissue response, or physically form a seal between the permeable shell 40 and a surface of the patient's vasculature. The sealing member may comprise coatings, fibers or surface treatments as described herein. The sealing member may be in a part or all of an area of the periphery of the device adjacent where the device contacts the wall of the aneurysm near the aneurysm neck (sealing zone 198) as shown in FIGS. 29 and 30. The zone may extend from about the apex of the outer proximal end radius 88 for a distance up to about 20% of the height of the expanded device 10. The sealing zone 198 may include between about 5% and 30% of the device 10 surface area. Since the flow of blood into an aneurysm 160 generally favors one side of the opening, the sealing member may be incorporated in or attached to the permeable shell 40 structure throughout the peripheral area (sealing zone 198) shown in FIG. 30. Some embodiments of the sealing member may include a swellable polymer. In some embodiments, the sealing member may include or bioactive material or agent such as a biologic material or biodegradable, bioresorbable or other bioactive polymer or copolymers thereof.

Any embodiment of devices for treatment of a patient's vasculature 10, delivery system 112 for such devices 10 or both discussed herein may be adapted to deliver energy to the device for treatment of a patient's vasculature or to tissue surrounding the device 10 at the implant site for the purpose of facilitating fixation of a device 10, healing of tissue adjacent the device or both. In some embodiments, energy may be delivered through a delivery system 112 to the device 10 for treatment of a patient's vasculature such that the device 10 is heated. In some embodiments, energy may be delivered via a separate elongate instrument (e.g., catheter, not shown) to the device 10 for treatment of a patient's vasculature and/or surrounding tissue at the site of the implant 154. Examples of energy embodiments that may be delivered include but are not limited to light energy, thermal or vibration energy, electromagnetic energy, radio frequency energy and ultrasonic energy. For some embodiments, energy delivered to the device 10 may trigger the release of chemical or biologic agents to promote fixation of a device for treatment of a patient's vasculature 10 to a patient's tissue, healing of tissue disposed adjacent such a device 10 or both.

The permeable shell 40 of some device embodiments 10 may also be configured to react to the delivery of energy to effect a change in the mechanical or structural characteristics, deliver drugs or other bioactive agents or transfer heat to the surrounding tissue. For example, some device embodiments 10 may be made softer or more rigid from the use of materials that change properties when exposed to electromagnetic energy (e.g., heat, light, or radio frequency energy). In some cases, the permeable shell 40 may include a polymer that reacts in response to physiologic fluids by expanding. An exemplary material is described by Cox in U.S. Patent Publication No. 2004/0186562, filed Jan. 22, 2004, titled "Aneurysm Treatment Device and Method of Use," which is incorporated by reference herein in its entirety.

Figure 31:
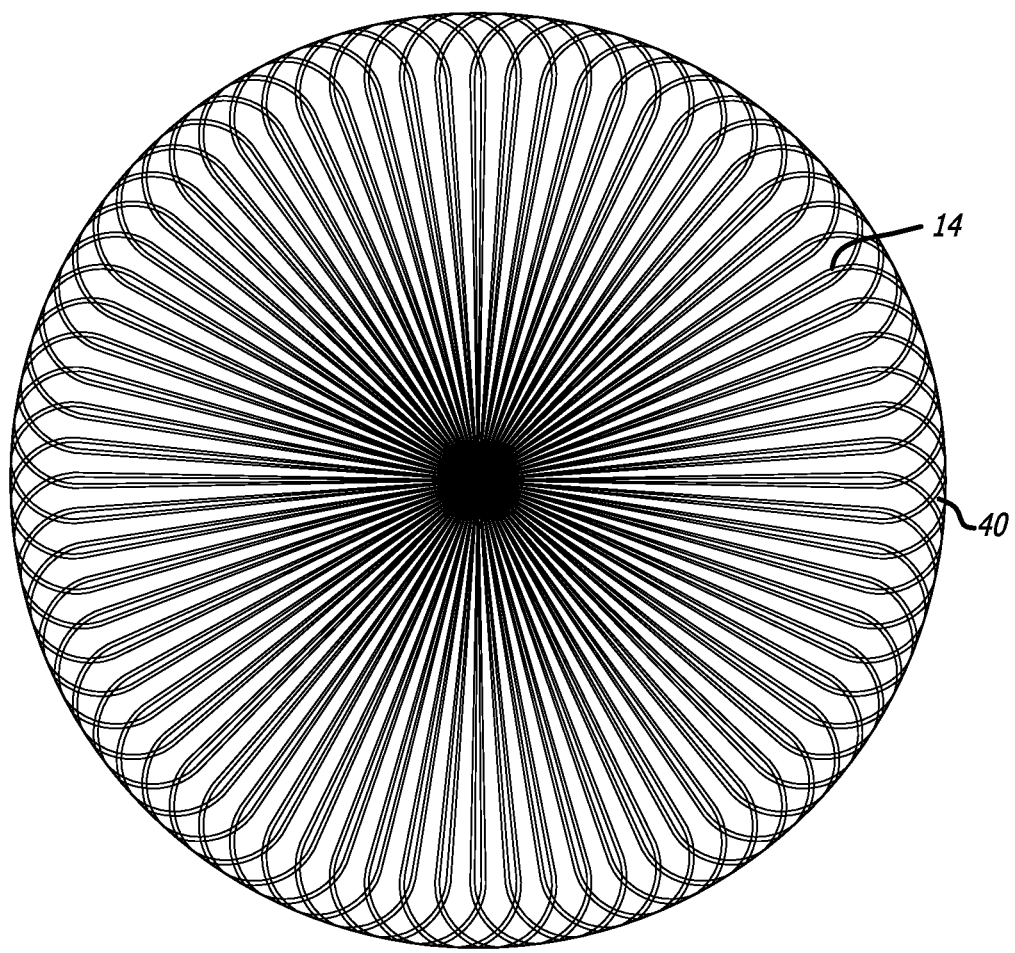
FIGS. 31-35 illustrate various different embodiments of braiding patterns that may be used for permeable shells of devices for treatment of a patient's vasculature.
Figure 32:
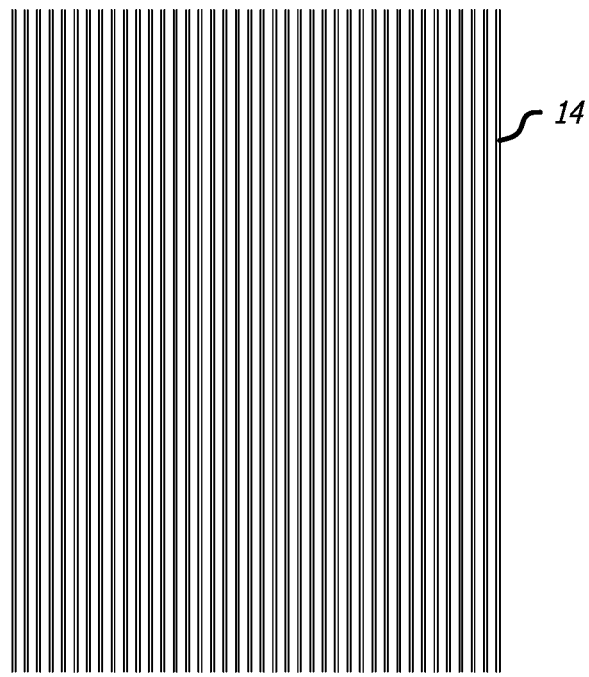
Figure 33:
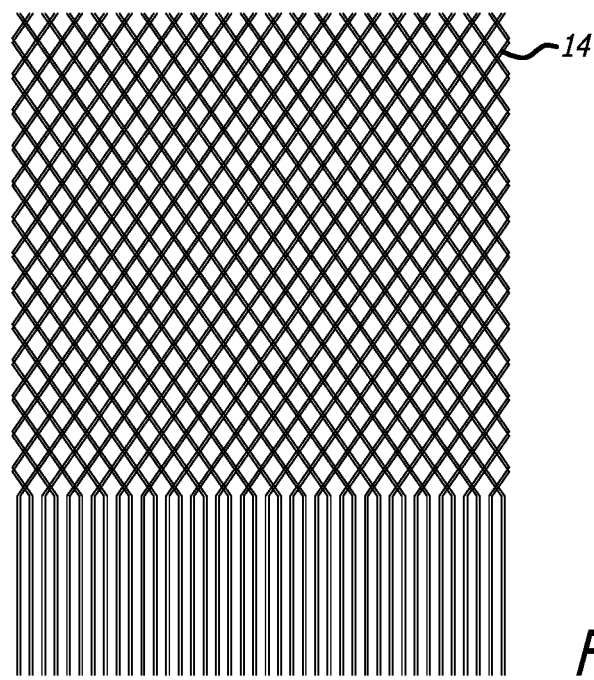
Figure 34:
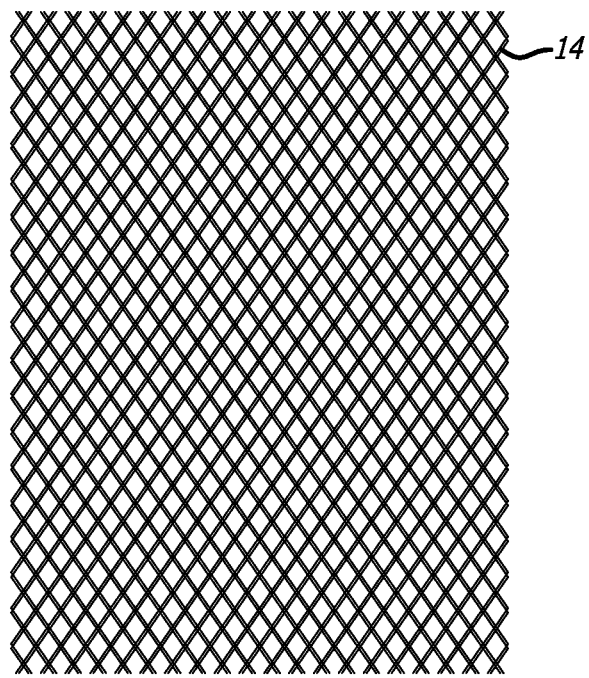

Device embodiments 10 and components thereof discussed herein may take on a large variety of configurations to achieve specific or generally desirable clinical results. In some device embodiments 10, the start of the braided structure of the permeable shell 40 may be delayed from the proximal hub 68 so that the filaments 1 emanate from the proximal hub 68 in a spoke-like radial fashion as shown in the proximal end view of a device in FIG. 31. A flattened analog version of the braid pattern of FIG. 31 is also shown in FIG. 33. This configuration may result in a smaller width gap between the filaments 14 at a given radial distance from the proximal hub 68 relative to a fully braided configuration, the flattened analog pattern of which is shown in FIG. 34. This may provide better flow disruption and promote hemostasis in the area of the device 10 that may be subjected to the highest flow rates. FIG. 32 illustrates a flattened analog representation of a non-braided filament structure for reference.

Figure 35:
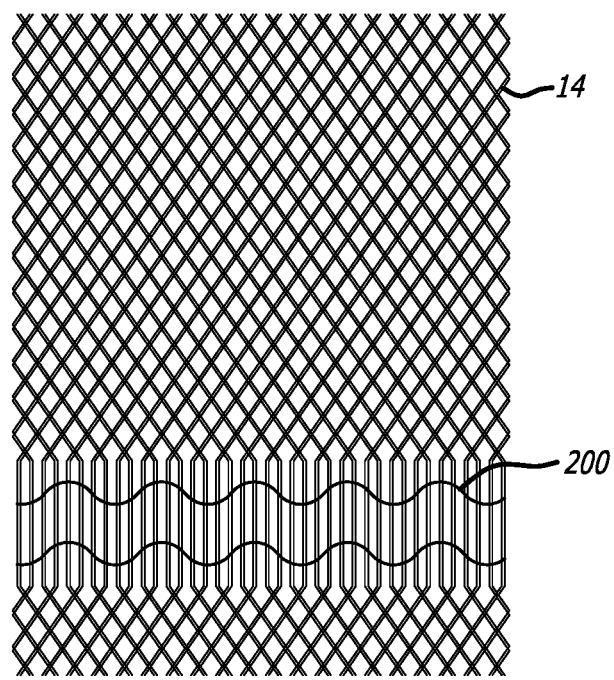

The woven structure may include a portion where the weave or braid of the filaments 14 is interrupted as shown in a flat pattern analog pattern in FIG. 35. In the interrupted region, the filaments 14 may be substantially parallel to each other. The interrupted area may provide a region with different mechanical characteristics such as radial stiffness and/or compliance. Further, the interrupted region may allow for the addition of non-structural fibers or sealing members 200 as described herein or other elements to facilitate fixation, healing, fibrosis or thrombosis. The interrupted region may be within, part of or adjacent to the sealing member zone 198 as shown in FIGS. 29 and 30. The interrupted region may be less than about 50% of the surface area and may be between about 5% and 25% of the surface area.

Figure 36:
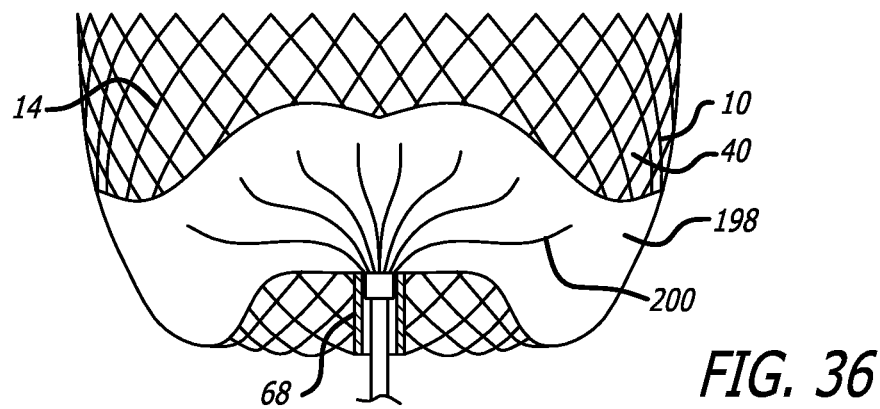
FIG. 36 illustrates a device for treatment of a patient's vasculature that includes non-structural fibers in the permeable shell structure of the device.
Figure 37:
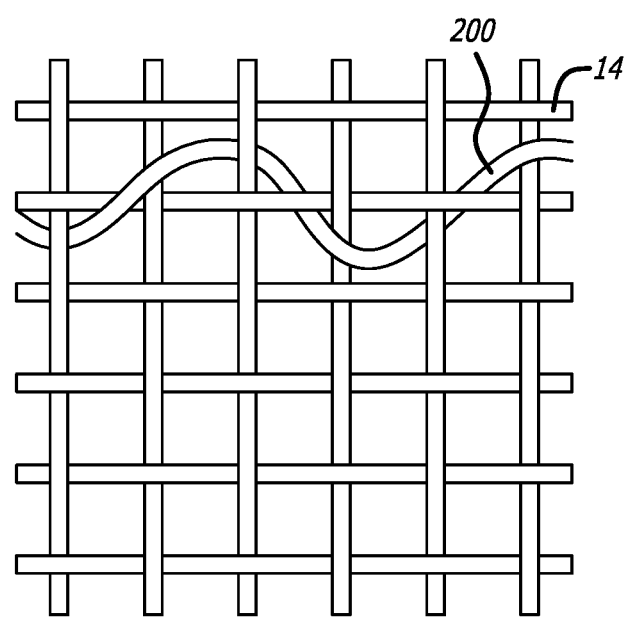
FIG. 37 is an enlarged view of non-structural fibers woven into filaments of a permeable shell structure.

In some embodiments, filamentary or fibrous members that are substantially non-structural may be attached or interwoven into the structural filaments of a portion of the permeable shell to increase a resistance to the flow of blood through the permeable shell structure 40. In some embodiments, a plurality of fibers 200 may be attached on the inner surface of the permeable shell 40 near the proximal hub 68 as shown in FIG. 36. The fibrous members 200 may be the fibers that form the detachment system tether for some embodiments. In some embodiments, one or more fibers 200 may be interwoven into the permeable shell filaments 14 as shown in FIG. 37. The non-structural fibers 200, which may be microfibers or any other suitable fibers, may be polymeric. The non-structural fibers 200 may include, but not limited to, any of the fibers or microfibers discussed or incorporated herein.

In some cases, device embodiments for treatment of a patient's vasculature 10 may generally be fabricated by braiding a substantially tubular braided structure with filamentary elements 14, forming the braided tubular structure into a desired shape, and heat setting the braided formed filaments into the desired shape. Once so formed, the ends of the elongate resilient filaments 14 may then be secured together relative to each other by any of the methods discussed above and proximal and distal hubs 66 and 68 added.

Figure 38:
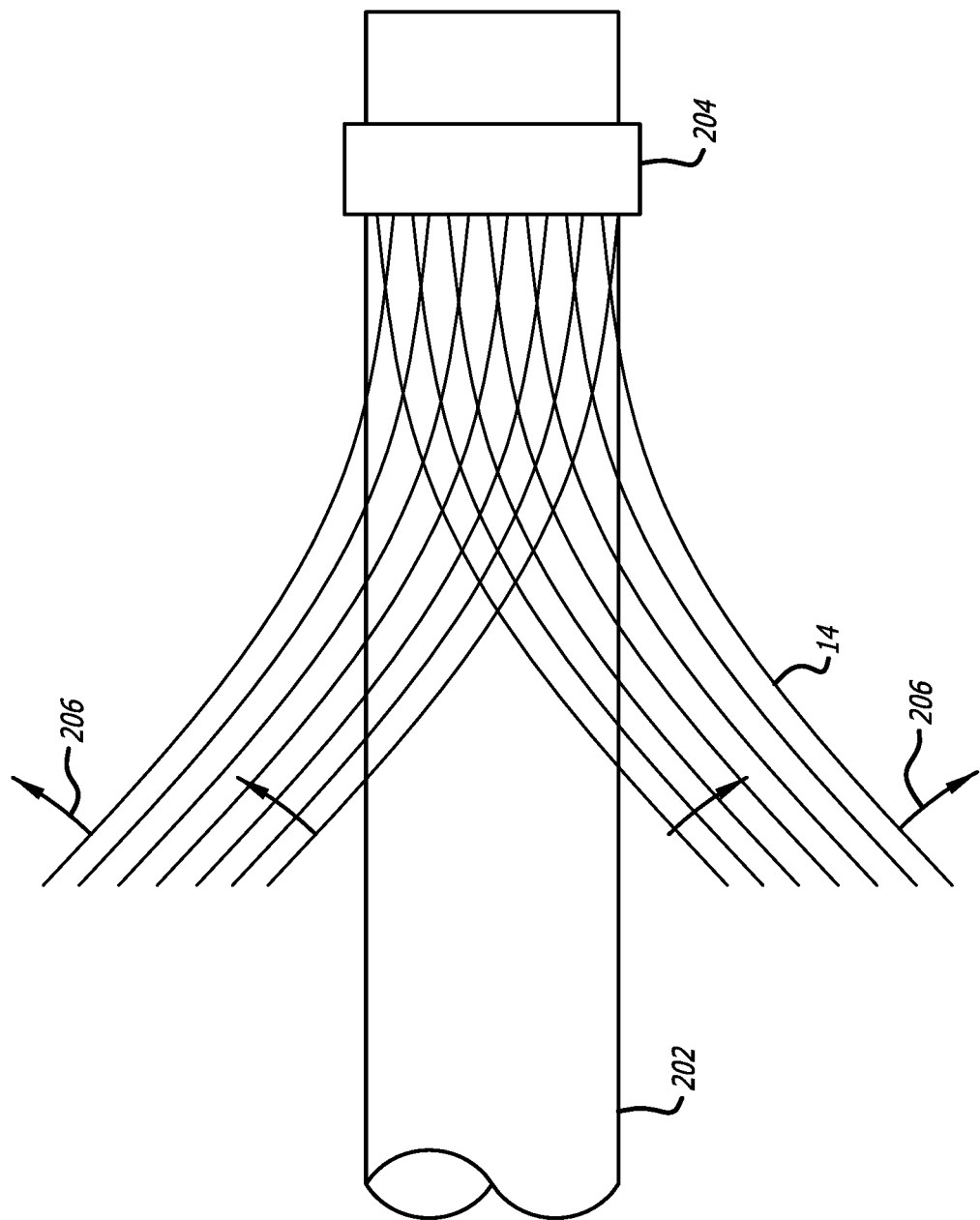
FIG. 38 is an elevation view of a mandrel used for manufacture of a braided tubular member for construction of an embodiment of a device for treatment of a patient's vasculature with the initiation of the braiding process shown.
Figure 39:
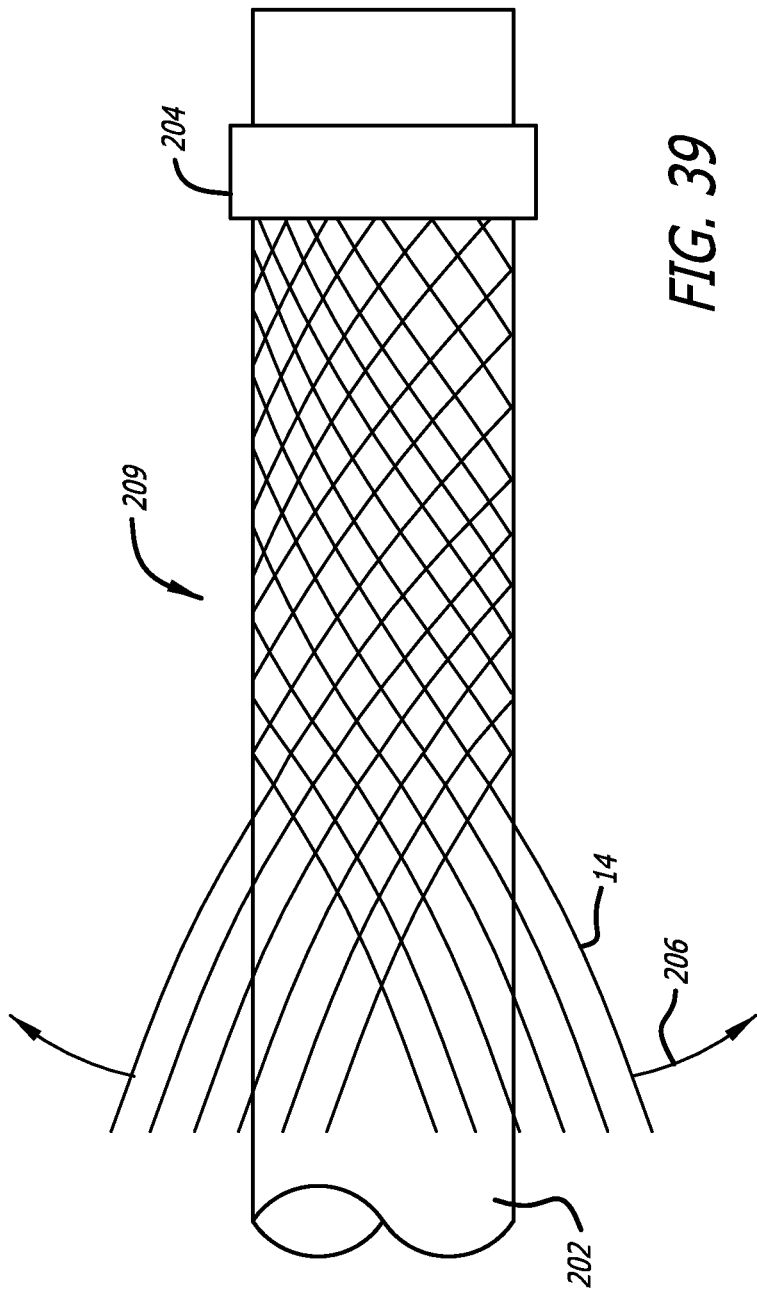
FIG. 39 is an elevation view of a braiding process for a braided tubular member used for manufacture of a device.

Such a braiding process may be carried out by automated machine fabrication or may also be performed by hand. An embodiment of a process for braiding a tubular braided structure by a manual process is shown in FIG. 38. A plurality of elongate resilient filaments 14 are secured at one end of an elongate cylindrical braiding mandrel 202 by a constraining band 204. The band 204 may include any suitable structure that secured the ends of the filaments 14 relative to the mandrel 202 such as a band of adhesive tape, an elastic band, an annular clamp or the like. The loose ends of the filaments 14 opposite the secured ends are being manipulated in a braided or woven pattern as indicated by the arrows 206 to achieve a one over-one under braid pattern for generation of a braided tubular member 208. As discussed above, although a one over-one under simple braid pattern is shown and discussed, other braid or weave patterns may also be used. One such example of another braid configuration may include a two over-one under pattern. FIG. 39 illustrates the braided tubular member 208 taking shape and lengthening as the braiding process continues as indicated by the arrows 206 in FIG. 39. Once the braided tubular member 208 achieves sufficient length, it may be removed from the braiding mandrel 202 and positioned within a shaping fixture such as the shaping fixture embodiments shown in FIGS. 40 and 41.

Figure 40:
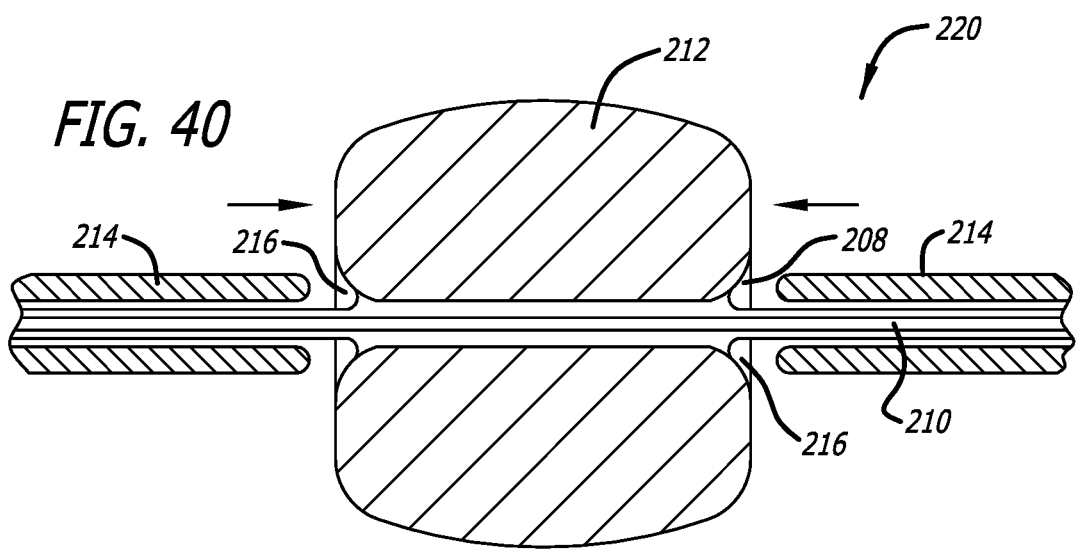
FIG. 40 is an elevation view in partial section of an embodiment of a fixture for heat setting a braided tubular member for manufacture of a device for treatment of a patient's vasculature.

FIG. 40 shows the tubular braided member 208 disposed over an internal rod mandrel 210 that extends through central lumens of an internal ball mandrel 212 and a pair of opposed recessed end forming mandrels 214. The tubular braided member 208 is also disposed over an outer surface of the internal ball mandrel 212 and within an inner lumen of each of the end forming mandrels 214. In order to hold the braided tubular member 208 onto an outer surface contour of the internal ball mandrel 212, including the recessed ends 216 thereof, the end forming mandrels 214 are configured to be pushed against and into the recessed ends 216 of the internal ball mandrel 212 such that the inside surface of the braided tubular member 208 is held against the outer contour of the internal ball mandrel 212 and fixed in place. This entire fixture 220 with the inside surface of the braided tubular structure 208 held against the outside surface of the internal ball mandrel 212 may then be subjected to an appropriate heat treatment such that the resilient filaments 14 of the braided tubular member 208 assume or are otherwise shape-set to the outer contour of the central ball mandrel 212. In some embodiments, the filamentary elements 14 of the permeable shell 40 may be held by a fixture configured to hold the permeable shell 40 in a desired shape and heated to about 475-525 degrees C. for about 5-10 minutes to shape-set the structure.

The central ball mandrel 212 may be configured to have any desired shape so as to produce a shape set tubular braided member 208 that forms a permeable shell 40 having a desired shape and size such as the globular configuration of the device 10 of FIGS. 3-6 above, or any other suitable configuration. As such, the central ball mandrel 212 may also be a globular-shaped ball with recesses in opposing sides for the hubs 66 and 68 that is placed inside the tubular braid 208. A mold or molds that have one or more pieces that are assembled to form a cavity with the desired device shape may also be used in conjunction with or in place of the end forming mandrels 214. Once the heat set process in complete, fibers, coatings, surface treatments may be added to certain filaments, portions of filaments, or all of the permeable shell 40 structure that results. Further, for some embodiments of device processing, the permeable shell 40 may be formed as discussed above by securing proximal ends 60 and distal ends 62 of elongate filamentary elements 14, or to respective proximal and distal hubs 66 and 68.

Figure 41:
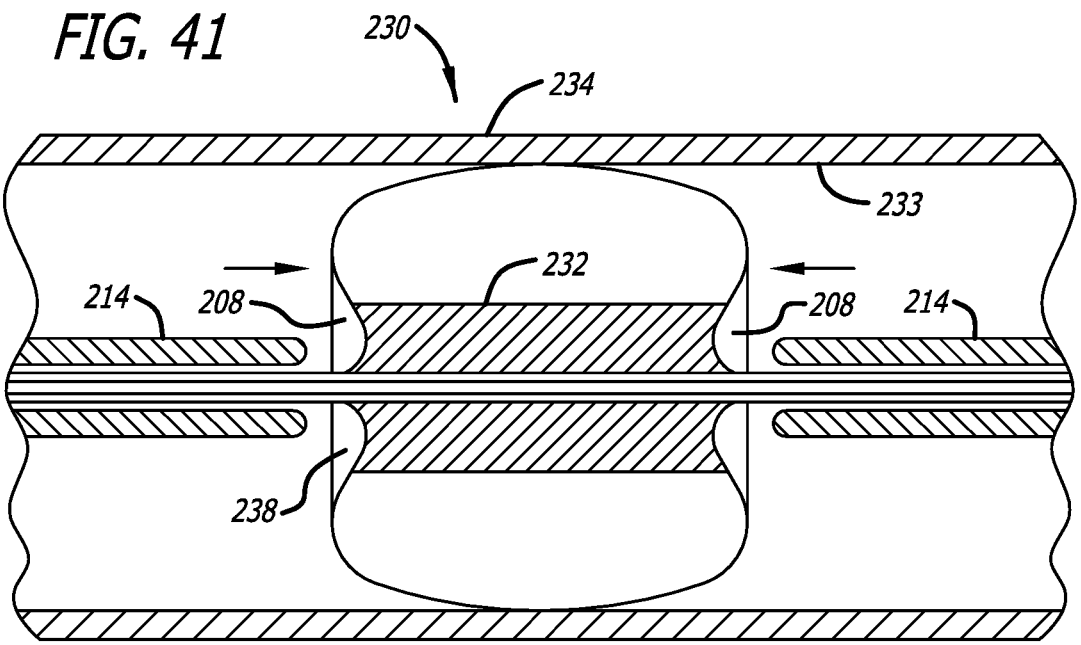
FIG. 41 is an elevation view in partial section of an embodiment of a fixture for heat setting a braided tubular member for manufacture of a device for treatment of a patient's vasculature.

FIG. 41 shows another embodiment of a fixture for shape setting the permeable shell 40 of a device for treatment of a patient's vasculature. The fixture embodiment 230 of FIG. 41 may be used in essentially the same manner as the fixture embodiment 220 of FIG. 40, except that instead of a central ball mandrel 212, an internal tube mandrel 232 is used in conjunction with an external tube restraint 234 in order to hold the shape of the braided tubular member 208 during the heat setting process. More specifically, the tubular braided member 208 is disposed over an internal rod mandrel 210 that extends through central lumens of the internal tube mandrel 232 and a pair of opposed recessed end forming mandrels 214. The tubular braided member 208 is also disposed over an outer surface of the internal tube mandrel 232 and within an inner lumen of each of the end forming mandrels 214.

In order to hold the braided tubular member 208 into a desired shape, including the recessed ends thereof, the end forming mandrels 214 are configured to be pushed against and into recessed ends 238 of the internal tube mandrel 232 such that the inside surface of the braided tubular member 208 is held against the outer contour of the internal tube mandrel 232 and fixed in place at the ends of the tube mandrel 232. Between the ends of the tube mandrel 232, the braided tubular member 208 radially expands outwardly until it touches and is radially constrained by an inside surface of an external tube mandrel 234. The combination of axial restraint and securement of the braided tubular member 208 at the ends of the internal tube mandrel 232 in conjunction with the inward radial restraint on an outside surface of the braided tubular member 208 disposed between the proximal and distal ends thereof, may be configured to produce a desired globular configuration suitable for the permeable shell 40 of the device 10.

Once again, this entire fixture 230 with the inside surface of the ends of the braided tubular structure 208 held against the outside surface of the ends of the internal tube mandrel 232 and an outside surface of the braided tubular member 208 radially constrained by an inside surface 233 of the external tube member 234, may then be subjected to an appropriate heat treatment. The heat treatment may be configured such that the resilient filaments 14 of the braided tubular member 208 assume or are otherwise shape-set to the globular contour of the filaments 14 generated by the fixture 230. In some embodiments, the filamentary elements 14 of the permeable shell 40 may be held by a fixture configured to hold the braided tubular member 208 in a desired shape and heated to about 475-525 degrees C. for about 5-10 minutes to shape-set the structure. The internal tube mandrel 232 and inside surface 233 of the external tube member 234 may be so configured to have any desired shape so as to produce a shape set tubular braided member 208 that forms a permeable shell 40 having a desired shape and size such as the globular configuration of the device of FIGS. 3-6 above, or any other suitable configuration.

For some embodiments, material may be attached to filaments 14 of the permeable shell 40 of a device 10 such that it substantially reduces the size of the fenestrations, cells or pores 64 between filaments 14 and thus reduces the porosity in that area. For example, coating embodiments may be disposed on portions of the filaments 14 to create small fenestrations or cells and thus higher density of the permeable shell 40. Active materials such as a responsive hydrogel may be attached or otherwise incorporated into permeable shell 40 of some embodiments such that it swells upon contact with liquids over time to reduce the porosity of the permeable shell 40.

Device embodiments 10 discussed herein may be coated with various polymers to enhance it performance, fixation and/or biocompatibility. In addition, device embodiments 10 may be made of various biomaterials known in the art of implant devices including but not limited to polymers, metals, biological materials and composites thereof. Device embodiments discussed herein may include cells and/or other biologic material to promote healing. Device embodiments discussed herein may also be constructed to provide the elution or delivery of one or more beneficial drugs, other bioactive substances or both into the blood or the surrounding tissue.

Permeable shell embodiments 40 of devices for treatment of a patient's vasculature 10 may include multiple layers. A first or outer layer may be constructed from a material with low bioactivity and hemocompatibility so as to minimize platelet aggregation or attachment and thus the propensity to form clot and thrombus. Optionally, an outer layer may be coated or incorporate an antithrombogenic agent such as heparin or other antithrombogenic agents described herein or known in the art. One or more inner layers disposed towards the vascular defect in a deployed state relative to the first layer may be constructed of materials that have greater bioactivity and/or promote clotting and thus enhance the formation of an occlusive mass of clot and device within the vascular defect. Some materials that have been shown to have bioactivity and/or promote clotting include silk, polylactic acid (PLA), polyglycolic acid (PGA), collagen, alginate, fibrin, fibrinogen, fibronectin, Methylcellulose, gelatin, Small Intestinal Submucosa (SIS), poly-N-acetylglucosamine and copolymers or composites thereof.

Bioactive agents suitable for use in the embodiments discussed herein may include those having a specific action within the body as well as those having nonspecific actions. Specific action agents are typically proteinaceous, including thrombogenic types and/or forms of collagen, thrombin and fibrogen (each of which may provide an optimal combination of activity and cost), as well as elastin and von Willebrand factor (which may tend to be less active and/or expensive agents), and active portions and domains of each of these agents. Thrombogenic proteins typically act by means of a specific interaction with either platelets or enzymes that participate in a cascade of events leading eventually to clot formation. Agents having nonspecific thrombogenic action are generally positively charged molecules, e.g., polymeric molecules such as chitosan, polylysine, poly(ethylenimine) or acrylics polymerized from acrylimide or methacrylamide which incorporate positively-charged groups in the form of primary, secondary, or tertiary amines or quarternary salts, or non-polymeric agents such as (tridodecylmethylammonium chloride). Positively charged hemostatic agents promote clot formation by a non-specific mechanism, which includes the physical adsorption of platelets via ionic interactions between the negative charges on the surfaces of the platelets and the positive charges of the agents themselves.

Device embodiments 10 herein may include a surface treatment or coating on a portion, side or all surfaces that promotes or inhibits thrombosis, clotting, healing or other embolization performance measure. The surface treatment or coating may be a synthetic, biologic or combination thereof. For some embodiments, at least a portion of an inner surface of the permeable shell 40 may have a surface treatment or coating made of a biodegradable or bioresorbable material such as a polylactide, polyglycolide or a copolymer thereof. Another surface treatment or coating material which may enhance the embolization performance of a device includes a polysachharide such as an alginate based material. Some coating embodiments may include extracellular matrix proteins such as ECM proteins. One example of such a coating may be Finale Prohealing coating which is commercially available from Surmodics Inc., Eden Prairie, MN. Another exemplary coating may be Polyzene-F which is commercially available from CeloNovo BioSciences, Inc., Newnan, GA. In some embodiments, the coatings may be applied with a thickness that is less than about 25% of a transverse dimension of the filaments 14.

Antiplatelet agents may include aspirin, glycoprotein IIb/IIIa receptor inhibitors (including, abciximab, eptifibatide, tirofiban, lamifiban, fradafiban, cromafiban, toxifiban, XV454, lefradafiban, klerval, lotrafiban, orbofiban, and xemilofiban), dipyridamole, apo-dipyridamole, persantine, prostacyclin, ticlopidine, clopidogrel, cromafiban, cilostazol, and nitric oxide. To deliver nitric oxide, device embodiments may include a polymer that releases nitric oxide. Device embodiments 10 may also deliver or include an anticoagulant such as heparin, low molecular weight heparin, hirudin, warfarin, bivalirudin, hirudin, argatroban, forskolin, ximelagatran, vapiprost, prostacyclin and prostacyclin analogues, dextran, synthetic antithrombin, Vasoflux, argatroban, efegatran, tick anticoagulant peptide, Ppack, HMG-CoA reductase inhibitors, and thromboxane A2 receptor inhibitors.

In some embodiments, the permeable shell 40 of a device 10 may be coated with a composition that may include nanoscale structured materials or precursors thereof (e.g., self-assembling peptides). The peptides may have with alternating hydrophilic and hydrophobic monomers that allow them to self-assemble under physiological conditions. The composition may comprise a sequence of amino acid residues. In some embodiments, the permeable shell may include a thin metallic film material. The thin film metal may be fabricated by sputter deposition and may be formed in multiple layers. The thin film may be a nickel-titanium alloy also known as nitinol.

Figure 42:
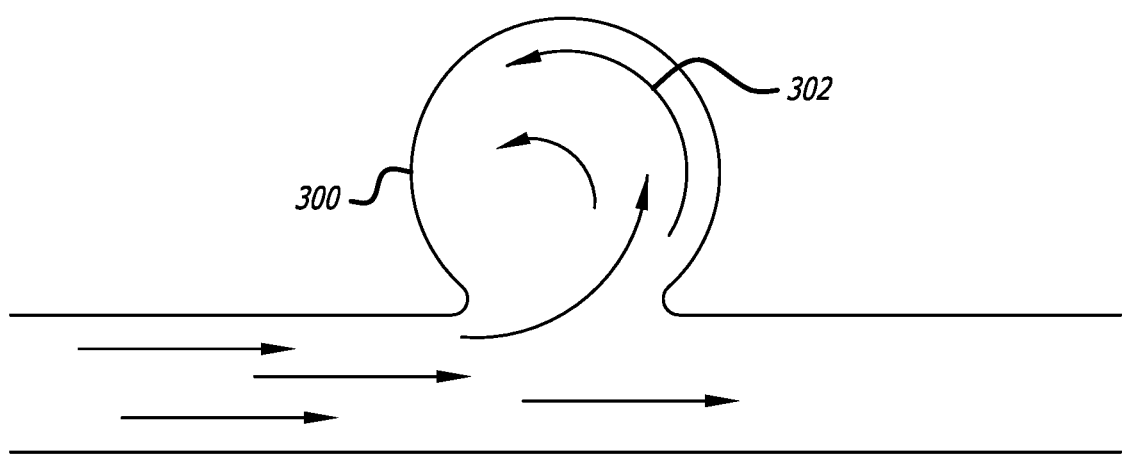
FIG. 42 is an elevation view in section that illustrates a flow of blood within an aneurysm of a patient's vasculature.

In some instances, saccular aneurysms may have a generally circular flow dynamic 302 of blood as shown in FIG. 42. While the shell slows flow into the aneurysm 300, thrombosis and embolization may be further enhanced by an internal porous structure. In particular, a structure that is formed so that the circular flow 302, and in particular the highest velocity region is forced to pass through one or more porous layers may have a synergistic treatment effect and promote rapid thrombosis.

Figure 43:
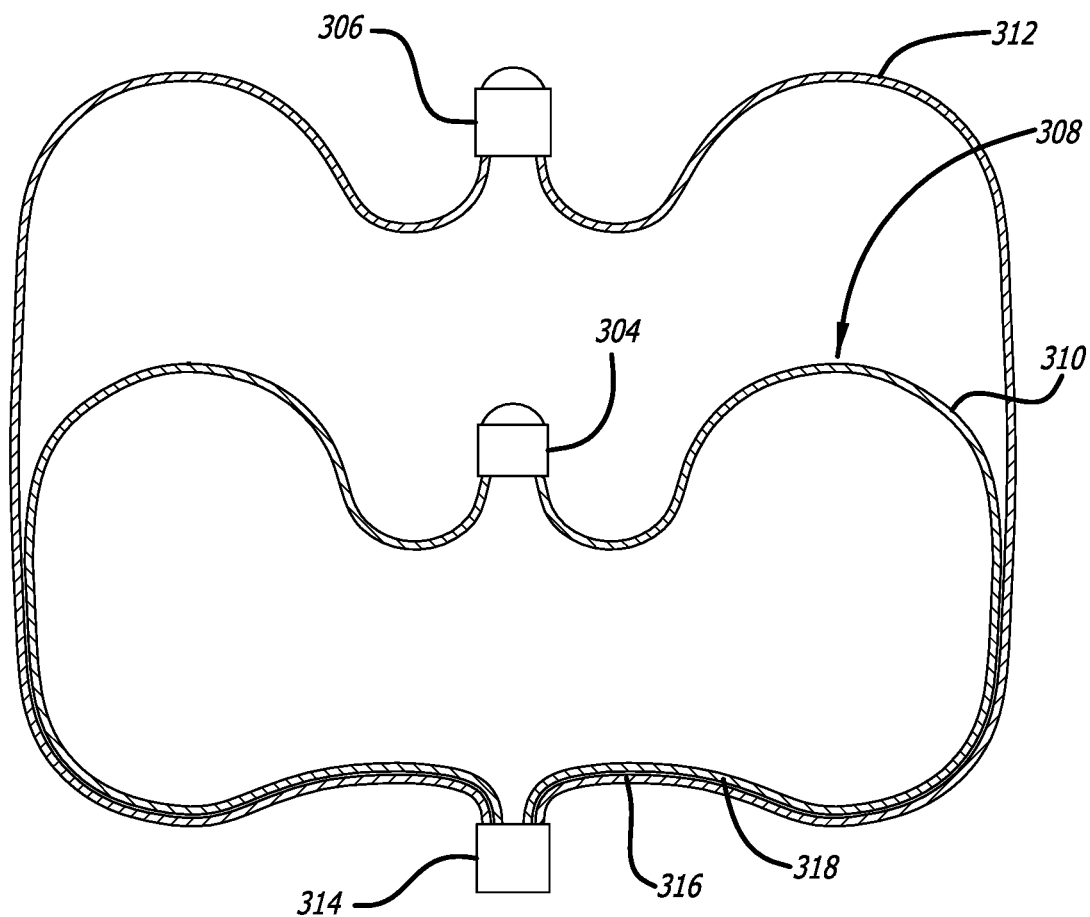
FIG. 43 is an elevation view in partial section of an embodiment of a device for treatment of a patient's vasculature.

In some embodiments, the distal end 308 of the inner layer (or structure) 310 may terminate with a connection or hub 304 as shown in FIG. 43. With an internal termination of the inner structure 310, the potential problem of length matching and buckling may be minimized due to the ability of the inner layer 310 to collapse without affecting, or minimally affecting, the outer layer 312. In some embodiments, the collapsed length of the inner layer or structure 310 may be less than about 80% of the collapsed length of the outer layer or structure 312. A proximal hub 314 is also shown for terminating the proximal end 316 of the outer layer 312 and the proximal end 318 of the inner layer 310.

Figure 44:
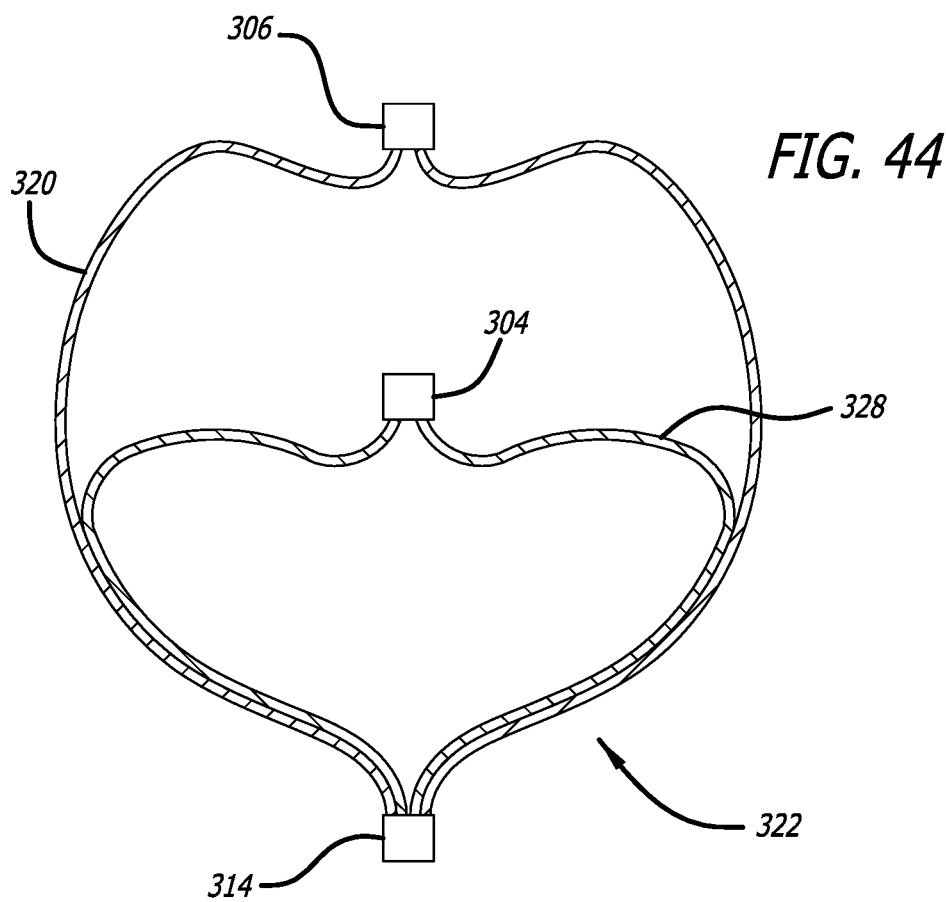
FIG. 44 is an elevation view in partial section of an embodiment of a device for treatment of a patient's vasculature.
Figure 45:
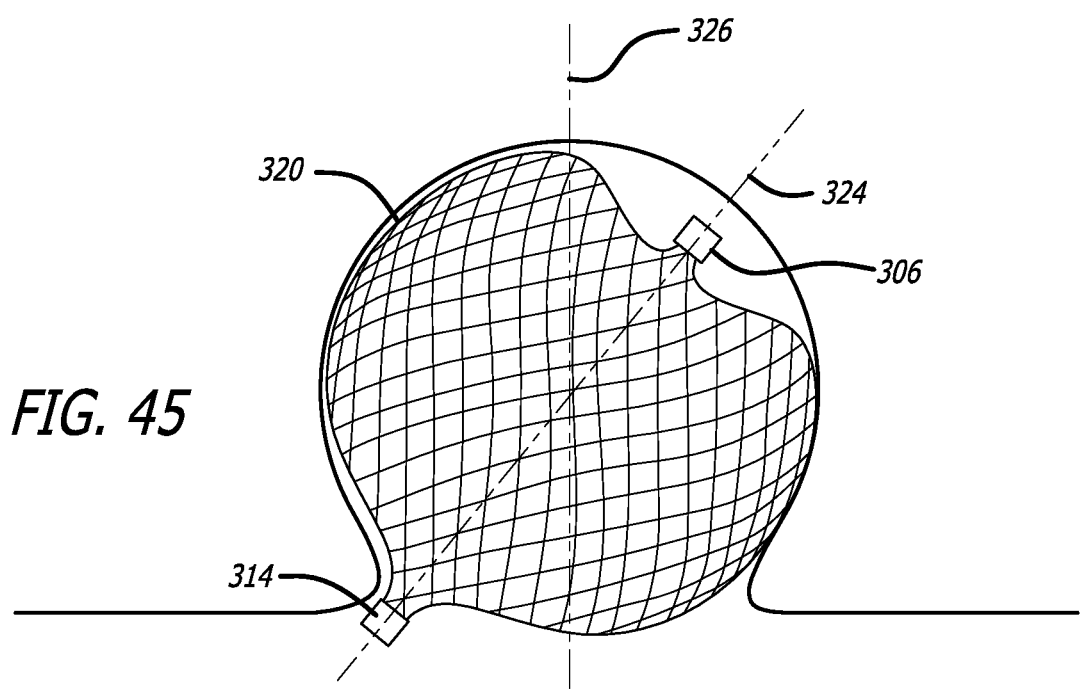
FIG. 45 is an elevation view of an embodiment of a device for treatment of a patient's vasculature.

In some embodiments, features of which are shown in FIG. 44, the outer structure 320 may have a truncated sphere or generally heart-like cross-sectional shape. The proximal portion 322 may be generally convex or semi-circular. These features allow the device to be placed into a saccular vascular site such as a cerebral aneurysm at an angled orientation relative to an axis 326 of the aneurysm as shown in FIG. 45. The semi-circular proximal surface presents a relatively constant shape to the parent vessel irrespective of the angulation of the device axis 324.

In some embodiments, the inner structure may be formed such that at least about 80% of the volume of the inner structure 328 is contained within the lower or more proximal half of the outer structure or shell volume. For some embodiments, the mesh density of the inner structure may be higher than a density of the mesh structure of the outer shell or structure. In some embodiments, the inner structure may be substantially within the proximal or lower 80% 330 of the outer shell internal volume as shown in FIG. 46.

The inner structure 328 may be formed by braiding, weaving, or other filament interlacing techniques described herein similar to that used for formation of the shell or those techniques known in the art of medical textiles and intravascular implants. Alternatively, it may be merely twisted or allowed to form a random mesh of filaments. It may be heat set as described herein and similar to that used to form the shell or it may not be heat treated beyond any heat setting done when the filaments are formed. The inner structure filaments may be metals, polymers or composites thereof. In some embodiments, the filaments are formed of materials that can withstand heat treatment of at least about 450° C. In some embodiments, some of the filaments may be formed of an aramide fiber such as poly paraphenylene terephthalamide available under the trade name Kevlar. In some embodiments, the inner structure filamentary members may be wires with a diameter between about 10 microns (0.0004 inches) and about 30 microns (0.0012 inches). The inner structure may comprise materials, coatings or be impregnated with particles or molecules that release elements or chemicals that promote thrombosis and thrombus formation.

The inner structure occupying the lower portion of the outer shell may provide rapid progression of thrombosis particularly in the distal portion of an aneurysm. In some embodiments, this configuration may provide protection of the distal "dome" portion of an aneurysm where it is generally thought to be the weakest and most prone to rupture. Thus, embodiments with proximal inner structures may provide a method of rapidly occluding a distal portion of an aneurysm that is visible under angiography. An embodiment of this process is illustrated in the angiographic images, shown in FIGS. 47 and 48 of a model aneurysm created in an animal for purpose of evaluating a device embodiment. FIG. 47 is the pre-treatment angiogram of an aneurysm created in an animal model prior to treatment with an embodiment of a device for treatment of a patient's vasculature having some similarity in structure to the device embodiment shown in FIG. 43. FIG. 48 is representative of an angiogram ten (10) minutes post treatment with the device for treatment of a patient's vasculature showing rapid occlusion of the distal portion of the aneurysm.

Generally speaking, one or more of the features, dimensions or materials of the various device embodiments discussed herein may be used in other similar device embodiments discussed herein, as well as with other device embodiments. For example, any suitable feature, dimension or material discussed here may also be applied to device embodiments such as those discussed in commonly owned U.S. Patent Publication No. 2011/0022149, published Jan. 27, 2011, titled "Methods and Devices for Treatment of Vascular Defects;" U.S. Patent Publication No. 2009/0275974, published Nov. 5, 2009, titled "Filamentary Devices for Treatment of Vascular Defects;" U.S. Patent Publication No. 2011/0152993, published Jun. 23, 2011, titled "Multiple Layer Filamentary Devices for Treatment of Vascular Defects;" and U.S. Publication No. 2012/0283768, published Nov. 8, 2012, titled "Method and Apparatus for the Treatment of Large and Giant Vascular Defects," all of which are incorporated by reference herein in their entirety.

In any of the device embodiments discussed or incorporated herein for treatment of a patient's vascular defect or aneurysm, the device may comprise one or more composite filaments. A composite filament (e.g., wires) may be defined as a filament that comprises a plurality of materials in either a mixture or alloy or in a composite structure where two materials are physically combined into one. The addition of at least some composite wires into the device may provide improved visibility of the device under external imaging such as x-ray, fluoroscopy, magnetic resonance imaging and the like. In some embodiments, composite wires may provide improved mechanical characteristics.

Figure 49:
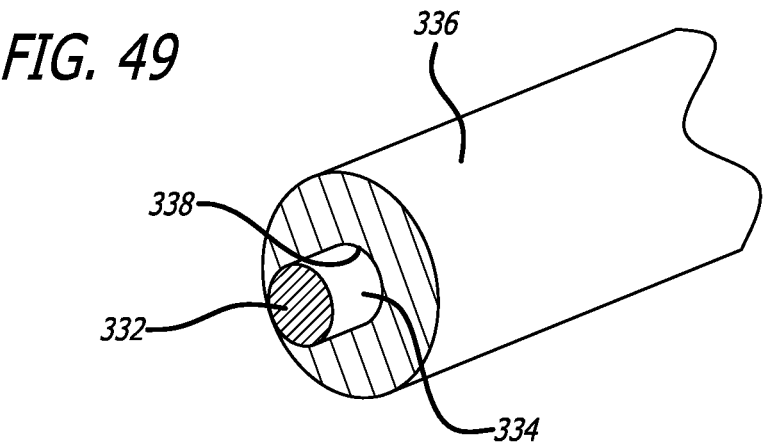
FIG. 49 is a perspective view in section of a of a composite filament embodiment.

For some composite filament embodiments, the composite filaments may be disposed in a coaxial arrangement with one material substantially inside the other as shown in FIG. 49. One known method of fabrication of such as coaxial composite wire is a drawn filled tube wire wherein the materials of the drawn filled tube are combined but retain their individual mechanical properties. Drawn filled tube wires are commercially available from Ft. Wayne Metals, Ft. Wayne, Indiana. In some cases, the process for producing drawn filled tube filaments may include extreme compressive forces such that the mechanical bond between an outer surface 334 of the internal fill wire 332 and an internal surface 338 of the external tube 336 is metallurgically sound. In some instances, a plurality of external tubes, each of a different material, may be layered over the internal wire and each other in order to combine the mechanical properties of the plurality of materials. For such embodiments, the drawn filled tube filament may include 2, 3, 4, 5 or more external tube layers. In some embodiments, the drawn filled tube wires are formed of a combination of an external nitinol (NiTi) tube and a highly radiopaque fill wire which may be concentrically disposed within the external tube. Various radiopaque materials and metals known in the art may used as the fill wire including but not limited to gold, platinum, tantalum and the like. One advantage of a composite with a NiTi exterior and internal highly radiopaque fill wire is that the device can substantially maintain its highly elastic or superelastic behavior and the majority of the blood contacting surfaces remain nitinol. This allows for a device with substantially improved visibility under x-ray imaging while maintaining the proper range of mechanical characteristics.

In some cases, the specific construction of a drawn filled tube wire or filament may be important in order to maintain desired performance characteristics of a device for treatment of a vascular defect. More specifically, it may be important to balance the stiffness, elasticity and radiopacity of the composition. In particular, for drawn filled tube filament embodiments that include an internal wire 332 of ductile radiopaque material such as platinum and an outer tube 336 of an elastic or superelastic material such as NiTi, it can be necessary to carefully balance the ratio of the percent cross sectional area of the internal wire with regard to the overall cross sectional area of the filament. Such a ratio may be referred to as a fill ratio. If an embodiment includes too little radiopaque or highly radiopaque internal tube material relative to the external tube material, there may not be sufficient radiopacity and visibility. On the other hand, if an embodiment includes too much internal wire material with respect to the elastic external tube, the mechanical properties of the ductile radiopaque material may overwhelm the elastic properties of the outer tube material and the filaments may be prone to taking a set after compression etc. resulting in permanent deformation. For some embodiments, a desired composite or drawn filled tube wire may be constructed with a fill ratio of cross sectional area of internal fill wire to cross sectional area of the entire composite filament of between about 10% and about 50%, more specifically between about 20% and about 40%, and even more specifically, between about 25% and about 35%.

In some embodiments, the number of composite wires may be between about 40 and 190, and between about 50 and 190 in other embodiments, and between about 70 and 150 in other embodiments. In some embodiments, the devices for treatment of a patient's vasculature may have at least about 25% composite wires relative to the total number of wires and in some embodiments such devices may have at least about 40% composite wires relative to a total number of wires in the device. For example, a first subset of elongate resilient filaments may comprise filaments, each having a composite of highly radiopaque material and a high strength material, and a second subset of elongate resilient filaments may consist essentially of a high strength material. For example, the highly radiopaque material may comprise platinum, platinum alloy such as 90% platinum/10% iridium, or gold or tantalum. The high strength material may comprise NiTi. While composite wires may provide enhanced visualization and/or mechanical characteristics, they may in some configurations have reduced tensile strength in comparison to NiTi wires of a similar diameter. In other configurations, depending on their diameter, the composite wires may increase the collapsed profile of the devices. Therefore, it may be beneficial to minimize the number. Lower percentages of composite wires may not be sufficiently visible with current imaging equipment particularly in neurovascular applications where the imaging is done through the skull. In addition, too many composite wires (or composite wires with extremely high fill ratios) may result in devices with excessive artifact on CT or MRI imaging. The described ratios and amounts of highly radiopaque material provide a unique situation for neurovascular implants where the periphery of the device is just visible under transcranial fluoroscopy but the device imaged area is not completely obliterated (i.e., due to artifact) as it is with conventional embolic coils that are made substantially out of platinum or platinum alloys.

One manner of achieving the desired degree of radiopacity is by selecting a particular combination of fill ratio of the composite wires and the percent of composite wires in relation to the total number of wires. Devices according to embodiments having a single layer braided (woven) structure were constructed. For example, an embodiment of a braided structure comprising 72 composite Platinum/NiTi drawn filled tube wires having a 0.00075" diameter and a platinum fill ratio of 30% and 72 NiTi wires having a 0.00075" diameter was constructed. The total percent of platinum (by total % cross sectional area) in the braided structure was about 15%. Another embodiment of a braided structure comprising 108 composite Platinum/NiTi drawn filled tube wires having a 0.001" diameter and a platinum fill ratio of 30% and 72 NiTi wires having a 0.00075" diameter was constructed. The total percent of platinum in the braided structure was about 22%. Still another embodiment of a braided structure comprising 72 composite Platinum/NiTi drawn filled tube wires having a 0.00125" diameter and a platinum fill ratio of 30% and 108 NiTi wires having a 0.00075" diameter was constructed. The total percent of platinum in the braided structure was about 19.5%. Yet another embodiment of a braided structure comprising 108 composite Platinum/NiTi drawn filled tube wires having a 0.00125" diameter and a platinum fill ratio of 30% and 108 NiTi wires having a 0.00075" diameter was constructed. The total percent of platinum in the braided structure was about 22%. Devices constructed according to each of these embodiments were each implanted into living bodies and imaged using fluoroscopy. In each case, the periphery of the device was visible under transcranial fluoroscopy but the device imaged area was not completely obliterated (i.e., due to artifact).

Additionally, devices according to embodiments having an outer braided (woven) structure and an inner braided (woven) structure (as in FIGS. 43-46) were constructed. For example, an embodiment having a braided outer structure comprising 54 composite Platinum/NiTi drawn filled tube wires having a 0.001" diameter and a platinum fill ratio of 30% and 54 NiTi wires having a 0.00075" diameter, and having a braided inner structure comprising 108 NiTi wires having a 0.00075" diameter was constructed. The total percent of platinum in the braided outer structure was about 19%. The total percent of platinum in the combined outer structure and inner structure was about 11%. Still another embodiment having a braided outer structure comprising 48 composite Platinum/NiTi drawn filled tube wires having a 0.001" diameter and a platinum fill ratio of 30% and 96 composite Platinum/NiTi drawn filled tube wires having a 0.0015" diameter and a platinum fill ratio of 30%, and having a braided inner structure comprising 132 NiTi wires having a 0.00075" diameter and 12 NiTi wires having a 0.001" diameter was constructed. The total percent of platinum in the braided outer structure was about 30%. The total percent of platinum in the combined outer structure and inner structure was about 18.5%. Devices constructed according to each of these embodiments were each implanted into living bodies and imaged using fluoroscopy. In each case, the periphery of the device was visible under transcranial fluoroscopy but the device imaged area was not completely obliterated (i.e., due to artifact).

In some embodiments the total cross sectional area of the highly radiopaque material is between about 11% and about 30% of the total cross sectional area of the plurality of elongate elements. In some embodiments the total cross sectional area of the highly radiopaque material is between about 15% and about 30% of the total cross sectional area of the plurality of elongate elements. In some embodiments the total cross sectional area of the highly radiopaque material is between about 15% and about 22% of the total cross sectional area of the plurality of elongate elements. In some embodiments the total cross sectional area of the highly radiopaque material is between about 19% and about 30% of the total cross sectional area of the plurality of elongate elements. In some embodiments the total cross sectional area of the highly radiopaque material is between about 11% and about 18.5% of the total cross sectional area of the plurality of elongate elements.

Because the radiopacity of the composite filaments comprising a highly radiopaque material can allow sufficient device visualization (e.g., on fluoroscopy), it may be desired to make one or more of the hubs 304, 306, 314 from less radiopaque or non-radiopaque materials. In some embodiments, platinum, platinum alloy (e.g., 90% Platinum/10% Iridium), may not be desired, if their radiopacity would overpower the radiopacity of the composite filaments, and thus, make their delineation difficult. The use of less radiopaque or non-radiopaque materials to make the hubs 304, 306, 314 may thus be desired in these embodiments, but can also be used on the hubs 66, 68 of other embodiments. One or more titanium or titanium alloy hubs or NiTi hubs may be used in place of highly radiopaque hubs. The use of titanium, titanium alloy, or NiTi hubs may also aid in welding to NiTi filaments, as their melt temperatures are more closely matched than if, for example, platinum, platinum alloy, or gold hubs were being used. The result can be a joint between the filaments and the hub that has a higher tensile breakage force. Joints of this variety were constructed and demonstrated an approximately 48% improvement in tensile force.

Figure 50:
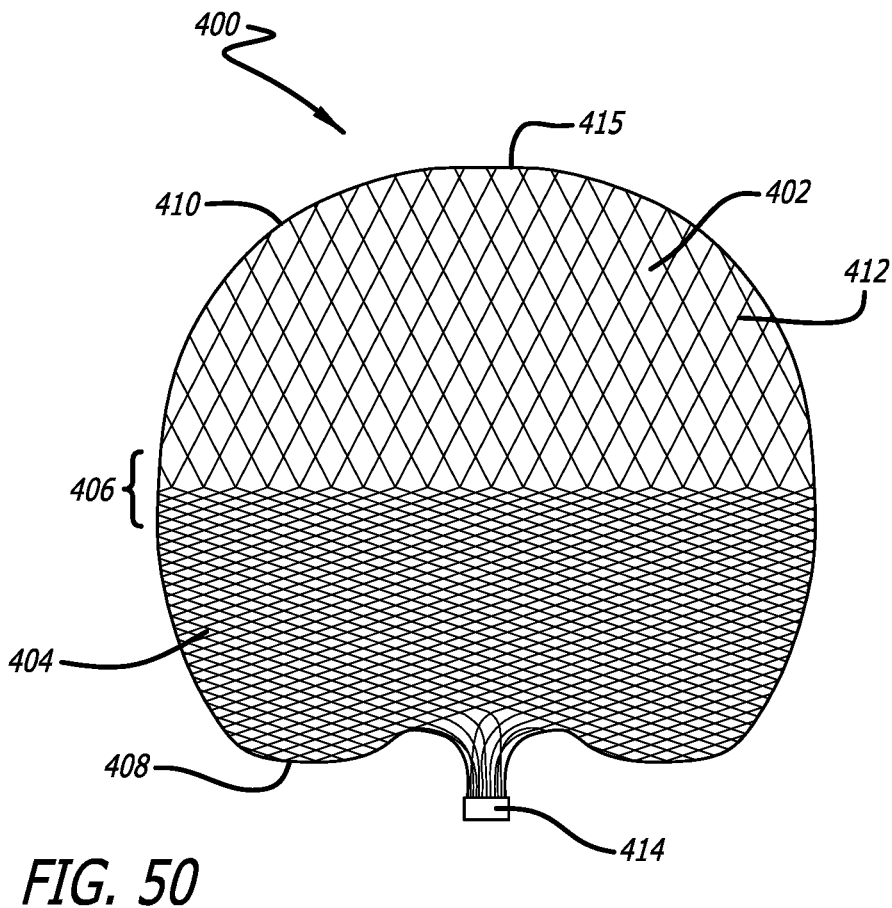
FIG. 50 is an elevation view of an embodiment of a device for treatment of a patient's vasculature.

An embodiment of a mesh (e.g., braided) device 400 having a substantially spherical expanded configuration and a substantially closed distal apex 415 is illustrated in FIG. 50 in its expanded configuration. The mesh device 400 has a first braided portion 402 having a first average braid material density BDavg1 and a second portion 404 having a second average braid material density BDavg2. The second average braid material density BDavg2 may be braided with tighter angulation to be greater than the first average braid material density BDavg1. The braid material density BD may transition from the first braided portion 402 to the second braided portion 404 over a transition zone TZ 406. Alternatively, both average braid material densities BDavg1, BDavg2 may be made the same.

The mesh device 400 has a proximal end 408 and a distal end 410, the first braided portion 402 adjacent the distal end 410 and the second braided portion 404 adjacent the proximal end 408. Individual filaments 412 from which the mesh device 400 is braided can be secured together at the proximal end 408 by a marker band 414, for example, a marker band comprising a highly radiopaque material such as platinum, a platinum alloy, or gold, or a marker band comprising a less radiopaque or non-radiopaque material, such as titanium, titanium alloy, or NiTI. Alternatively, the individual filaments 412 may be held together by welding, adhesives, expoxies or any other joining method. The adhesive or epoxy may be doped with radiopaque material, such as tantalum, in order to increase visualization. The mesh device 400, when used for the purpose of treating a vascular defect such as a cerebral aneurysm, may be placed into the aneurysm so that the second braided portion 404 covers the neck of the aneurysm. The second average braid material density BDavg2 of the second braided portion 404 can be made to be above an average braid material density BDavg that is in a range that effectively stagnates the flow of blood into the aneurysm when the mesh device 400 is expanded within the aneurysm.

Figure 51:
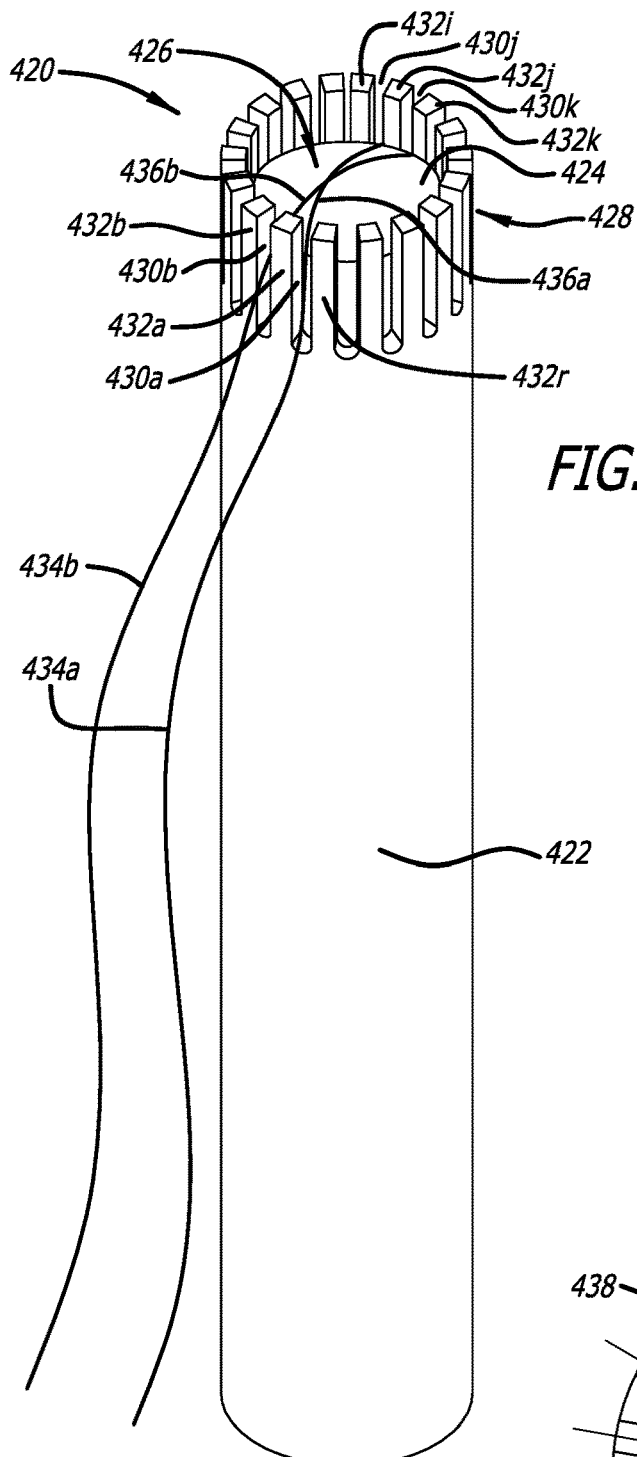
FIG. 51 is a perspective view of an embodiment of a mandrel for making the embodiment of FIG. 50.

A castellated mandrel assembly 420 for forming the substantially closed distal apex 415 of the mesh device 400 is shown in FIG. 51. The castellated mandrel assembly 420 comprises a castellated mandrel 422 having a radiused cap 424 within its central cavity 426. The castellated mandrel 422 includes a cylindrical battlement-like structure 428 having a plurality of slots, or crenels 430, separated by a plurality of posts, or merlons 432. The embodiment of FIG. 51 comprises 18 crenels 430 and 18 merlons 432, however, alternative embodiments may include 27 crenels 430 and 27 merlons 432, or other quantities. The radiused cap 424 has a convex radius whose surface is contained within the portion of the central cavity 426 surrounded by the battlement-like structure 428. The radiused cap 424 may be made from a separate structure than the castellated mandrel 422 and may, for example, comprise a pin which inserts into a central cavity in the castellated mandrel 422 for securement purposes. Alternatively, this may be a threaded union, or they may be attached with adhesive, epoxy, welding, or other joining method. The radiused cap 424 and the castellated mandrel 422 may be made from rigid, durable materials, such as stainless steel.

Figure 52:
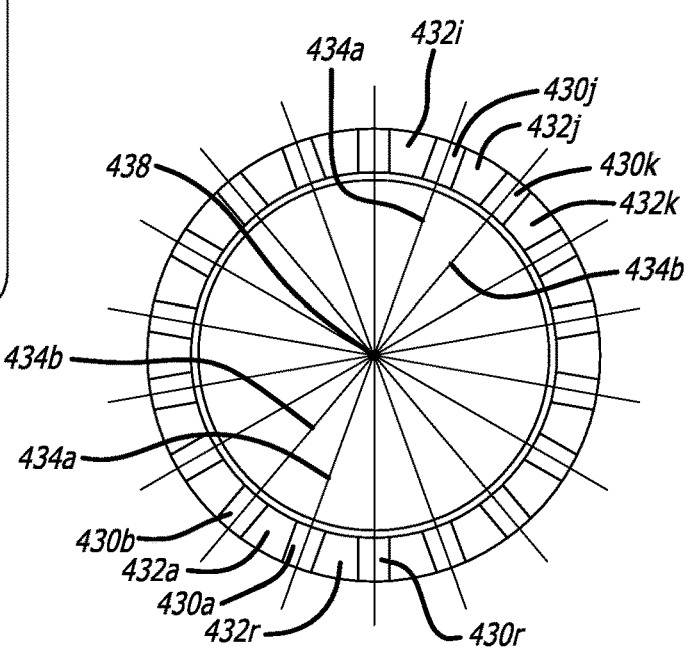
FIG. 52 is a top view of the mandrel of FIG. 51 with filaments loaded for braiding.

The loading of the castellated mandrel assembly 420 during the process of constructing the mesh device 400 of FIG. 50 is shown in FIGS. 51 and 52. Merlons 432a-r are circumferentially arrayed around the battlement-like structure 428, with crenels 430a-r between each of the merlons 432a-r. A first filament 434a is loaded in a downward direction into crenel 430a (between merlons 432r and 432a) and crenel 430j (between merlons 432i and 432j) and secured to the castellated mandrel assembly 420. The first filament 434a may be secured, for example, so that a central portion 436a of the first filament 434a is held snugly across the surface of the convex radius of the radiused cap 424. In an 18-crenel embodiment of the castellated mandrel assembly 420, the locations of crenels 430a and 430j are 180° from each other, approximating, for example, 12 o'clock and 6 o'clock locations on a clock face. Alternatively, other non-180° configurations may be used which create a hole instead of the substantially closed distal apex 415 of the mesh device 400. Continuing with the loading of filaments in the 180° configuration, a second filament 434b is loaded in a downward direction into crenel 430b (between merlons 432a and 432b) and crenel 430k (between merlons 432j and 432k) and secured to the castellated mandrel assembly 420. A central portion 436b of the second filament 434b is crossed over the central portion 436a of the first filament 434a, and held snugly across the convex radius of the radiused cap 424. This loading is continued until all filaments 434 are loaded and secured to the castellated mandrel assembly 420. Multiple filaments 434 may be loaded into each of the crenels 430, or only certain selected crenels 430. After loading all of the filaments 434 into the crenels 430 and securing the filaments 434 to the castellated mandrel assembly 420, the filaments 434 are ordered and extended radially, and the tubular braiding process is performed. The resulting mesh device of FIG. 50 has a substantially closed apex 415, because of the manner in which the filaments 434 are layered over each other at the radiused cap 424. The mesh device 400 of FIG. 50 may be made with, for example, 40 to 216 filaments 434, but because the loading of the mandrel produces the equivalent of two filaments 434 from a single piece of wire, there are only 20 to 108 pieces of wire required. The mesh device may have only the single marker band 414, as no securing of wires is needed at the distal end 410. A mixture of composite filaments and NiTi filaments may be chosen in order to achieve the desired amount of radiopacity of the entire mesh device 400. The substantially closed apex 415, though not having a marker band, can still maintain sufficient radiopacity from the radiopacity of the composite filaments alone.

FIG. 52 illustrates a top view of the loaded castellated mandrel assembly 420 of the mesh device 400, made in conjunction with the method described. Because each of the filaments 434 crosses a center crossing point 438, the substantially closed distal apex 415 of the mesh device 400 (FIG. 50) includes many layers of filaments 434 at this center crossing point 438. However, shaping and heat forming of the mesh device 400 can at least partially reform some or all of the filaments 434 at the center at the center crossing point 438, spreading them out in order to lessen the bulk at the center crossing point 438.

In some embodiments, composite filaments or wires may be made, at least in part from various single and multi-layered, coiled or braided configurations. One potentially suitable component is called a Helical Hollow Strand and is commercially available from Ft. Wayne Metals, Ft. Wayne, Indiana. Another potential construction is commercially available from Heraeus Medical Components.

One embodiment of a device for treatment of a patient's vasculature may include a self-expanding resilient permeable structure having a proximal end, a distal end, a longitudinal axis, a radially constrained elongated state configured for delivery within a catheter lumen, an expanded state with a globular and longitudinally shortened configuration relative to the radially constrained state and extending from the longitudinal axis between the proximal end and the distal end, a plurality of elongate resilient filaments secured relative to each other at at least one of the proximal end or distal end, wherein the elongate resilient filaments include a first subset of elongate resilient filaments, each of the first subset of filaments including a composite of a highly radiopaque material and a high strength material, and each of a second subset of elongate resilient filaments essentially of a high strength material, wherein the first subset of filaments is about 25% to about 40% of the total number of the plurality of elongate resilient filaments. In a particular embodiment, the high strength material of the elongate resilient filaments of the first subset of filaments and the high strength material of the elongate resilient filaments of the second subset of filaments comprise a superelastic material, for example NiTi. In one embodiment, the first subset of elongate resilient filaments may comprise about 50 to about 190 filaments. In one embodiment, the first subset of elongate resilient filaments may comprise about 70 to about 150 filaments. In one embodiment, the elongate resilient filaments may comprise drawn filled tube wires. In one embodiment, drawn filled tube wires may have a cross-sectional fill area ratio of between about 10% and about 50%. In one embodiment, drawn filled tube wires may have a cross-sectional fill area ratio of between about 20% and about 40%. In one embodiment, drawn filled tube wires may have a cross-sectional fill area ratio of between about 25% and about 35%. In one embodiment, the highly radiopaque material may include tantalum. In one embodiment, the highly radiopaque material may include platinum. In one embodiment, the highly radiopaque material may include gold.

One embodiment of a device for treatment of a patient's vasculature may include a self-expanding resilient permeable structure having a proximal end, a distal end, a longitudinal axis, a radially constrained elongated state configured for delivery within a catheter lumen, an expanded state with a globular and longitudinally shortened configuration relative to the radially constrained state and extending from the longitudinal axis between the proximal end and the distal end, a plurality of elongate resilient filaments secured relative to each other at at least one of the proximal end or distal end, wherein the elongate resilient filaments include a first subset of elongate resilient filaments, each of the first subset of filaments including a composite of a highly radiopaque material and a high strength material, and each of a second subset of elongate resilient filaments essentially of a high strength material, wherein the first subset of filaments is at least about 25% of the total number of the plurality of elongate resilient filaments. In a particular embodiment, the high strength material of the elongate resilient filaments of the first subset of filaments and the high strength material of the elongate resilient filaments of the second subset of filaments comprise a superelastic material, for example NiTi. In one embodiment, the first subset of filaments is at least 40% of the total number of the plurality of elongate resilient filaments. In one embodiment, the first subset of elongate resilient filaments may comprise about 50 to about 190 filaments. In one embodiment, the first subset of elongate resilient filaments may comprise about 70 to about 150 filaments. In one embodiment, the elongate resilient filaments may comprise drawn filled tube wires. In one embodiment, drawn filled tube wires may have a cross-sectional fill area ratio of between about 10% and about 50%. In one embodiment, drawn filled tube wires may have a cross-sectional fill area ratio of between about 20% and about 40%. In one embodiment, drawn filled tube wires may have a cross-sectional fill area ratio of between about 25% and about 35%. In one embodiment, the highly radiopaque material may include tantalum. In one embodiment, the highly radiopaque material may include platinum. In one embodiment, the highly radiopaque material may include gold.

One embodiment of a device for treatment of a patient's vasculature may include a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, which define a cavity of the permeable shell and which include at least about 40% composite filaments relative to a total number of filaments, the composite filaments including a high strength material and a highly radiopaque material. In one embodiment, the plurality of elongate filaments may be secured relative to each other at a distal end of the permeable shell. In one embodiment, the plurality of elongate filaments may be secured relative to each other at a proximal end of the permeable shell. In one embodiment, the plurality of elongate filaments may include about 50 to about 190 composite filaments. In one embodiment, the plurality of elongate filaments may include about 70 to about 150 composite filaments. In one embodiment, the composite filaments may be drawn filled tubes. In one embodiment, drawn filled tube wires may have a fill ratio of cross sectional area of between about 10% and about 50%. In one embodiment, drawn filled tube wires may have a fill ratio of cross sectional area of between about 20% and about 40%. In one embodiment, drawn filled tube wires may have a fill ratio of cross sectional area of between about 25% and about 35%. %. In one embodiment, the highly radiopaque material may include tantalum. In one embodiment, the highly radiopaque material may include platinum. In one embodiment, the highly radiopaque material may include gold.

One embodiment of a device for treatment of a patient's vasculature may include a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, the plurality of filaments having a total cross sectional area and further defining a cavity of the permeable shell and which include at least some composite filaments, the composite filaments including a high strength material and a highly radiopaque material, and wherein the total cross sectional area of the highly radiopaque material is between about 11% and about 30% of the total cross sectional area of the plurality of elongate filaments. In one embodiment, the total cross sectional area of the highly radiopaque material is between about 15% and about 30% of the total cross sectional area of the plurality of elongate filaments. In one embodiment, the total cross sectional area of the highly radiopaque material is between about 15% and about 22% of the total cross sectional area of the plurality of elongate filaments. In one embodiment, the total cross sectional area of the highly radiopaque material is between about 19% and about 30% of the total cross sectional area of the plurality of elongate filaments. In one embodiment, the total cross sectional area of the highly radiopaque material is between about 11% and about 18.5% of the total cross sectional area of the plurality of elongate filaments. In one embodiment, the plurality of elongate filaments may be secured relative to each other at a distal end of the permeable shell. In one embodiment, the plurality of elongate filaments may be secured relative to each other at a proximal end of the permeable shell. In one embodiment, the plurality of elongate filaments may include about 50 to about 190 composite filaments. In one embodiment, the plurality of elongate filaments may include about 70 to about 150 composite filaments. In one embodiment, the composite filaments may be drawn filled tubes. In one embodiment, drawn filled tube wires may have a fill ratio of cross sectional area of between about 10% and about 50%. In one embodiment, drawn filled tube wires may have a fill ratio of cross sectional area of between about 20% and about 40%. In one embodiment, drawn filled tube wires may have a fill ratio of cross sectional area of between about 25% and about 35%. In one embodiment, the highly radiopaque material may include tantalum. In one embodiment, the highly radiopaque material may include platinum. In one embodiment, the highly radiopaque material may include gold.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A device for treatment of a patient's vasculature, comprising:
    a resilient self-expanding permeable implant comprising a plurality of elongate filaments secured in a hub at a proximal end of the permeable implant, wherein the plurality of elongate filaments have a diameter between about 0.0005 inches to about 0.005 inches, the permeable implant comprising at least some filaments consisting of nitinol and at least some composite filaments, the composite filaments comprising drawn filled tube wires each comprising an external nitinol tube and a radiopaque material concentrically disposed within the external tube, and wherein the permeable implant has at least about 40% composite filaments relative to a total number of filaments, and wherein a total number of filaments is about 10 to about 300.

2. The device of claim 1, wherein the drawn filled tube wires have a fill ratio of cross sectional area selected from the group consisting of between about 10% and about 50%, between about 20% and about 40%, and between about 25% and about 35%.

3. The device of claim 1, wherein the radiopaque material of the composite filaments comprises a material selected from the group consisting of tantalum, platinum, and gold.

4. The device of claim 1, wherein each of the composite filaments has a diameter selected from the group consisting of 0.00075", 0.001", 0.0015", and 0.00125".

5. The device of claim 1, wherein the permeable shell has an expanded state having a globular configuration.

6. The device of claim 1, wherein the plurality of elongate filaments are further secured in a distal hub at a distal end of the permeable implant.

7. The device of claim 1, wherein the total number of filaments is selected from the group consisting of about 70 to about 300, about 10 to about 100, about 60 to about 80, about 100 to about 200, and about 80 to about 180.

8. The device of claim 1, wherein each filament of the plurality of elongate filaments has a diameter selected from the group consisting of between about 0.0008 inches to about 0.004 inches, between about 0.001 inches to about 0.003 inches, and between about 0.0004 inches to about 0.002 inches.

9. The device of claim 1, further comprising a tether coupled to the proximal end of the permeable implant, wherein the tether is configured to be releasably coupled to a delivery apparatus.

10. A method for treating a patient's vasculature, comprising the steps of:
    advancing a resilient self-expanding permeable implant coupled to a pusher within a catheter to a region of interest within the patient's vasculature,
        wherein the permeable implant comprises a plurality of elongate filaments secured in a hub at a proximal end of the permeable implant, wherein each of the plurality of elongate filaments has a diameter between about 0.0005 inches to about 0.005 inches, wherein the permeable implant comprises at least some filaments consisting of nitinol and at least some composite filaments, the composite filaments comprising drawn filled tube wires each comprising an external nitinol tube and a radiopaque material concentrically disposed within the external tube, and wherein the permeable implant has at least about 40% composite filaments relative to a total number of filaments, wherein a total number of filaments is about 10 to about 300;
    deploying the permeable implant in the region of interest, wherein the permeable implant expands to an expanded state; and
    detaching the permeable implant from the pusher.

11. The method of claim 10, further comprising the step of withdrawing the catheter from the region of interest after detaching the permeable implant, wherein the permeable implant is in the expanded state after the permeable implant is detached from the pusher.

12. The method of claim 11, wherein the drawn filled tube wires each have a fill ratio of cross sectional area selected from the group consisting of between about 10% and about 50%, between about 20% and about 40%, and between about 25% and about 35%.

13. The method of claim 11, wherein the radiopaque material of the composite filaments comprises a material selected from the group consisting of tantalum, platinum, and gold.

14. The method of claim 11, wherein each of the composite filaments has a diameter selected from the group consisting of 0.00075", 0.001", 0.0015", and 0.00125".

15. The method of claim 11, wherein the expanded state has a globular configuration.

16. The method of claim 11, wherein the plurality of elongate filaments are further secured in a distal hub at a distal end of the permeable implant.

17. The method of claim 11, wherein the plurality of elongate filaments are secured relative to each other at a proximal end of the permeable implant.

18. The method of claim 11, wherein the region of interest is a cerebral aneurysm.

19. The method of claim 11, wherein the region of interest is a vessel.

20. The method of claim 11, wherein the total number of filaments is selected from the group consisting of about 70 to about 300, about 10 to about 100, about 60 to about 80, about 100 to about 200, and about 80 to about 180.

21. The method of claim 11, wherein each filament of the plurality of elongate filaments has a diameter selected from the group consisting of between about 0.0008 inches to about 0.004 inches, between about 0.001 inches to about 0.003 inches, and between about 0.0004 inches to about 0.002 inches.

* * * * *